US009340503B2

(12) United States Patent
Shuttleworth et al.

(10) Patent No.: US 9,340,503 B2
(45) Date of Patent: *May 17, 2016

(54) SCRIPTAID ISOSTERES AND THEIR USE IN THERAPY

(71) Applicant: Karus Therapeutics Limited, Southampton, Hampshire (GB)

(72) Inventors: Stephen Joseph Shuttleworth, Southampton (GB); Cyrille Davy Tomassi, Southampton (GB)

(73) Assignee: Karus Therapeutics, Limited, Hampshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/266,197

(22) Filed: Apr. 30, 2014

(65) Prior Publication Data

US 2014/0235671 A1 Aug. 21, 2014

Related U.S. Application Data

(63) Continuation of application No. 13/145,250, filed as application No. PCT/GB2010/050116 on Jan. 26, 2010, now Pat. No. 8,748,458.

(30) Foreign Application Priority Data

Jan. 28, 2009 (GB) .................................. 0901406.9
Jul. 16, 2009 (GB) .................................. 0912383.7

(51) Int. Cl.

| C07D 213/34 | (2006.01) |
|---|---|
| C07D 213/55 | (2006.01) |
| C07D 213/24 | (2006.01) |
| C07D 213/74 | (2006.01) |
| C07D 401/06 | (2006.01) |
| C07D 401/12 | (2006.01) |
| A61K 31/4706 | (2006.01) |
| A61K 31/444 | (2006.01) |
| A61K 31/4709 | (2006.01) |
| A61K 45/06 | (2006.01) |
| C07D 213/40 | (2006.01) |
| A61K 31/4433 | (2006.01) |
| A61K 31/47 | (2006.01) |
| C07D 213/22 | (2006.01) |
| C07D 213/38 | (2006.01) |

(52) U.S. Cl.
CPC ............ *C07D 213/55* (2013.01); *A61K 31/444* (2013.01); *A61K 31/4706* (2013.01); *A61K 31/4709* (2013.01); *A61K 45/06* (2013.01); *C07D 213/24* (2013.01); *C07D 213/34* (2013.01); *C07D 213/74* (2013.01); *C07D 401/06* (2013.01); *C07D 401/12* (2013.01); *A61K 31/4433* (2013.01); *A61K 31/47* (2013.01); *C07D 213/22* (2013.01); *C07D 213/38* (2013.01); *C07D 213/40* (2013.01)

(58) Field of Classification Search
CPC .............. A61K 31/4706; A61K 31/47; A61K 31/4433; C07D 213/38; C07D 213/34; C07D 213/22
See application file for complete search history.

(56) References Cited

U.S. PATENT DOCUMENTS

| 8,748,458 B2 * | 6/2014 | Shuttleworth et al. ........ 514/312 |
| 2002/0099210 A1 | 7/2002 | Alexander et al. |

(Continued)

FOREIGN PATENT DOCUMENTS

| EP | 0226099 A2 | 6/1987 |
| EP | 0509400 A1 | 10/1992 |

(Continued)

OTHER PUBLICATIONS

Kirin, Eur J Inorg Chem, 2007, p. 3686-3694.*

(Continued)

*Primary Examiner* — D M Seaman
(74) *Attorney, Agent, or Firm* — Goodwin Procter LLP

(57) ABSTRACT

Compounds of the invention are of the formula $$R'-L\diagdown_{X=}^{R}\diagup^{W}_{n}$$
$$R'-L\diagup$$

wherein:
   ⋯ is a double bond and X is C; or
   ⋯ is a single bond and X is N, CH or $CQR_1$; and
wherein:
   n is 1 to 10;
   R is H or $QR_1$;
   each R' is independently selected from H and $QR_1$;
   each Q is independently selected from a bond, CO, NH, S, SO, $SO_2$ or O;
   each $R_1$ is independently selected from $C_1$-$C_{10}$ alkyl, $C_2$-$C_{10}$ alkenyl, $C_2$-$C_{10}$ alkynyl, substituted or unsubstituted aryl or heteroaryl, acyl, $C_1$-$C_{10}$ cycloalkyl, halogen, $C_1$-$C_{10}$ alkylaryl or $C_1$-$C_{10}$ heterocycloalkyl;
   L is a nitrogen-containing heteroaryl; and
   W is a zinc-chelating residue;
or a pharmaceutically acceptable salt thereof. The compounds are useful in therapy.

5 Claims, No Drawings

(56) References Cited

U.S. PATENT DOCUMENTS

| | | | |
|---|---|---|---|
| 2004/0106787 | A1 | 6/2004 | Kobuke et al. |
| 2008/0125440 | A1 | 5/2008 | Cai et al. |
| 2008/0207729 | A1 | 8/2008 | Pisano et al. |

FOREIGN PATENT DOCUMENTS

| | | | |
|---|---|---|---|
| EP | 0556396 A1 | | 8/1993 |
| EP | 0 887 348 A1 | | 12/1998 |
| JP | 11302254 | * | 2/1999 |
| JP | 11-302254 | | 11/1999 |
| JP | 2008-542428 | | 11/2008 |
| WO | WO-9740017 A2 | | 10/1997 |
| WO | WO03-075929 | | 9/2003 |
| WO | WO-2006037335 A2 | | 4/2006 |
| WO | WO-2006088949 | | 8/2006 |
| WO | WO 2006/131484 A1 | | 12/2006 |
| WO | WO-2006131484 | | 12/2006 |
| WO | WO 2007/050348 | | 5/2007 |
| WO | WO-2007085540 A1 | | 6/2007 |
| WO | WO 2008/007780 | | 1/2008 |
| WO | WO-2008033746 | | 3/2008 |
| WO | WO 2008/055068 A2 | | 5/2008 |
| WO | WO 2008/139987 | | 11/2008 |
| WO | WO-200903240 A1 | | 5/2009 |
| WO | WO-2009137462 A2 | | 11/2009 |
| WO | WO-2010686646 A1 | | 8/2010 |
| WO | WO-2012106343 A2 | | 8/2012 |
| WO | WO-2013052110 A1 | | 4/2013 |
| WO | WO-2014032019 A2 | | 2/2014 |
| WO | WO-2014072714 A1 | | 5/2014 |
| WO | WO-2014100227 A1 | | 6/2014 |
| WO | WO-2014181137 A1 | | 11/2014 |

OTHER PUBLICATIONS

Zakeeruddin, Biosensors & Bioelectronics, vol. 11, No. 3, pp. 305-315, 1996.*
Haquette, J Organometallic CHem, vol. 694, p. 937-941, 2009.*
Cuadro, Ana M. et al., "Synthesis of Highly Stabilised Ylides from N-[2-(1,3-Benzazolylmethyl)] Pyridinium Salts," *Tetrahedron*, 1990, 46(17):6033-6046.
Downes, J. Michael et al., "Biological Analogues. Spectroscopic Characteristics of Mercapto- and Disulfide-Copper(II) Coordination in Relation to Type 1 Proteins," *Inorg. Chem.*, 1981, 20:1081-1086.
Galardon, Erwan et al., "Modeling the inhibition of peptide deformylase by hydroxamic acids: influence of the sulfur donor," *Dalton Trans.*, 2007, p. 1047-1052.
Kato, Kaneyoshi et al., "Thromboxane Synthetase Inhibitors (TXSI). Design, Synthesis, and Evaluation of a Novel Series of ω-Pyridylalkenoic Acids," *J. Med. Chem.*, 1985, 28:287-294.
Moradei, Oscar et al., "Histone Deacetylase Inhibitors in Cancer Therapy: New Compounds and Clinical Update of Benzamide-Type Agents," *Current Topics in Medical Chemistry*, 2008, 8:841-858.
Assem et al. "Effects of a selection of histone deacetylase inhibitors on mast cell activation and airway and colonic smooth muscle contraction," *International Immunopharmacology*, 2008, 20(8): 1793-1801.
Bouchecareilh et al. "Histone deacetylase inhibitor (HDACi) suberoylanilide hydroxamic acid (SAHA)-mediated correction of α1-antitrypsin deficiency," *Journal of Biological Chemistry*, 2012, 287(45):38265-38278.
Ciarlo et al. "Epigenetics in sepsis: targeting histone deacetylases." *International Journal of Antimicrobial Agents*, 2013, vol. 42S, p. S8-S12.
Clarke et al. "Differential effects of sulforaphane on histone deacetylases, cell cycle arrest and apoptosis in normal prostate cells versus hyperplastic and cancerous prostate cells," *Mol. Nutr. Food Res.*, 2011, vol. 55, p. 999-1009.
Crisanti et al. "The HDAC inhibitor panobinostat (LBH589) inhibits mesothelioma and lung cancer cells in vitro and in vivo with particular efficacy for small cell lung cancer," *Molecular Cancer Therapeutics*, 2009, 8(8):2221-2231.

Djabali et al. "Hairless contains a novel nuclear matrix targeting signal and associates with histone deacetylase 3 in nuclear speckles," *Differentiation*, 2004, 72(8):410-418.
Giannini, Giuseppe et al., "Exploring bis-(indolyl)methane moiety as an alternative and innovative CAP group in the design of histone deacetylase (HDAC) inhibitors," *Bioorganic and Medicinal Chemistry Letters*, 2009, vol. 19, p. 2840-2843.
Gillespie et al. "Histone deacetylases are dysregulated in rheumatoid arthritis and a novel histone deacetylase 3-selective inhibitor reduces interleukin-6 production by peripheral blood mononuclear cells from rheumatoid arthritis patients," *Arthritis & Rheumatism*, 2012, 64(2):418-422.
Govindarajan et al. "Reducing HDAC6 ameliorates cognitive deficits in a mouse model for Alzheimer's disease," *EMBO Molecular Medicine*, 2013, 5(1):52-63.
Gryder et al. "Histone Deacetylase Inhibitors Equipped with Estrogen Receptor Modulation Activity," *Journal of Medicinal Chemistry*, 2013, Abstract.
Hancock et al. "HDAC inhibitor therapy in autoimmunity and transplantation," *Ann Rheum Dis.*, 2012, vol. 71 Suppl. 2, i46-i54.
Haquette et al. "Synthesis of N-functionalized 2.2'-dipyridylamine Ligands, Complexation to Ruthium (II) aned Anchoring of Complexes to Papain from Papaya Latex," *Journal of Organometallic Chemistry*, 2008, 694(6):937-941.
Hawtree at al. "The role of histone deacetylases in rheumatoid arthritis fibroblast-like synoviocytes," *Biochemical Society Transactions*, 2013, 41(3): 783-788.
Hebbel et al. "The HDAC inhibitors trichostatin A and suberoylanilide hydroxamic acid exhibit multiple modalities of benefit for the vascular pathobiology of sickle transgenic mice," *Blood*, 2010, 115(12):2483-2490.
Imesch et al. "Romidepsin reduces histone deacetylase activity, induces acetylation of histones, inhibits proliferation, and activates apoptosis in immortalized epithelial endometriotic cells," *Fertil Steril.*, 2010, 94(7):2838-2842.
Kazantsev et al. "Therapeutic application of histone deacetylase inhibitors for central nervous system disorders," *Nature Reviews: Drug Discovery*, 2008, 7(10):854-868.
Kim et al. "The relationship between cisplatin resistance and histone deacetylase isoform overexpression in epithelial ovarian cancer cell lines," *Journal of Gynecologic Oncology*, 2012, 23(3):182-189.
Kirin et al.,"Synthesis and Characterization of CU (II) Complexes with Amino Acid Substituted Di (2-pyridyl)amine Ligands," *European Journal of Inorganic Chemistry*, 2007, 2007(23):3686-3694.
Kovacs et al., "Nucleic Acid Controlled Catalysts of Carboxylic Esters Hydrolysis," *Bioorganic & Medicinal Chemistry Letters*, 2008, 18(21):5722-5724.
Kuendgen et al. "Treatment of poor-risk myelodysplastic syndromes and acute myeloid leukemia with a combination of 5-azacytidine and valproic acid," *Clinical Epigenetics*, 2011, 2(2):389-399. Abstract.
Lee et al. "In Vitro and in Vivo Osteogenic Activity of Largazole," *ACS Medical Chemistry Lett.*, 2011, 2(3):248-251.
Lemon et al. "Cardiac HDAC6 catalytic activity is induced in response to chronic hypertension," *J Mol Cell Cardiol.*, 2011, 51(1):41-50.
Mai et al. "Identification of two new synthetic histone deacetylase inhibitors that modulate globin gene expression in erythroid cells from healthy donors and patients with thalassemia," *Molecular Pramacology*, 2007, 72(5):1111-1123.
McGraw. "Romidepsin for the treatment of T-cell lymphomas," *American Journal of Health-System Pharmacy*, 2013, vol. 70, p. 1115-1122.
McKinsey. "The biology and therapeutic implications of HDACs in the heart," *Handb Exp Pharmacol.*, 2011, vol. 206, p. 57-78.
Mull et al., "Antihypertensively Active Amidoximes," *Journal of the American Chemical Society*, 1958, 80(14):3769-3772.
Nemenoff. "Wound healing: a role for HDACs in inhibition of fibroblast proliferation through repression of PDGF receptor-α. Focus on Repression of PDGF-R-α after cellular injury involves TNF-α, formation of a c-Fos-YY1 complex, and negative regulation by HDAC," *American Journal of Physiology-Cell Physiology*, 2012, vol. 302, p. C1588-C1589.

(56) References Cited

OTHER PUBLICATIONS

Patra et al. "A novel histone deacetylase (HDAC) inhibitor MHY219 induces apoptosis via up-regulation of androgen receptor expression in human prostate cancer cells," *Biomedicine & Pharmacotherapy*, 2013, vol. 67, p. 407-415.
Pham et al. "Dietary regulation of histone acetylases and deacetylases for the prevention of metabolic diseases," *Nutrients*, 2012, 4(12):1868-1886.
Piscopo et al. "H3 and H3.3 histone mRNA amounts and ratio in oral squamous cell carcinoma and leukoplakia," *Oral Diseases*, 2006, vol. 12, p. 130-136.
Price et al., "Histone Deacetylase Inhibitors: An Analysis of Recent Patenting Activity," *Expert Opinion on Therapeutic Patents*, 2007, 17(7):745-765.
Richardson et al. "Preclinical data and early clinical experience supporting the use of histone deacetylase inhibitors in multiple myeloma," *Leukemia Research*, 2013, 37(7):829-837.
Rotili et al. "Non-cancer uses of histone deacetylase inhibitors: effects on infectious diseases and betahemoglobinopathies," *Current Topics in Medicinal Chemistry*, 2009, 9(3):272-291. Abstract.
Shanmugam et al. "Role of epigenetics in inflammation-associated diseases," *Subcell Biochemistry*, 2012, vol. 61, p. 627-657.
Singh et al. "HDAC inhibitor SAHA normalizes the levels of VLCFAs in human skin fibroblasts from X-ALD patients and downregulates the expression of proinflammatory cytokines in Abcd1/2-silenced mouse astrocytes," *Journal of Lipid Research*, 2011, 52(11):2056-2069.
Su et al., "A Novel Histone Deacetylase Inhibitor Identified by High-Throughputtranscriptional Screening of a Compound Library," *American Association for Cancer Research*, 2000, 60(12):3137-3142.
Suzuki et al., "Identification of G Protein-Coupled Receptor 120-Selective Agonists Derived from PPAR [gamma] Agonists," *Journal of Medicinal Chemistry*, 2008, 51(23):7640-7644.
Torrioli et al. "Treatment with valproic acid ameliorates ADHD symptoms in fragile X syndrome boys," *American Journal of Medical Genetics*, 2010, Part A 152A, p. 1420-1427.
Usui et al., "Design Synthesis, and Biological Activity of Novel PPARgamma Ligands Based on Rosiglitazone and 15d-PGJ2," *Bioorganic & Medicinal Chemistry Letters*, 2005, 15(6):1547-1551.
Van Damme et al. "HDAc isoenzyme expression is deregulated in chronic lymphocytic leukemia B-cells and has a complex prognostic significance," *Epigenetics*, 2012, 7(12):1403-1412.
Yamamoto et al., "Structure-Activity Relationship Study of 1,4-Dihydropyridine Derivatives Blocking N-Type Calcium Channels," *Bioorganic & Medicinal Chemistry Letters*, 2006, 16(4):798-802.
Ye. "Improving insulin sensitivity with HDAC inhibitor," *Diabetes*, 2013, 62(3):685-687.

Zakeeruddin et al., "Glucose Oxidase Mediation by Soluble and Immobilized Electroacitve Detergents," *Biosensors and Bioelectronics*, 1996, 11(3):305-315.
Zhang et al. "Inhibition of histone deacetylase-induced myocardial repair is mediated by c-kit in infarcted hearts," *The Journal of Biological Chemistry*, 2012, 287(47):39338-39348.
Anonymous, "Glycine, N-1H-Imidazol-1-yl-N-3-pyridazinyl-," Dec. 29, 2010, XP-002751578.
Anonymous, "Synthesis of Substituted Pyrimidinedione Derivatives as Portential Schistosomicidal Agents," STN CA Caesar Accession No. 1028, Caplus, XP-002751577, 2009.
Bruljnincx, P.C., et al., "Modeling the 2-Hls-1-Carboxylate Facial Triade: Iron—Catecholato Complexes as Structural and Functional Models of the Extradiol Cleaving Dioxygenases," J Am Chem Soc (2007) 129(8), 2275-86.
Diez-Barra, et al., "Double Michael Addition of Azoles to Methyl Propiolate: A Straightforward Entry to Ligands with Two Heterocyclic Rings,"*Tetrahedron Letters*, (2004), 45, 6937-6939.
Giannini, G., et al. "Exploring Bio-(Indolyi)Methane Molety as an Alternative and Innovative CAP Group in the Design of Histone Deacetylase (HDAC) Inhibitors,"*Biorg Med Chem Lett* (2009), 19(10), 2840-3.
Grattagliano, I, et al., "Glutathione Peroxidase, Thioredoxin, and Membrane Protein Changes in Erythrocytes Predict Ribavirin-induced Anemia" *Clin Pharmacol Ther*. (2005) 78(4)422-32.
International Search Report and Written Opinion for PCT/GB2015/053260 mailed Dec. 9, 2015 (16 pages).
International Search Report for PCT/GB2015/053256 mailed Dec. 8, 2015 (13 pages).
Lu, W., et al., "Pd-Catalyzed Selective Addition of Heteroaromatic C-H Bonds to C-C Triple Bonds Under Mild Conditions,"Org lett (2000) (19), 2927-30.
Ohashi, A, et al., "Covalent Linking of Coordination-Organized Slipped Cofacial Porphyrin Dimers," *Bull. Chem. Soc. Jpn.*, (2004), 77, 365-374.
Oyamada, J. and Kitamura, T., "Pt(II)-Catalyzed Hydroarylation Reaction of Alkynes with Pyrroles and Furans,"*Tetrahedron* (2009) 65. 3842-3847.
Peters, et al., "Synthesis and Transition Metal Complexes of 3,3-bis(1-vinylImidazol-2-yl) Propionic Acid, a New N,N,O Ligand Suitable for Copolymerisation," Inorganica Chimica Acta (2011), 374, 392-405.
Peters, L., et al., "The New Facial Tripod Ligang 3,3-bis(1-Methylimidazol-2-yl) Propionic Acid and Carbonyl Complexes Thereof Containing Manganeses and Rhenium," J. Organo Metallic Chemistry, (2004) 690, 2009-16.
Safdy, ME, et al., "Trypotophan Analogues. 1. Synthesis and Antihypertensive Activity of Positional Isomers," J. Med. Chem. (1982), 25, 723-730.

\* cited by examiner

SCRIPTAID ISOSTERES AND THEIR USE IN THERAPY

CROSS REFERENCE TO A RELATED APPLICATION

This application is a continuation application of Ser. No. 13/145,250, filed Aug. 30, 2011; which is a National Stage Application of International Application Number PCT/GB2010/050116, filed Jan. 26, 2010; which claims priority to Great Britain Application No. 0901406.9, filed Jan. 28, 2009 and Great Britain Application No. 0912383.7, filed Jul. 16, 2009; all of which are incorporated herein by reference in their entirety.

FIELD OF THE INVENTION

The present invention relates to novel compounds which act as inhibitors of histone deacetylase (HDAC) and therefore have therapeutic utility.

BACKGROUND OF THE INVENTION

HDACs are zinc metalloenzymes that catalyse the hydrolysis of acetylated lysine residues. In histones, this returns lysines to their protonated state and is a global mechanism of eukaryotic transcriptional control, resulting in tight packaging of DNA in the nucleosome. Additionally, reversible lysine acetylation is an important regulatory process for non-histone proteins. Thus, compounds which are able to modulate HDAC have important therapeutic potential.

SUMMARY OF THE INVENTION

A compound of the formula

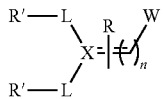

wherein:
 --- is a double bond and X is C; or
 --- is a single bond and X is N, CH or $CQR_1$; and
wherein:
 n is 1 to 10;
 R is H or $QR_1$;
 each R' is independently selected from H and $QR_1$;
 each Q is independently selected from a bond, CO, NH, S, SO, $SO_2$ or O;
 each $R_1$ is independently selected from $C_1$-$C_{10}$ alkyl, $C_2$-$C_{10}$ alkenyl, $C_2$-$C_{10}$ alkynyl, substituted or unsubstituted aryl or heteroaryl, acyl, $C_1$-$C_{10}$ cycloalkyl, halogen, $C_1$-$C_{10}$ alkylaryl or $C_1$-$C_{10}$ heterocycloalkyl;
 L is a nitrogen-containing heteroaryl; and
 W is a zinc-chelating residue;
 or a pharmaceutically acceptable salt thereof.

The compounds of the invention may be useful as an inhibitor of HDAC.

DESCRIPTION OF THE INVENTION

As used in this specification, and unless otherwise defined, the term "alkyl" refers to a straight or branched chain alkyl moiety having from one to ten carbon atoms, including, for example, methyl, ethyl, propyl, isopropyl, butyl, tert-butyl, pentyl, hexyl, heptyl, octyl, and decyl. Preferably it is $C_1$-$C_6$ alkyl group or moiety which can be linear or branched. Typically, it is a $C_1$-$C_4$ alkyl group or moiety, for example methyl, ethyl, n-propyl, i-propyl, n-butyl, sec-butyl and t-butyl. Preferred examples include methyl, i-propyl and t-butyl.

The term "alkenyl" refers to a straight or branched chain alkyl moiety having two to ten carbon atoms and having in addition one double bond, of either E or Z stereochemistry where applicable. Preferably, it is a $C_2$-$C_6$ alkenyl group or moiety which can be linear or branched. Typically, it is a $C_2$-$C_4$ alkenyl group or moiety. It is preferred that the alkenyl radicals are mono or diunsaturated, more preferably monounsaturated. Examples include vinyl, allyl, 1-propenyl, isopropenyl, 1-butenyl, 2-butenyl, 3-butenyl, and 2-butenyl, and 2-methyl-2-propenyl.

The term "alkynyl" refers to a straight or branched chain alkyl moiety having two to ten carbon atoms and having in addition one triple bond. Preferably, it is $C_{2-6}$ alkynyl, and more preferably $C_{2-4}$ alkynyl. This term includes, for example, ethynyl, 1-propargyl, and 1- and 2-butynyl.

The term "aryl" refers to an optionally substituted phenyl or naphthyl group, including benzofused systems.

The term "heteroaryl" refers to an aromatic system of between 5 and 12 ring atoms, of which at least one atom is selected from O, N and S. The term includes benzofused systems. This term includes, for example, pyridyl, pyrrolyl, pyridinyl, diazolyl, diazinyl, triazolyl, triazinyl, tetrazolyl, furanyl, oxazolyl, isoxazolyl, oxadiazolyl, benzofused furanyl, thiophenyl, pyridyl, pyrrolyl, pyridazinyl, pyrazinyl, pyrimidinyl, benzofused pyridyl, indolyl, benzofuranyl, quinolinyl, isoquinolinyl or quinazolinyl. Such rings can be linked either through carbon or nitrogen. The "heteroaryl" may be optionally substituted.

The term "heterocycloalkyl" means any partially or fully saturated analogue of "heteroaryl". "Heterocyclic" is generic to heteroaryl and heterocycloalkyl. "Cycloalkyl" means a carbocyclic analogue of a heterocycle, e.g. cyclopentyl or cylohexyl. "Cycloalkenyl" is as for cycloalkyl but contains one or more double bonds in the ring, The term "heteroalkyl" refers to an alkyl chain wherein one or more carbon atoms have been replaced by a heteroatom such as N, O or S, with the proviso that when more than one of such heteroatoms are present, they are separated by at least two carbon atoms.

Some of the groups defined above, such as aryl and heteroaryl may be "optionally substituted". Examples of such substituents are alkyl, alkenyl, alkynyl, heteroaryl, and such groups including a heteroatom such as N, O or S, and halogen, e.g. F or Cl.

In a preferred embodiment, at least one L is selected from pyridyl or a benzofused pyridyl. In a more preferred embodiment, at least one L is selected from:

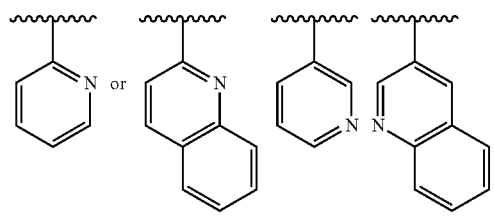

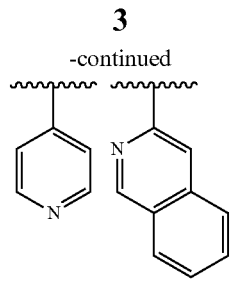

The group W is a zinc-chelating residue. Preferably, it is a metallophile capable of binding with zinc in the active site of HDAC. Suitable metallophiles are known to those skilled in the art.

In a preferred embodiment, W is selected from:

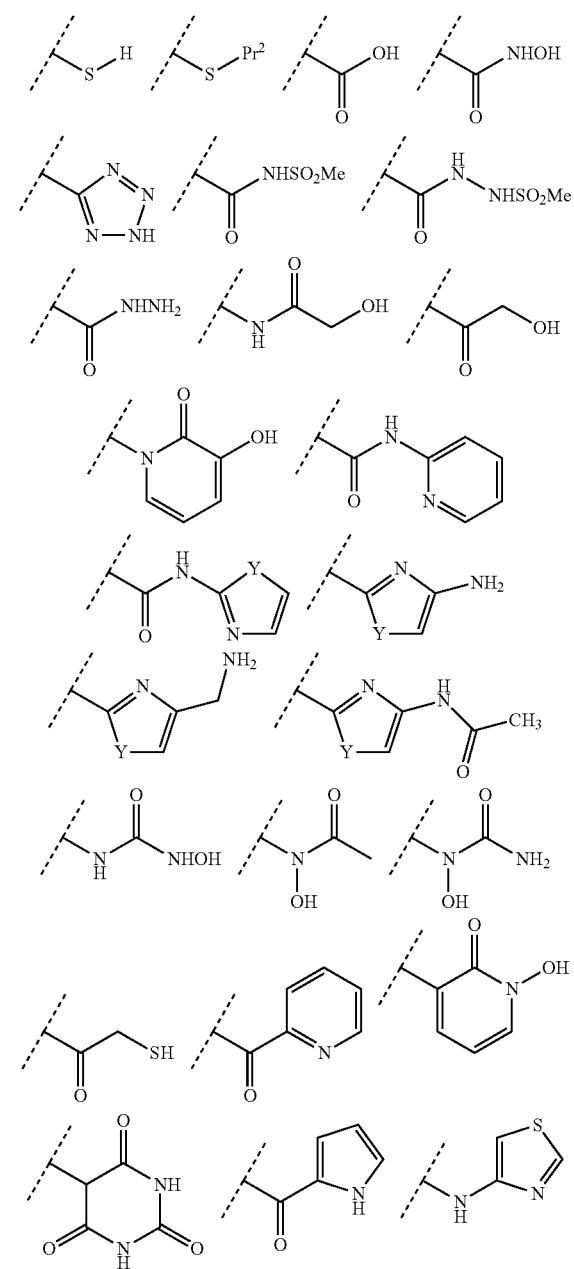

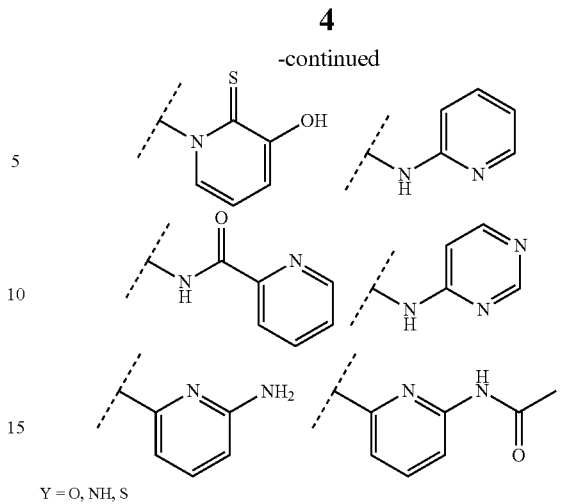

Y = O, NH, S

Preferably, W is —COOH, —CONHOH, CONHSO$_2$CH$_3$, —CONHNHSO$_2$CH$_3$, —CONHNH$_2$, —CONH(2-pyridyl) or —NHCONHOH. Even more preferably, W is —CONHOH.

Preferably, n is 3 to 6.

In a preferred embodiment, at least one R' is H, C$_1$-C$_{10}$ alkyl or O—(C$_1$-C$_{10}$ alkyl). Preferably, at least one R' is substituted or unsubstituted aryl or O-(substituted or unsubstituted aryl). Preferably, at least one R' is aryl or O-aryl, each of which may be substituted with a halogen, amino or C$_1$-C$_{10}$ alkyl. The aryl may be substituted any position. The aryl may be mono-, bis-, or tri-substituted.

R' may be substituted onto any of the ring atoms of the L group, i.e. the nitrogen-containing heteroaryl group.

A pharmaceutical composition of the invention comprises a compound as defined above, and a pharmaceutically acceptable carrier or diluent. A pharmaceutical composition of the invention typically contains up to 85 wt % of a compound of the invention. More typically, it contains up to 50 wt % of a compound of the invention. Preferred pharmaceutical compositions are sterile and pyrogen-free. Further, the pharmaceutical compositions provided by the invention typically contain a compound of the invention which is a substantially pure optical isomer. Preferably, the pharmaceutical composition comprises a pharmaceutically acceptable salt form of a compound of the invention.

As used herein, a pharmaceutically acceptable salt is a salt with a pharmaceutically acceptable acid or base. Pharmaceutically acceptable acids include both inorganic acids such as hydrochloric, sulphuric, phosphoric, diphosphoric, hydrobromic or nitric acid and organic acids such as citric, fumaric, maleic, malic, ascorbic, succinic, tartaric, benzoic, acetic, methanesulphonic, ethanesulphonic, salicylic, stearic, benzenesulphonic or p-toluenesulphonic acid. Pharmaceutically acceptable bases include alkali metal (e.g. sodium or potassium) and alkali earth metal (e.g. calcium or magnesium) hydroxides and organic bases such as alkyl amines, aryl amines or heterocyclic amines.

For the avoidance of doubt, the present invention also embraces prodrugs which react in vivo to give a compound of the present invention.

The compounds of the present invention are found to be inhibitors of HDAC. The compounds of the present invention are therefore therapeutically useful in the treatment of conditions affected by HDAC activity.

The compounds of the invention may be prepared by synthetic routes that will be apparent to those skilled in the art, e.g. based on the Examples.

The compounds of the present invention are found to be inhibitors of HDAC. The compounds of the present invention are therefore therapeutically useful.

The compounds of the invention and compositions comprising them may be administered in a variety of dosage forms. In one embodiment, a pharmaceutical composition comprising a compound of the invention may be formulated in a format suitable for oral, rectal, parenteral, intranasal or transdermal administration or administration by inhalation or by suppository. Typical routes of administration are parenteral, intranasal or transdermal administration or administration by inhalation.

The compounds of the invention can be administered orally, for example as tablets, troches, lozenges, aqueous or oily suspensions, dispersible powders or granules. Preferred pharmaceutical compositions of the invention are compositions suitable for oral administration, for example tablets and capsules.

The compounds of the invention may also be administered parenterally, whether subcutaneously, intravenously, intramuscularly, intrasternally, transdermally or by infusion techniques. The compounds may also be administered as suppositories.

The compounds of the invention may also be administered by inhalation. An advantage of inhaled medications is their direct delivery to the area of rich blood supply in comparison to many medications taken by oral route. Thus, the absorption is very rapid as the alveoli have an enormous surface area and rich blood supply and first pass metabolism is bypassed. A further advantage may be to treat diseases of the pulmonary system, such that delivering drugs by inhalation delivers them to the proximity of the cells which are required to be treated.

The present invention also provides an inhalation device containing such a pharmaceutical composition. Typically said device is a metered dose inhaler (MDI), which contains a pharmaceutically acceptable chemical propellant to push the medication out of the inhaler.

The compounds of the invention may also be administered by intranasal administration. The nasal cavity's highly permeable tissue is very receptive to medication and absorbs it quickly and efficiently, more so than drugs in tablet form. Nasal drug delivery is less painful and invasive than injections, generating less anxiety among patients. By this method absorption is very rapid and first pass metabolism is usually bypassed, thus reducing inter-patient variability. Further, the present invention also provides an intranasal device containing such a pharmaceutical composition.

The compounds of the invention may also be administered by transdermal administration. The present invention therefore also provides a transdermal patch containing a compound of the invention.

The compounds of the invention may also be administered by sublingual administration. The present invention therefore also provides a sub-lingual tablet comprising a compound of the invention.

A compound of the invention may also be formulated with an agent which reduces degradation of the substance by processes other than the normal metabolism of the patient, such as anti-bacterial agents, or inhibitors of protease enzymes which might be the present in the patient or in commensural or parasite organisms living on or within the patient, and which are capable of degrading the compound.

Liquid dispersions for oral administration may be syrups, emulsions and suspensions.

Suspensions and emulsions may contain as carrier, for example a natural gum, agar, sodium alginate, pectin, methylcellulose, carboxymethylcellulose, or polyvinyl alcohol.

The suspension or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Solutions for injection or infusion may contain as carrier, for example, sterile water or preferably they may be in the form of sterile, aqueous, isotonic saline solutions.

In one embodiment the compounds of the present invention may be used in combination with another known inhibitor of HDAC, such as SAHA. In this embodiment, the combination product may be formulated such that it comprises each of the medicaments for simultaneous, separate or sequential use.

The compounds of the present invention can be used in both the treatment and prevention of cancer and can be used in a monotherapy or in a combination therapy. When used in a combination therapy, the compounds of the present invention are typically used together with small chemical compounds such as platinum complexes, anti-metabolites, DNA topoisomerase inhibitors, radiation, antibody-based therapies (for example herceptin and rituximab), anti-cancer vaccination, gene therapy, cellular therapies, hormone therapies or cytokine therapy.

In one embodiment of the invention a compound of the invention is used in combination with another chemotherapeutic or antineoplastic agent in the treatment of a cancer. Examples of such other chemotherapeutic or antineoplastic agents include platinum complexes including cisplatin and carboplatin, mitoxantrone, vinca alkaloids for example vincristine and vinblastine, anthracycline antibiotics for example daunorubicin and doxorubicin, alkylating agents for example chlorambucil and melphalan, taxanes for example paclitaxel, antifolates for example methotrexate and tomudex, epipodophyllotoxins for example etoposide, camptothecins for example irinotecan and its active metabolite SN38 and DNA methylation inhibitors for example the DNA methylation inhibitors disclosed in WO02/085400.

According to the invention, therefore, products are provided which contain a compound of the invention and another chemotherapeutic or antineoplastic agent as a combined preparation for simultaneous, separate or sequential use in alleviating a cancer. Also provided according to the invention is the use of compound of the invention in the manufacture of a medicament for use in the alleviation of cancer by coadministration with another chemotherapeutic or antineoplastic agent. The compound of the invention and the said other agent may be administrated in any order. In both these cases the compound of the invention and the other agent may be administered together or, if separately, in any order as determined by a physician.

HDAC is believed to contribute to the pathology and/or symptomology of several different diseases such that reduction of the activity of HDAC in a subject through inhibition of HDAC may be used to therapeutically address these disease states. Examples of various diseases that may be treated using the HDAC inhibitors of the present invention are described herein.

One set of indications that HDAC inhibitors of the present invention may be used to treat is those involving undesirable or uncontrolled cell proliferation. Such indications include benign tumours, various types of cancers such as primary tumours and tumour metastasis, restenosis (e.g. coronary, carotid, and cerebral lesions), abnormal stimulation of endothelial cells (atherosclerosis), insults to body tissue due to surgery, abnormal wound healing, abnormal angiogenesis, diseases that produce fibrosis of tissue, repetitive motion disorders, disorders of tissues that are not highly vascularized, and proliferative responses associated with organ transplants. More specific indications for HDAC inhibitors include, but are not limited to prostate cancer, lung cancer, acute leukaemia, multiple myeloma, bladder carcinoma, renal carcinoma, breast carcinoma, colorectal carcinoma, neuroblastoma and melanoma.

In one embodiment, a method is provided for treating diseases associated with undesired and uncontrolled cell proliferation. The method comprises administering to a subject suffering from uncontrolled cell proliferation a therapeutically effective amount of a HDAC inhibitor according to the present invention, such that said uncontrolled cell proliferation is reduced. The particular dosage of the inhibitor to be used will depend on the severity of the disease state, the route of administration, and related factors that can be determined by the attending physician. Generally, acceptable and effective daily doses are amounts sufficient to effectively slow or eliminate uncontrolled cell proliferation.

HDAC inhibitors according to the present invention may also be used in conjunction with other agents to inhibit undesirable and uncontrolled cell proliferation. Examples of other anti-cell proliferation agents that may be used in conjunction with the HDAC inhibitors of the present invention include, but are not limited to, retinoid acid and derivatives thereof, 2-methoxyestradiol, Angiostatin™ protein, Endostatin™ protein, suramin, squalamine, tissue inhibitor of metalloproteinase-I, tissue inhibitor of metalloproteinase-2, plasminogen activator inhibitor-1, plasminogen activator inhibitor-2, cartilage-derived inhibitor, paclitaxel, platelet factor 4, protamine sulfate (clupeine), sulfated chitin derivatives (prepared from queen crab shells), sulfated polysaccharide peptidoglycan complex (sp-pg), staurosporine, modulators of matrix metabolism, including for example, proline analogs ((1-azetidine-2-carboxylic acid (LACA), cishydroxyproline, d,l-3,4-dehydroproline, thiaproline), beta-aminopropionitrile fumarate, 4-propyl-5-(4-pyridinyl)-2(3H)-oxazolone; methotrexate, mitoxantrone, heparin, interferons, 2 macroglobulin-serum, chimp-3, chymostatin, beta-cyclodextrin tetradecasulfate, eponemycin; fumagillin, gold sodium thiomalate, d-penicillamine (CDPT), beta-1-anticollagenase-serum, alpha-2-antiplasmin, bisantrene, lobenzarit disodium, n-(2-carboxyphenyl-4-chloroanthronilic acid disodium or "CCA", thalidomide; angiostatic steroid, carboxyaminoimidazole; metalloproteinase inhibitors such as BB94. Other anti-angiogenesis agents that may be used include antibodies, preferably monoclonal antibodies against these angiogenic growth factors: bFGF, aFGF, FGF-5, VEGF isoforms, VEGF-C, HGF/SF and Ang-1/Ang-2. Ferrara N. and Alitalo, K. "Clinical application of angiogenic growth factors and their inhibitors" (1999) Nature Medicine 5:1359-1364.

Generally, cells in benign tumours retain their differentiated features and do not divide in a completely uncontrolled manner. A benign tumour is usually localized and nonmetastatic. Specific types of benign tumours that can be treated using HDAC inhibitors of the present invention include hemangiomas, hepatocellular adenoma, cavernous haemangioma, focal nodular hyperplasia, acoustic neuromas, neurofibroma, bile duct adenoma, bile duct cystanoma, fibroma, lipomas, leiomyomas, mesotheliomas, teratomas, myxomas, nodular regenerative hyperplasia, trachomas and pyogenic granulomas.

In the case of malignant tumors, cells become undifferentiated, do not respond to the body's growth control signals, and multiply in an uncontrolled manner. Malignant tumors are invasive and capable of spreading to distant sites (metastasizing). Malignant tumors are generally divided into two categories: primary and secondary. Primary tumors arise directly from the tissue in which they are found. Secondary tumours, or metastases, are tumours that originated elsewhere in the body but have now spread to distant organs. Common routes for metastasis are direct growth into adjacent structures, spread through the vascular or lymphatic systems, and tracking along tissue planes and body spaces (peritoneal fluid, cerebrospinal fluid, etc.).

Specific types of cancers or malignant tumours, either primary or secondary, that can be treated using the HDAC inhibitors of the present invention include, but are not limited to, leukaemia, breast cancer, skin cancer, bone cancer, prostate cancer, liver cancer, lung cancer, brain cancer, cancer of the larynx, gallbladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteo sarcoma, Ewing's sarcoma, veticulum cell sarcoma, myeloma, giant cell tumour, small-cell lung tumour, gallstones, islet cell tumour, primary brain tumour, acute and chronic lymphocytic and granulocytic tumours, hairy-cell tumour, adenoma, hyperplasia, medullary carcinoma, pheochromocytoma, mucosal neuromas, intestinal ganglloneuromas, hyperplastic corneal nerve tumour, marfanoid habitus tumour, Wilms' tumour, seminoma, ovarian tumour, leiomyomater tumour, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumour, polycythermia vera, adenocarcinoma, glioblastoma multiforma, leukemias, lymphomas, malignant melanomas, epidermoid carcinomas, and other carcinomas and sarcomas.

The HDAC inhibitors of the present invention may also be used to treat abnormal cell proliferation due to insults to body tissue during surgery. These insults may arise as a result of a variety of surgical procedures such as joint surgery, bowel surgery, and cheloid scarring. Diseases that produce fibrotic tissue that may be treated using the HDAC inhibitors of the present invention include emphysema. Repetitive motion disorders that may be treated using the present invention include carpal tunnel syndrome. An example of a cell proliferative disorder that may be treated using the invention is a bone tumour.

Proliferative responses associated with organ transplantation that may be treated using HDAC inhibitors of the invention include proliferative responses contributing to potential organ rejections or associated complications. Specifically, these proliferative responses may occur during transplantation of the heart, lung, liver, kidney, and other body organs or organ systems.

Abnormal angiogenesis that may be treated using this invention include those abnormal angiogenesis accompanying rheumatoid arthritis, ischemic-reperfusion related brain edema and injury, cortical ischemia, ovarian hyperplasia and hypervascularity, polycystic ovary syndrome, endometriosis, psoriasis, diabetic retinopathy, and other ocular angiogenic diseases such as retinopathy of prematurity (retrolental fibroplastic), macular degeneration, corneal graft rejection, neuroscular glaucoma and Oster Webber syndrome.

Examples of diseases associated with uncontrolled angiogenesis that may be treated according to the present invention include, but are not limited to retinal/choroidal neovascularization and corneal neovascularization. Examples of diseases which include some component of retinal/choroidal neovascularization include, but are not limited to, Best's diseases, myopia, optic pits, Stargart's diseases, Paget's disease, vein occlusion, artery occlusion, sickle cell anemia, sarcoid, syphilis, pseudoxanthoma elasticum carotid apo structive diseases, chronic uveitis/vitritis, mycobacterial infections, Lyme's disease, systemic lupus erythematosus, retinopathy of prematurity, Eale's disease, diabetic retinopathy, macular degeneration, Bechet's diseases, infections causing a retinitis or chroiditis, presumed ocular histoplasmosis, pars planitis, chronic retinal detachment, hyperviscosity syndromes, toxoplasmosis, trauma and post-laser complications, diseases associated with rubesis (neovascularization of the angle) and diseases caused by the abnormal proliferation of fibrovascular or fibrous tissue including all forms of proliferative vitreoretinopathy. Examples of corneal neovascularization include, but are not limited to, epidemic keratoconjunctivitis, Vitamin A deficiency, contact lens overwear, atopic keratitis, superior limbic keratitis, pterygium keratitis sicca, sjogrens, acne rosacea, phylectenulosis, diabetic retinopathy, retinopathy of prematurity, corneal graft rejection, Mooren ulcer, Terrien's marginal degeneration, marginal keratolysis, polyarteritis, Wegener sarcoidosis, Scleritis, periphigoid radial keratotomy, neovascular glaucoma and retrolental fibroplasia, syphilis, *Mycobacteria* infections, lipid degeneration, chemical burns, bacterial ulcers, fungal ulcers, Herpes simplex infections, Herpes zoster infections, protozoan infections and Kaposi sarcoma.

Chronic inflammatory diseases associated with uncontrolled angiogenesis may also be treated using HDAC inhibitors of the present invention. Chronic inflammation depends on continuous formation of capillary sprouts to maintain an influx of inflammatory cells. The influx and presence of the inflammatory cells produce granulomas and thus maintains the chronic inflammatory state. Inhibition of angiogenesis using a HDAC inhibitor alone or in conjunction with other anti-inflammatory agents may prevent the formation of the granulosmas and thus alleviate the disease. Examples of chronic inflammatory diseases include, but are not limited to, inflammatory bowel diseases such as Crohn's disease and ulcerative colitis, psoriasis, sarcoidosis, and rheumatoid arthritis.

Inflammatory bowel diseases such as Crohn's disease and ulcerative colitis are characterized by chronic inflammation and angiogenesis at various sites in the gastrointestinal tract. For example, Crohn's disease occurs as a chronic transmural inflammatory disease that most commonly affects the distal ileum and colon but may also occur in any part of the gastrointestinal tract from the mouth to the anus and perianal area. Patients with Crohn's disease generally have chronic diarrhoea associated with abdominal pain, fever, anorexia, weight loss and abdominal swelling. Ulcerative colitis is also a chronic, nonspecific, inflammatory and ulcerative disease arising in the colonic mucosa and is characterized by the presence of bloody diarrhoea. These inflammatory bowel diseases are generally caused by chronic granulomatous inflammation throughout the gastrointestinal tract, involving new capillary sprouts surrounded by a cylinder of inflammatory cells. Inhibition of angiogenesis by these inhibitors should inhibit the formation of the sprouts and prevent the formation of granulomas. Inflammatory bowel diseases also exhibit extra intestinal manifestations, such as skin lesions. Such lesions are characterized by inflammation and angiogenesis and can occur at many sites other the gastrointestinal tract. Inhibition of angiogenesis by HDAC inhibitors according to the present invention can reduce the influx of inflammatory cells and prevent lesion formation.

Sarcoidosis, another chronic inflammatory disease, is characterized as a multisystem granulomatous disorder. The granulomas of this disease can form anywhere in the body. Thus, the symptoms depend on the site of the granulomas and whether the disease is active. The granulomas are created by the angiogenic capillary sprouts providing a constant supply of inflammatory cells. By using HDAC inhibitors according to the present invention to inhibit angiogenesis, such granulomas formation can be inhibited. Psoriasis, also a chronic and recurrent inflammatory disease, is characterized by papules and plaques of various sizes. Treatment using these inhibitors alone or in conjunction with other anti-inflammatory agents should prevent the formation of new blood vessels necessary to maintain the characteristic lesions and provide the patient relief from the symptoms.

Rheumatoid arthritis (RA) is also a chronic inflammatory disease characterized by non-specific inflammation of the peripheral joints. It is believed that the blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis. Treatment using HDAC inhibitors according to the present invention alone or in conjunction with other anti-RA agents may prevent the formation of new blood vessels necessary to maintain the chronic inflammation.

The compounds of the present invention can further be used in the treatment of cardiac/vasculature diseases such as hypertrophy, hypertension, myocardial infarction, reperfusion, ischaemic heart disease, angina, arryhtmias, hypercholestremia, atherosclerosis and stroke. The compounds can further be used to treat neurodegenerative disorders/CNS disorders such as acute and chronic neurological diseases, including stroke, Huntington's disease, Amyotrophic Lateral Sclerosis and Alzheimer's disease.

The compounds of the present invention can also be used as antimicrobial agents, for example antibacterial agents. The invention therefore also provides a compound for use in the treatment of a bacterial infection. The compounds of the present invention can be used as anti-infectious compounds against viral, bacterial, fungal and parasitic infections. Examples of infections include protozoal parasitic infections (including *plasmodium, cryptosporidium parvum, toxoplasma gondii, sarcocystis neurona* and *Eimeria* sp.)

The compounds of the present invention are particularly suitable for the treatment of undesirable or uncontrolled cell proliferation, preferably for the treatment of benign tumours/hyperplasias and malignant tumours, more preferably for the treatment of malignant tumours and most preferably for the treatment of chronic lymphocytic leukaemia (CLL), breast cancer, prostate cancer, ovarian cancer, mesothelioma, T-cell lymphoma.

In a preferred embodiment of the invention, the compounds of the invention are used to alleviate cancer, cardiac hypertrophy, chronic heart failure, an inflammatory condition, a cardiovascular disease, a haemoglobinopathy, a thalassemia, a sickle cell disease, a CNS disorder, an autoimmune disease, organ transplant rejection, diabetes, osteoporosis, MDS, benign prostatic hyperplasia, oral leukoplakia, a genetically related metabolic disorder, an infection, Rubens-Taybi, fragile X syndrome, or alpha-1 antitrypsin deficiency, or to accelerate wound healing, to protect hair follicles or as an immunosuppressant.

Typically, said inflammatory condition is a skin inflammatory condition (for example psoriasis, acne and eczema), asthma, chronic obstructive pulmonary disease (COPD), rheumatoid arthritis (RA), inflammatory bowel disease (IBD), Crohn's disease or colitis.

Typically, said cancer is chronic lymphocytic leukaemia, breast cancer, prostate cancer, ovarian cancer, mesothelioma or T-cell lymphoma.

Typically, said cardiovascular disease is hypertension, myocardial infarction (MI), ischemic heart disease (IHD) (reperfusion), angina pectoris, arrhythmia, hypercholestremia, hyperlipidaemia, atherosclerosis, stroke, myocarditis, congestive heart failure, primary and secondary i.e. dilated (congestive) cardiomyopathy, hypertrophic cardiomyopathy, restrictive cardiomyopathy, peripheral vascular disease, tachycardia, high blood pressure or thrombosis.

Typically, said genetically related metabolic disorder is cystic fibrosis (CF), peroxisome biogenesis disorder or adrenoleukodystrophy.

Typically, the compounds of the invention are used as an immunosuppressant following organ transplant.

Typically, said infection is a viral, bacterial, fungal or parasitic infection, in particular an infection by *S aureus, P acne, candida* or *aspergillus*.

Typically, said CNS disorder is Huntingdon's disease, Alzheimer's disease, multiple sclerosis or amyotrophic lateral sclerosis.

In this embodiment, the compounds of the invention may be used to alleviate cancer, cardiac hypertrophy, chronic heart failure, an inflammatory condition, a cardiovascular disease, a haemoglobinopathy, a thalassemia, a sickle cell disease, a CNS disorder, an autoimmune disease, diabetes or osteoporosis, or are used as an immunosuppressant.

The compounds of the invention may also be used to alleviate chronic lymphocytic leukaemia (CLL), breast cancer, prostate cancer, ovarian cancer, mesothelioma, T-cell lymphoma, cardiac hypertrophy, chronic heart failure or a skin inflammatory condition, in particular psoriasis, acne or eczema.

The compounds of the present invention can be used in the treatment of animals, preferably in the treatment of mammals and more preferably in the treatment of humans.

The compounds of the invention may, where appropriate, be used prophylactically to reduce the incidence of such conditions.

In use, a therapeutically effective amount of a compound of the invention is administered to a patient. A typical dose is from about 0.001 to 50 mg per kg of body weight, according to the activity of the specific compound, the age, weight and conditions of the subject to be treated, the type and severity of the disease and the frequency and route of administration.

Compounds of the invention may be tested for HDAC inhibitory activity by any suitable assay, e.g. the assay described in WO2008/062201. By this assay, the compounds of the Examples each have $IC_{50}$ values of below 1 M.

The following Examples illustrate the invention.

EXAMPLE 1

N-Hydroxy-7,7-di(pyridin-2-yl)hept-6-enamide

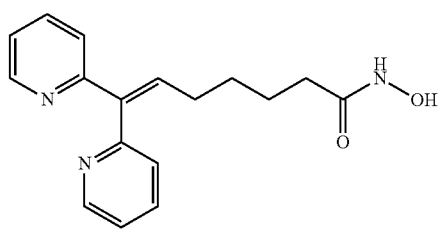 [SMILES: O=C(CCCCC=C(c1ccccn1)c1ccccn1)NO]

$IC_{50}$, Total HDAC (HeLa Nuclear Extracts)=0.95 μM $IC_{50}$, HDAC1=0.158 μM $IC_{50}$, HDAC6=0.068 μM $IC_{50}$, MCF7 Breast Tumour Cell Proliferation Inhibition=0.6 μM

EXAMPLE 2

6-(Dipyridin-2-ylamino)-N-hydroxyhexanamide

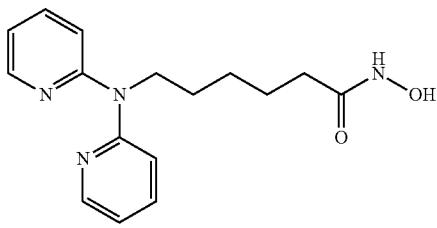 [SMILES: O=C(CCCCCN(c1ccccn1)c1ccccn1)NO]

$IC_{50}$, Total HDAC (HeLa Nuclear Extracts)=2.49 μM $IC_{50}$, MCF7 Breast Tumour Cell Proliferation Inhibition=2.34 μM

EXAMPLE 3

7-(Dipyridin-2-ylamino)-N-hydroxyheptanamide

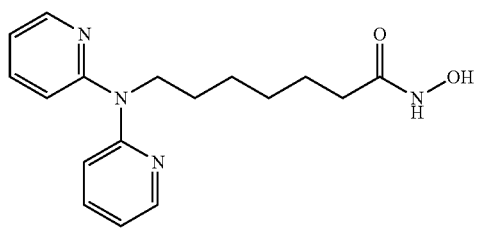 [SMILES: O=C(CCCCCCN(c1ccccn1)c1ccccn1)NO]

$IC_{50}$, Total HDAC (HeLa Nuclear Extracts)=0.245 μM $IC_{50}$, HDAC1=0.458 μM $IC_{50}$, HDAC2=1.54 μM $IC_{50}$, HDAC3=0.710 μM $IC_{50}$, HDAC4=0.307 μM $IC_{50}$, HDAC5=0.458 μM $IC_{50}$, HDAC6=0.009 μM $IC_{50}$, MCF7 Breast Tumour Cell Proliferation Inhibition=0.466 μM $IC_{50}$, TNFα inhibition (LPS-stimulated human PBMCs)=0.1 μM

EXAMPLE 4

N-Hydroxy-7-(pyridin-2-yl(quinolin-2-yl)amino)heptanamide

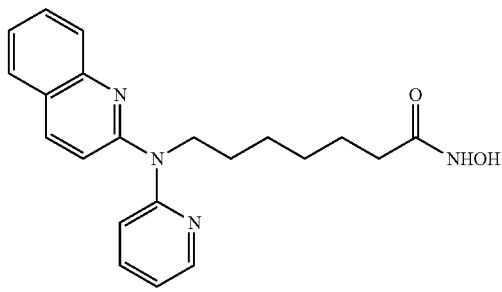

IC$_{50}$, Total HDAC (HeLa Nuclear Extracts)=0.081 μM
IC$_{50}$, HDAC1=0.071 μM
IC$_{50}$, HDAC2=0.212 μM
IC$_{50}$, HDAC3=0.062 μM
IC$_{50}$, HDAC4=0.545 μM
IC$_{50}$, HDAC5=0.123 μM
IC$_{50}$, HDAC6=0.016 μM
IC$_{50}$, HDAC7=0.157 μM
IC$_{50}$, HDAC8=0.312 μM
IC$_{50}$, HDAC9=0.090 μM
IC$_{50}$, HDAC10=0.126 μM
IC$_{50}$, HDAC11=0.112 μM
IC$_{50}$, MCF7 Breast Tumour Cell Proliferation Inhibition=0.146 μM

EXAMPLE 5

N-Hydroxy-8,8-di(pyridin-2-yl)oct-7-enamide

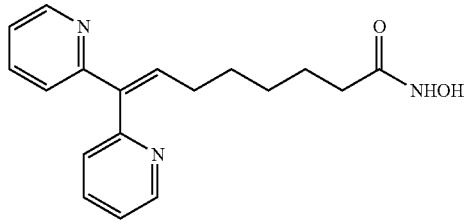

IC$_{50}$, Total HDAC (HeLa Nuclear Extracts)=0.415 μM
IC$_{50}$, HDAC1=0.642 μM
IC$_{50}$, HDAC6=0.022 μM

EXAMPLE 6

N-Hydroxy-8,8-di(pyridin-2-yl)oct-7-enamide

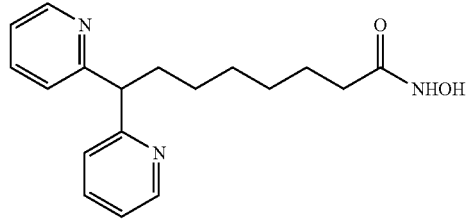

IC$_{50}$, Total HDAC (HeLa Nuclear Extracts)=0.396 μM
IC$_{50}$, MCF7 Breast Tumour Cell Proliferation Inhibition=0.445 μM

EXAMPLE 7

N-Hydroxy-7-((4-methylpyridin-2-yl)(pyridin-2-yl)amino)heptanamide

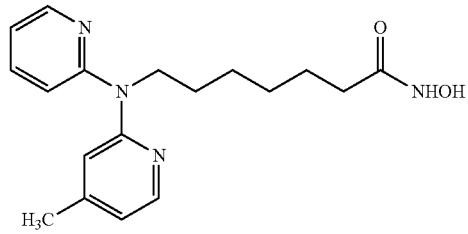

IC$_{50}$, Total HDAC (HeLa Nuclear Extracts)=0.778 μM
IC$_{50}$, MCF7 Breast Tumour Cell Proliferation Inhibition=0.448 μM

EXAMPLE 8

N-Hydroxy-7-((4-phenylpyridin-2-yl)(pyridin-2-yl)amino)heptanamide

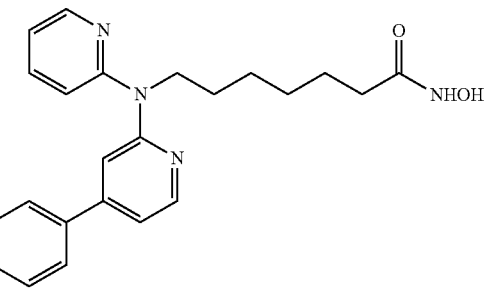

IC$_{50}$, Total HDAC (HeLa Nuclear Extracts)=0.493 μM
IC$_{50}$, HDAC1=0.116 μM
IC$_{50}$, HDAC6=0.019 μM
IC$_{50}$, MCF7 Breast Tumour Cell Proliferation Inhibition=1.05 μM

EXAMPLE 9

N-Hydroxy-7-((5-methylpyridin-2-yl)(pyridin-2-yl)amino)heptanamide

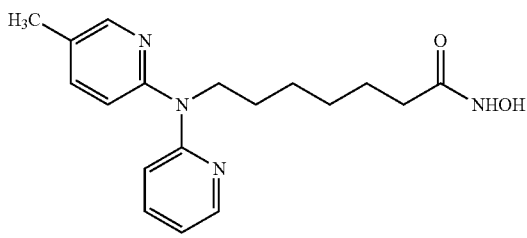

IC$_{50}$, Total HDAC (HeLa Nuclear Extracts)=0.337 μM
IC$_{50}$, HDAC1=0.453 μM
IC$_{50}$, HDAC2=1.137 μM
IC$_{50}$, HDAC6=0.031 μM
IC$_{50}$, HDAC9=0.759 μM
IC$_{50}$, MCF7 Breast Tumour Cell Proliferation Inhibition=0.697 μM

EXAMPLE 10

7-((5-(Benzyloxy)pyridin-2-yl)(pyridin-2-yl)amino)-N-hydroxyheptanamide

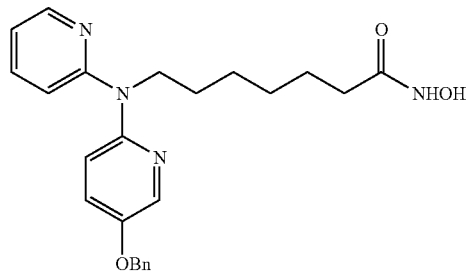

IC$_{50}$, Total HDAC (HeLa Nuclear Extracts)=1.07 μM
IC$_{50}$, HDAC1=0.182 μM
IC$_{50}$, HDAC6=0.057 μM
IC$_{50}$, MCF7 Breast Tumour Cell Proliferation Inhibition=0.285 μM

EXAMPLE 11

N-Hydroxy-7-((5-methoxypyridin-2-yl)(pyridin-2-yl)amino)heptanamide

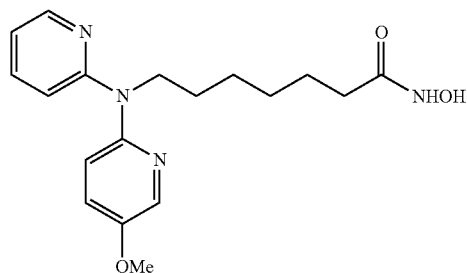

IC$_{50}$, Total HDAC (HeLa Nuclear Extracts)=0.406 μM
IC$_{50}$, HDAC1=0.182 μM
IC$_{50}$, HDAC2=0.883 μM
IC$_{50}$, HDAC6=0.013 μM
IC$_{50}$, HDAC9=0.759 μM
IC$_{50}$, MCF7 Breast Tumour Cell Proliferation Inhibition=0.292 μM

EXAMPLE 12

N-Hydroxy-7-((5-phenylpyridin-2-yl)(pyridin-2-yl)amino)heptanamide

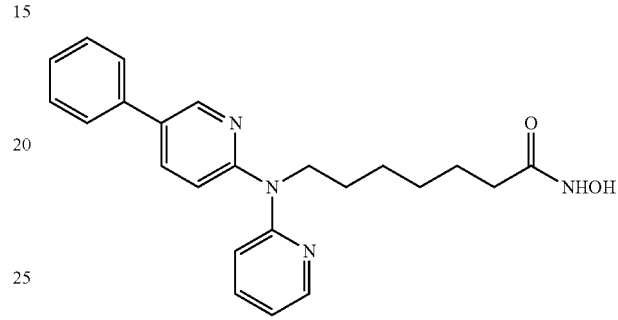

IC$_{50}$, Total HDAC (HeLa Nuclear Extracts)=0.310 μM
IC$_{50}$, MCF7 Breast Tumour Cell Proliferation Inhibition=0.081 μM

EXAMPLE 13

7-((5-(4-Fluorophenyl)pyridin-2-yl)(pyridin-2-yl)amino)-N-hydroxyheptanamide

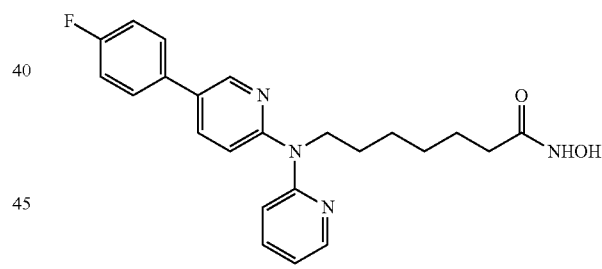

IC$_{50}$, Total HDAC (HeLa Nuclear Extracts)=0.521 μM
IC$_{50}$, MCF7 Breast Tumour Cell Proliferation Inhibition=0.357 μM

EXAMPLE 14

7-(Isoquinolin-3-yl-pyridin-2-yl-amino)-heptanoic acid hydroxyamide

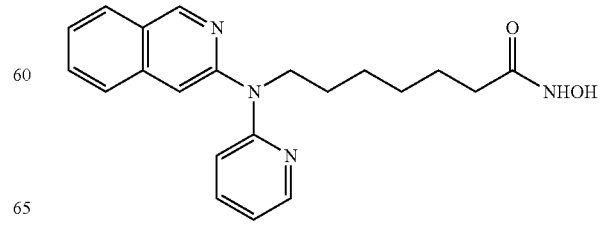

IC$_{50}$, Total HDAC (HeLa Nuclear Extracts)=0.337 μM
IC$_{50}$, HDAC1=0.064 μM
IC$_{50}$, HDAC2=0.306 μM
IC$_{50}$, HDAC6=0.002 μM
IC$_{50}$, HDAC9=0.145 μM
IC$_{50}$, MCF7 Breast Tumour Cell Proliferation Inhibition=0.169 μM

EXAMPLE 15

7-[(4-Benzyloxy-pyridin-2-yl)-pyridin-2-yl-amino]-heptanoic acid hydroxyamide

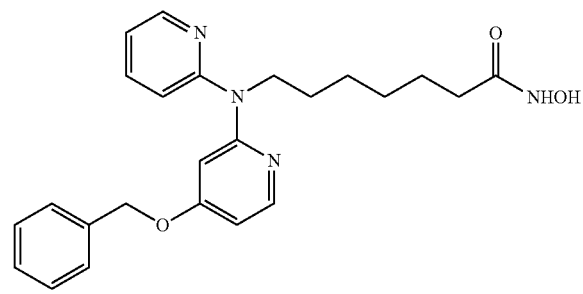

IC$_{50}$, Total HDAC (HeLa Nuclear Extracts)=1.26 μM
IC$_{50}$, HDAC1=0.151 μM
IC$_{50}$, HDAC2=0.612 μM
IC$_{50}$, HDAC6=0.003 μM
IC$_{50}$, HDAC9=0.423 μM
IC$_{50}$, MCF7 Breast Tumour Cell Proliferation Inhibition=0.411 μM

EXAMPLE 16

7-[(4-Methoxy-pyridin-2-yl)-pyridin-2-yl-amino]-heptanoic acid hydroxyamide

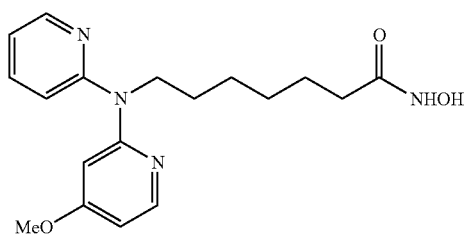

IC$_{50}$, Total HDAC (HeLa Nuclear Extracts)=1.076 μM
IC$_{50}$, MCF7 Breast Tumour Cell Proliferation Inhibition=1.09 μM

EXAMPLE 17

7-[(4-Ethoxy-pyridin-2-yl)-pyridin-2-yl-amino]-heptanoic acid hydroxyamide

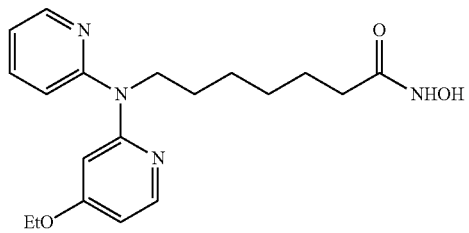

IC$_{50}$, Total HDAC (HeLa Nuclear Extracts)=0.598 μM
IC$_{50}$, MCF7 Breast Tumour Cell Proliferation Inhibition=0.456 μM

EXAMPLE 18

7-[(4-Propoxy-pyridin-2-yl)-pyridin-2-yl-amino]-heptanoic acid hydroxyamide

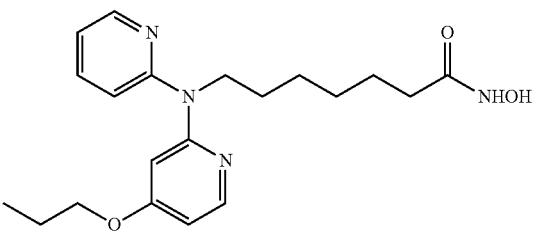

IC$_{50}$, Total HDAC (HeLa Nuclear Extracts)=0.822 μM
IC$_{50}$, MCF7 Breast Tumour Cell Proliferation Inhibition=0.574 μM

EXAMPLE 19

7-[(4-Isopropoxy-pyridin-2-yl)-pyridin-2-yl-amino]-heptanoic acid hydroxyamide

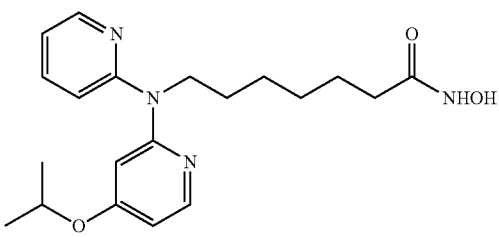

IC$_{50}$, Total HDAC (HeLa Nuclear Extracts)=0.326 μM
IC$_{50}$, MCF7 Breast Tumour Cell Proliferation Inhibition=0.478 μM

EXAMPLE 20

7-(Pyridin-3-yl-pyridin-2-yl-amino)-heptanoic acid hydroxyamide

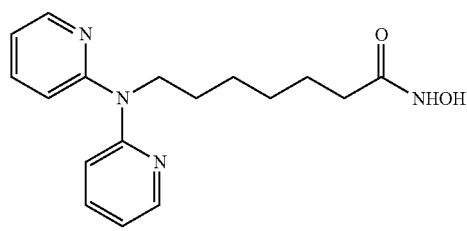

$IC_{50}$, Total HDAC (HeLa Nuclear Extracts)=0.539 μM

EXAMPLE 21

7-{[4-(4-Fluoro-phenyl)-pyridin-2-yl]-pyridin-2-yl-amino}-heptanoic acid hydroxyamide

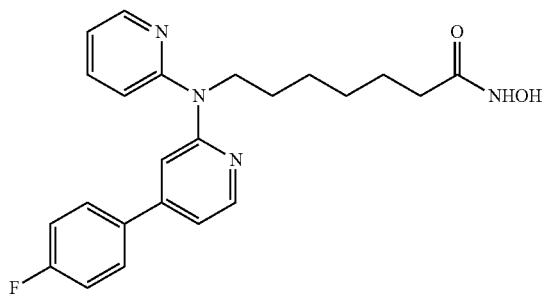

$IC_{50}$, Total HDAC (HeLa Nuclear Extracts)=1.08 μM

EXAMPLE 22

7-{[4-(4-Amino-phenyl)-pyridin-2-yl]-pyridin-2-yl-amino}-heptanoic acid hydroxyamide

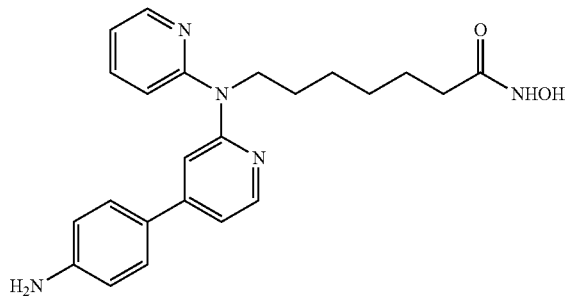

$IC_{50}$, Total HDAC (HeLa Nuclear Extracts)=0.298 μM
$IC_{50}$, MCF7 Breast Tumour Cell Proliferation Inhibition=0.039 μM

EXAMPLE 23

7-[Pyridin-2-yl-(4-p-tolyl-pyridin-2-yl)-amino]-heptanoic acid hydroxyamide

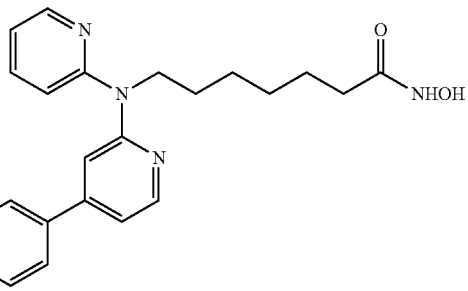

$IC_{50}$, Total HDAC (HeLa Nuclear Extracts)=1.06 μM
$IC_{50}$, MCF7 Breast Tumour Cell Proliferation Inhibition=0.077 μM

EXAMPLE 24

7-[Pyridin-2-yl-(4-o-tolyl-pyridin-2-yl)-amino]-heptanoic acid hydroxyamide

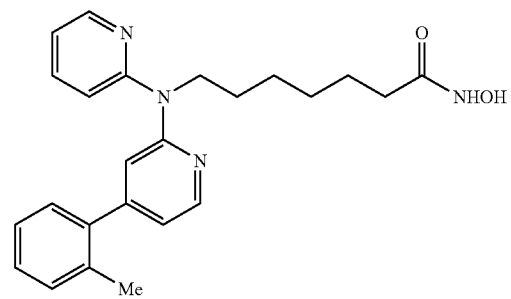

$IC_{50}$, Total HDAC (HeLa Nuclear Extracts)=1.62 μM
$IC_{50}$, MCF7 Breast Tumour Cell Proliferation Inhibition=0.20 μM

Example 25

7-{[4-(2-Chloro-phenyl)-pyridin-2-yl]-pyridin-2-yl-amino}-heptanoic acid hydroxyamide

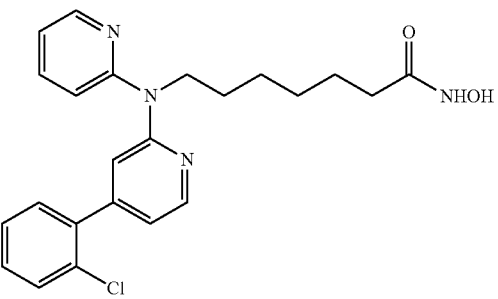

$IC_{50}$, Total HDAC (HeLa Nuclear Extracts)=1.08 μM

IC$_{50}$, MCF7 Breast Tumour Cell Proliferation Inhibition=0.21 μM

EXAMPLE 26

7-{[4-(2-Fluoro-phenyl)-pyridin-2-yl]-pyridin-2-yl-amino}-heptanoic acid hydroxyamide

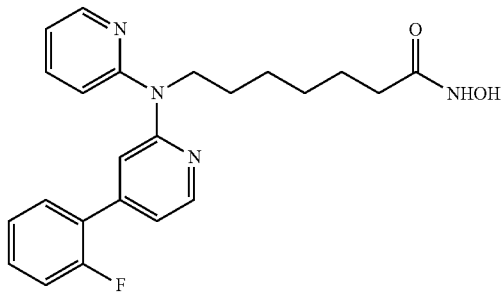

IC$_{50}$, MCF7 Breast Tumour Cell Proliferation Inhibition=0.20 μM

Example 27

7-[Pyridin-2-yl-(4-m-tolyl-pyridin-2-yl)-amino]-heptanoic acid hydroxyamide

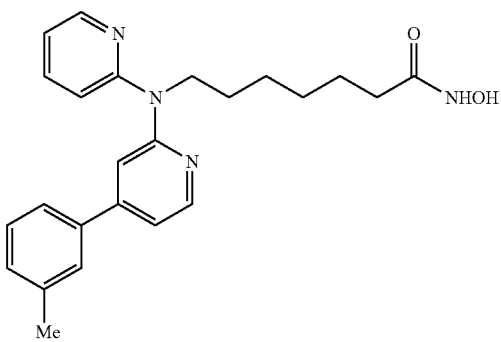

IC$_{50}$, Total HDAC (HeLa Nuclear Extracts)=1.68 μM
IC$_{50}$, MCF7 Breast Tumour Cell Proliferation Inhibition=0.081 μM Preparative Methods and Analytical Data

EXAMPLE 1

N-Hydroxy-7,7-di(pyridin-2-yl)hept-6-enamide

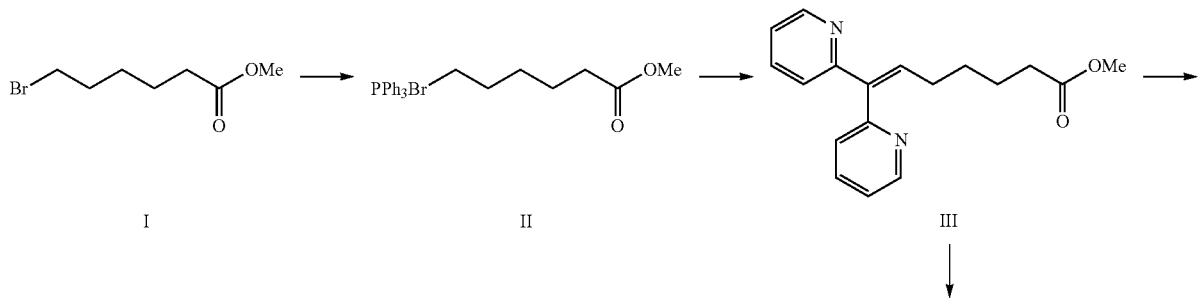

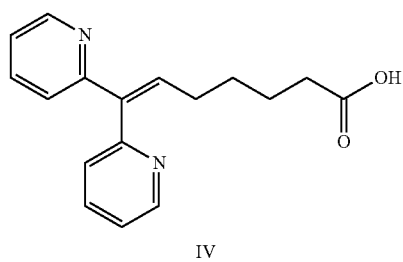

Methyl 6-triphenylphosphonium bromide hexanoate (II)

Methyl 6-bromohexanoate, I, (500 mg, 2.38 mmol) and PPh$_3$ (624 mg, 2.38 mmol) were added to acetonitrile (15 mL) and the mixture was stirred under an Ar(g) at reflux for 22 h. The solvent was subsequently removed by evaporation under reduced pressure, and the resulting phosphonium bromide derivative II was dried under high vacuum.

7,7-Di-pyridin-2-yl-hept-6-enoic acid methyl ester (III)

NHMDS (2.26 mL, 2.26 mmol) as a solution in THF was added to methyl 6-triphenylphosphonium bromide hexanoate II (1.072 g, 2.38 mmol) in THF (8 mL) at 0° C. under Ar(g). After 15 min, di-pyridin-2-yl-methanone (220 mg, 1.2 mmol) in THF (4 mL) was added; the reaction mixture was stirred for 1 h, and was then allowed to warm to rt. After 20 h stirring, water (15 mL) and EtOAc (15 mL) were added, the phases were separated, and the aqueous phase was extracted with EtOAc (2×10 mL). The organic phases were combined, dried over MgSO$_4$, filtered, and then evaporated under reduced pressure. The resulting residue was purified by silica gel column chromatography using CH$_2$Cl$_2$/MeOH (100:0.5 to 100:2) as eluant to furnish III as a colourless oil (155 mg, 44%).

$^1$H NMR (400 MHz, CDCl$_3$) $\delta_H$: 8.72 (d, J=4.8 Hz, 1H), 8.58 (d, J=4.8 Hz, 1H), 7.69-7.80 (m, 2H), 7.44-7.53 (m, 2H), 7.24-7.32 (m, 2H), 6.93 (t, J=7.7 Hz, 1H), 2.24-2.29 (m, 2H), 2.19 (q, J=7.6 Hz, 2H), 1.58-1.69 (m, 2H), 1.51-1.58 (m, 2H). MW: 296.36. LCMS (ES). found 297.3 [MH]$^+$.

7,7-Di-pyridin-2-yl-hept-6-enoic acid (IV)

LiOH (10 mg, 0.42 mmol) in water (0.2 mL) was added to III (25 mg, 0.085 mmol) in THF (0.8 mL) at rt. After 19 h, the reaction mixture was neutralized with 2N HCl, poured onto brine (2 mL), and EtOAc (3 mL) was added. The phases were separated and the aqueous phase was extracted with EtOAc (2×3 mL). The organic phases were combined, dried over MgSO$_4$, filtered, and then evaporated under reduced pressure. The resulting residue was then purified by silica gel column chromatography using CH$_2$Cl$_2$/MeOH (100:2 to 100:4) as eluant to furnish IV as a colourless oil (11.3 mg, 46%).

$^1$H NMR (400 MHz, CDCl$_3$) $\delta_H$: 8.74 (dt, J=4.8, 1.6 Hz, 1H), 8.62 (dd, J=5.0, 1.1 Hz, 1H), 7.80 (td, J=7.7, 1.7 Hz, 1H), 7.70-7.76 (m, 1H), 7.61 (td, J=7.7, 1.8 Hz, 1H), 7.44-7.55 (m, 1H), 7.14-7.21 (m, 1H), 7.01 (d, J=8.0 Hz, 1H), 6.89 (t, J=7.6 Hz, 1H), 2.29 (t, J=7.2 Hz, 2H), 2.20 (q, J=7.2 Hz, 2H), 1.61-1.70 (m, 2H), 1.53-1.61 (m, 2H), 1.43-1.50 (m, 1H). MW: 282.34. LCMS (ES). found 283.3 [MH]$^+$.

7,7-Di-pyridin-2-yl-hept-6-enoic acid hydroxyamide (V)

HONH$_2$ (50% aqueous, 0.3 mL) was added to IV (32 mg, 0.1 mmol) in DMF (0.3 mL) and THF (0.3 mL) at 0° C. The reaction mixture was stirred at rt for 17 h, after which brine (3 mL) and EtOAc (3 mL) were added. The phases were separated, and the aqueous phase was extracted with EtOAc (2×3 mL). The organic phases were then combined, dried over MgSO$_4$, filtered, and subsequently evaporated under reduced pressure. The resulting residue was purified by silica gel column chromatography using CH$_2$Cl$_2$/MeOH (100:3 to 100:10) as eluant to furnish V, a colourless oil (9.6 mg, 30%).

$^1$H NMR (300 MHz, CDCl$_3$) $\delta_H$: 8.79 (d, J=5.5 Hz, 1H), 8.68 (dd, J=5.3, 0.9 Hz, 1H), 7.94-8.01 (m, 1H), 7.86 (td, J=7.8, 1.6 Hz, 1H), 7.65-7.77 (m, 1H), 7.42-7.53 (m, 3H), 7.10 (t, J=7.5 Hz, 1H), 2.12-2.35 (m, 3H), 1.54-1.76 (m, 4H), 1.35-1.53 (m, 1H). MW 297.35. LCMS (ES). found 298.0 [MH]$^+$.

EXAMPLE 2

6-(Dipyridin-2-ylamino)-N-hydroxyhexanamide

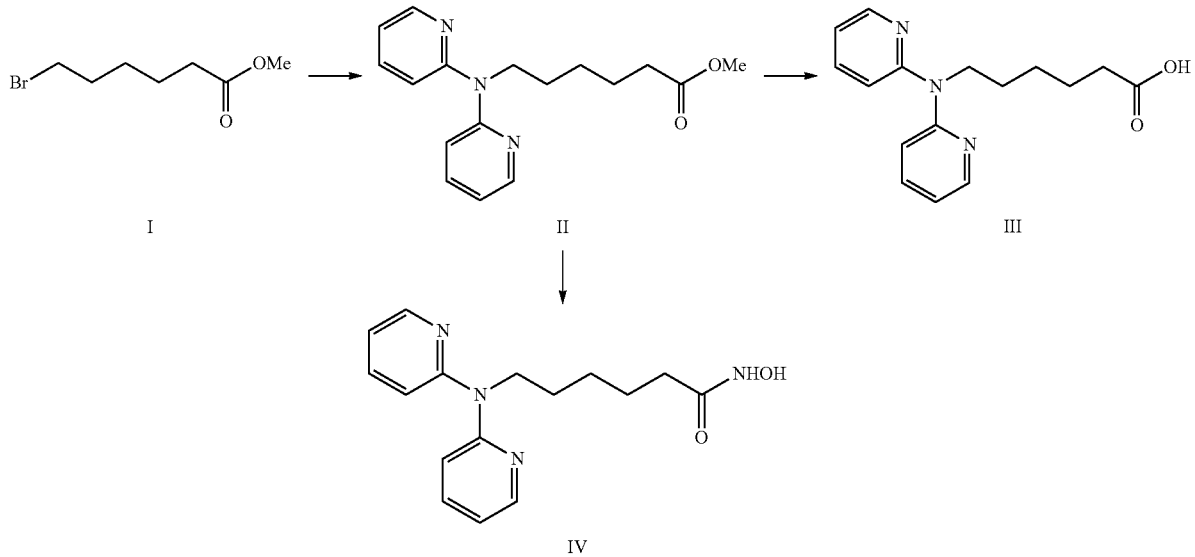

6-(Di-pyridin-2-yl-amino)-hexanoic acid methyl ester (II)

NaH (112 mg, 2.92 mmol) was added to di-pyridin-2-yl-amine (500 mg, 2.92 mmol) in DMF (10 mL) at rt. After 10 min, KI (485 mg, 2.92 mmol) and methyl 6-bromohexanoate, I (0.464 mL, 2.92 mmol) were added, and the reaction mixture was stirred at 90° C. for 21 h. Brine (200 mL) and EtOAc (200 mL) were then added, the phases were separated, and the aqueous phase was extracted with EtOAc (100 mL). The organic phases were combined, dried over MgSO$_4$, filtered, and subsequently evaporated under reduced pressure. The resulting residue was purified by silica gel column chromatography using CH$_2$Cl$_2$/MeOH (100:0.5 to 100:1) as eluant to furnish II as a colourless oil (206 mg, 24%).

$^1$H NMR (400 MHz, CDCl$_3$) $\delta_H$: 8.35 (dd, J=2.5, 1.8 Hz, 2H), 7.47-7.56 (m, 2H), 7.07 (d, J=9.2 Hz, 2H), 6.86 (dd, J=6.4, 5.6 Hz, 2H), 4.15-4.21 (m, 2H), 3.65 (s, 3H), 2.29 (t, J=7.5 Hz, 2H), 1.61-1.77 (m, 4H), 1.34-1.45 (m, 2H). MW: 299.37. LCMS (ES). found 300.3 [MH]$^+$, 322.3 [MNa]$^+$.

6-(Di-pyridin-2-yl-amino)-hexanoic acid (III)

LiOH (12 mg, 0.50 mmol) in water (0.3 mL) was added to II (33 mg, 0.11 mmol) in THF (0.8 mL) at rt. After 2 h, the reaction mixture was neutralized with 2N HCl, and was then poured onto brine (5 mL), and EtOAc (5 mL) was added. The phases were separated and the aqueous phase was extracted with EtOAc (2×2 mL). The organic phases were combined, dried over MgSO$_4$, filtered, and then evaporated under reduced pressure. The resulting residue was purified by silica gel column chromatography using CH$_2$Cl$_2$/MeOH (100:1 to 100:4) as eluant to furnish III as a colourless oil (18.1 mg, 58%).

$^1$H NMR (400 MHz, CDCl$_3$) $\delta_H$: 8.37 (ddd, J=5.0, 2.0, 0.7 Hz, 2H), 7.50-7.58 (m, 2H), 7.06 (d, J=8.4 Hz, 2H), 6.88 (ddd, J=7.2, 5.1, 0.8 Hz, 2H), 2.33 (t, J=7.5 Hz, 2H), 1.62-1.78 (m, 4H), 1.42 (quin, J=7.7 Hz, 2H). MW: 285.34. LCMS (ES). found 286.3 [MH]$^+$, 284.3 [MH]$^-$.

6-(Di-pyridin-2-yl-amino)-hexanoic acid hydroxyamide (IV)

HONH$_2$ (50% aqueous, 0.3 mL) was added to II (32 mg, 0.1 mmol) in DMF (0.3 mL) and THF (0.3 mL) at 0° C. The reaction mixture was agitated at rt for 17 h. Brine (3 mL) and EtOAc (3 mL) were added, the phases were separated, and the aqueous phase was extracted with EtOAc (2×3 mL). The organic phases were combined, dried over MgSO$_4$, filtered then evaporated under reduced pressure. The residue was purified by silica gel column chromatography with CH$_2$Cl$_2$/MeOH (100:3 to 100:10) to furnish IV as a colourless oil (9.6 mg, 30%).

$^1$H NMR (400 MHz, CDCl$_3$) $\delta_H$: 8.37 (d, J=3.3 Hz, 2H), 7.58 (t, J=7.5 Hz, 2H), 7.06 (d, J=8.21 Hz, 2H), 6.90-6.97 (m, 2H), 4.15 (t, J=7.5 Hz, 2H), 2.12-2.24 (m, 2H), 1.61-1.78 (m, 4H), 1.34-1.45 (m, 2H). MW: 300.36. LCMS (ES). found 301.2 [MH]$^+$, 323.1 [MNa]$^+$.

EXAMPLE 3

7-(Dipyridin-2-ylamino)-N-hydroxyheptanamide

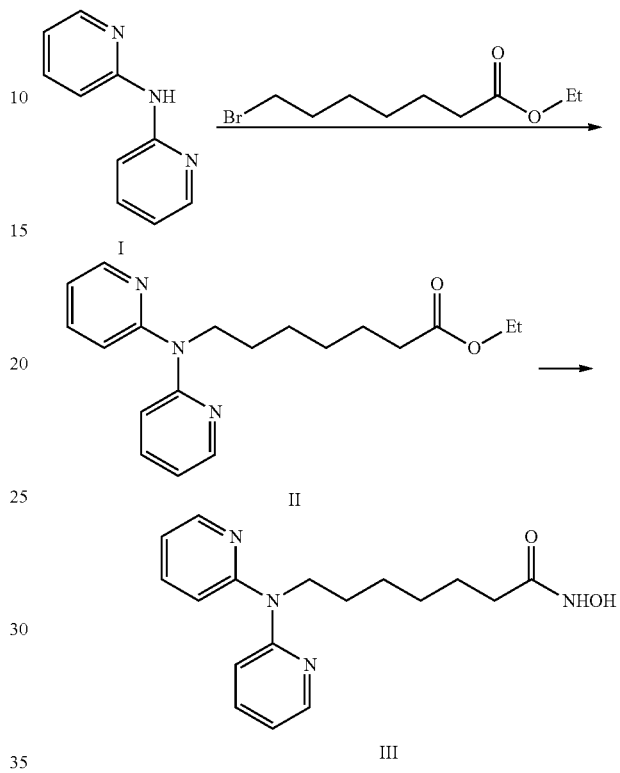

7-(Di-pyridin-2-yl-amino)-heptanoic acid ethyl ester (II)

NaH (112 mg, 2.92 mmol) was added to di-pyridyl-2-yl-amine, I, (500 mg, 2.92 mmol) in DMF (10 mL) at rt. After 10 min, KI (727 mg, 4.38 mmol) and ethyl 7-bromoheptanoate (0.854 mL, 4.38 mmol) were added, and the reaction mixture was stirred at 90° C. for 18 h. Aqueous 0.1M Na$_2$S$_2$O$_3$ (100 mL) and EtOAc (100 mL) were added, the phases were separated, and the organic phase was washed with brine (100 mL) then dried over MgSO$_4$, filtered, and subsequently evaporated under reduced pressure. The resulting residue was purified by silica gel column chromatography eluting with hexane/EtOAc (90:10 to 75:25) to furnish II as a colourless oil (490 mg, 51%).

$^1$H NMR (400 MHz, CDCl$_3$) $\delta_H$: 8.35 (dd, J=1.8, 5.3 Hz, 2H), 7.52 (dt, J=2.0, 7.0 Hz, 2H), 7.08 (d, J=8.0 Hz, 2H), 6.86 (dd, J=5.5, 7.0 Hz, 2H), 4.18 (t, J=7.5 Hz, 2H), 4.12 (q, J=7.0 Hz, 2H), 2.27 (t, J=7.5 Hz, 2H), 1.71 (td, J=7.0, 14.6 Hz, 2H), 1.61 (td, J=7.3, 14.6 Hz, 2H), 1.43-1.30 (m, 4H), 1.25 (t, J=7.0 Hz, 3H). MW: 327.42. LCMS (ES). found 327.9 [MH]$^+$.

7-(Di-pyridin-2-yl-amino)-heptanoic acid hydroxyamide (III)

HONH$_2$ (50% aqueous, 2 mL) was added to II (524 mg, 1.60 mmol) in DMF (0.5 mL) and MeOH (2 mL) at rt. The reaction mixture was stirred for 72 h, after which the solvents were evaporated under reduced pressure. The resulting residue was dissolved and co-evaporated with toluene (2×10 mL)

then was purified by silica gel column chromatography eluting with CH$_2$Cl$_2$/MeOH (100:4 then 100:8) to furnish III as a colourless oil (425.79 mg, 85%).

$^1$H NMR (400 MHz, CDCl$_3$) δ$_H$: 8.35 (d, J=4.0 Hz, 2H), 7.55 (t, J=7.3 Hz, 2H), 7.05 (d, J=8.5 Hz, 2H), 6.89 (t, J=5.5 Hz, 2H), 4.16 (t, J=7.5 Hz, 2H), 2.23-2.05 (m, 2H), 1.75-1.56 (m, J=7.0, 15.6 Hz, 4H), 1.44-1.27 (m, 4H). MW: 314.38. LCMS (ES). found 315.2 [M H]$^+$.

EXAMPLE 4

N-Hydroxy-7-(pyridin-2-yl(quinolin-2-yl)amino)heptanamide

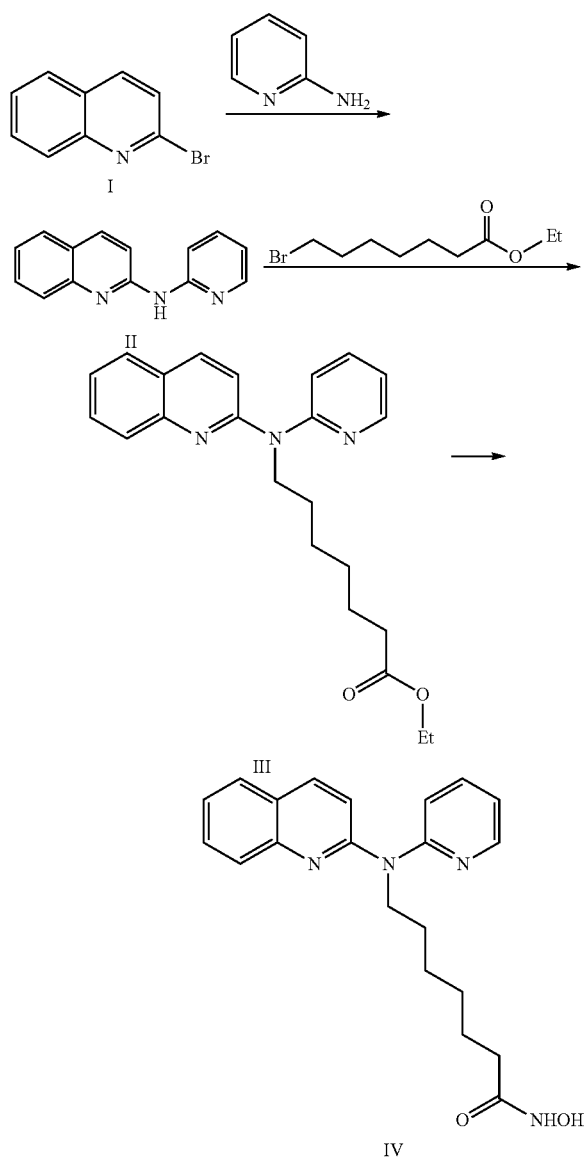

Pyridin-2-yl-quinolin-2-yl-amine (II)

2-Bromoquinoline, I (500 mg, 2.40 mmol), 2-aminopyridine (249 mg, 2.64 mmol), tBuOK (404 mg, 3.60 mmol), (±)-BINAP (6 mg, 0.01 mmol) and Pd$_2$(dba)$_3$ (5.5 mg, 0.006 mmol) were stirred in toluene (10 mL) at 90° C. under Ar(g) for 21 h. The reaction mixture was then diluted with CH$_2$Cl$_2$ (10 mL) and silica was added, followed by the removal of the solvent under reduced pressure. The resulting dry load material was purified by silica gel column chromatography eluting with CH$_2$Cl$_2$/MeOH (100:1 then 100:2) to furnish II as a colourless oil (344 mg, 45%).

$^1$H NMR (400 MHz, CDCl$_3$) δ$_H$: 8.40-8.26 (m, 2H), 8.03 (d, J=8.5 Hz, 1H), 7.86 (d, J=8.0 Hz, 1H), 7.79-7.68 (m, 2H), 7.65 (t, J=7.5 Hz, 1H), 7.38 (t, J=7.0 Hz, 2H), 7.00-6.90 (m, 1H). MW: 221.26. LCMS (ES). found 222.1 [MH]$^+$.

7-(Pyridin-2-yl-quinolin-2-yl-amino)-heptanoic acid ethyl ester (III)

NaH (35 mg, 0.91 mmol) was added to II (344 mg, 0.91 mmol) in DMF (5 mL) at rt. After 10 min, KI (227 mg, 1.37 mmol) and ethyl 7-bromoheptanoate (0.267 mL, 1.37 mmol) were added. The reaction mixture was stirred at 90° C. for 19 h after which 0.1 M Na$_2$S$_2$O$_3$ (50 mL) and EtOAc (50 mL) were added; the phases were then separated and the aqueous phase extracted with EtOAc (2×25 mL). The organic phases were combined then dried over MgSO$_4$, filtered, and subsequently evaporated under reduced pressure. The resulting residue was purified by silica gel column chromatography, eluting with hexane/EtOAc (90:10 to 85:15), to furnish III as a colourless oil (189 mg, 55%).

$^1$H NMR (400 MHz, CDCl$_3$) δ$_H$: 8.41 (dd, J=1.5, 5.0 Hz, 1H), 7.90-7.80 (m, 2H), 7.67 (d, J=8.0 Hz, 1H), 7.63-7.56 (m, 2H), 7.36-7.31 (m, J=7.5, 7.5 Hz, 1H), 7.19 (t, J=8.8 Hz, 2H), 6.95 (dd, J=5.3, 6.8 Hz, 1H), 4.35 (t, J=7.5 Hz, 2H), 4.12 (q, J=7.4 Hz, 2H), 2.28 (t, J=7.5 Hz, 2H), 1.79 (quin, J=7.3 Hz, 2H), 1.63 (quin, J=7.4 Hz, 2H), 1.48-1.35 (m, 4H), 1.25 (t, J=7.0 Hz, 3H). MW: 377.48. LCMS (ES). found 378.2 [MH]$^+$.

7-(Pyridin-2-yl-quinolin-2-yl-amino)-heptanoic acid hydroxyamide (IV)

HONH$_2$ (50% aqueous, 2 mL) was added to III (90 mg, 0.24 mmol) in DMF (0.5 mL) and MeOH (2 mL) at rt. The reaction mixture was stirred for 48 h, after which the solvents were evaporated under reduced pressure. The resulting residue was dissolved and co-evaporated with toluene (2×10 mL) then was purified by silica gel column chromatography eluting with CH$_2$Cl$_2$/MeOH (100:4) to furnish IV as a colourless oil (66.43 mg, 76%).

$^1$H NMR (400 MHz, CDCl$_3$) δ$_H$: 8.43 (dd, J=1.5, 5.0 Hz, 1H), 7.99-7.92 (m, J=6.0 Hz, 1H), 7.90 (d, J=9.0 Hz, 1H), 7.68 (d, J=8.0 Hz, 1H), 7.65-7.58 (m, J=7.0, 7.0 Hz, 2H), 7.37 (t, J=7.5 Hz, 1H), 7.18 (d, J=8.5 Hz, 1H), 7.12 (d, J=9.0 Hz, 1H), 7.05-6.98 (m, 1H), 4.36 (t, J=7.3 Hz, 2H), 2.13 (t, J=7.3 Hz, 2H), 1.77 (quin, J=7.4 Hz, 2H), 1.63 (td, J=7.0, 14.1 Hz, 2H), 1.47-1.32 (m, 4H). MW: 364.44. LCMS (ES). found 365.2 [MH]$^+$.

EXAMPLE 5

N-Hydroxy-8,8-di(pyridin-2-yl)oct-7-enamide

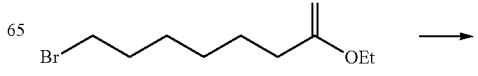

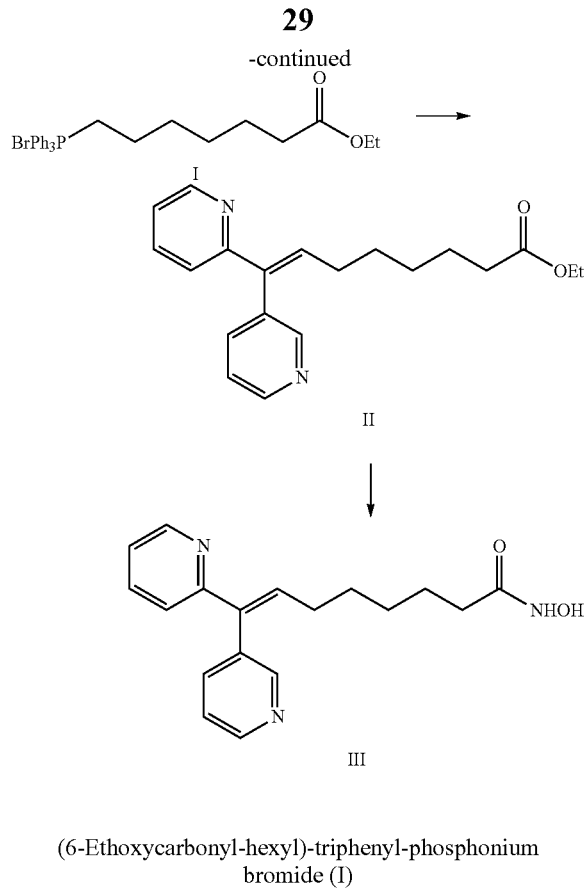

(6-Ethoxycarbonyl-hexyl)-triphenyl-phosphonium bromide (I)

Ethyl-7-bromoheptanoate (2.5 g, 10.54 mmol) and PPh$_3$ (2.764 g, 10.54 mmol) were added to acetonitrile (50 mL) and the mixture was stirred under Ar(g) at reflux for 18 h. The solvent was subsequently removed by evaporation under reduced pressure, and the resulting phosphonium bromide derivative I was dried under high vacuum.
MW: 499.42. LCMS (ES). found 419.2 [MH]$^+$.

8,8-Di-pyridin-2-yl-oct-7-enoic acid ethyl ester (II)

NaHMDS (10.01 mL, 10.01 mmol) as a solution in THF was added to (6-ethoxycarbonyl-hexyl)-triphenyl-phosphonium bromide 1 (10.54 mmol) in THF (40 mL) at −78° C. under Ar(g). After 30 min, di-pyridin-2-yl-methanone (1.437 g, 7.81 mmol) in THF (5 mL) was added; the reaction was stirred for 2 h, and was then allowed to warm to rt. After 17 h, saturated aqueous NH$_4$Cl (250 mL) and EtOAc (150 mL) were added; the phases were separated, and the aqueous phase was extracted with EtOAc (2×100 mL). The organic phases were combined, dried over MgSO$_4$, filtered, and then evaporated under reduced pressure. The resulting residue was purified by silica gel column chromatography eluting with CH$_2$Cl$_2$/MeOH (100:0.5 to 100:2) to furnish II as a pale brown oil (990 mg, 40%).
MW: 324.42. LCMS (ES). found 325.2 [MH]$^+$.

8,8-Di-pyridin-2-yl-oct-7-enoic acid hydroxyamide (III)

HONH$_2$ (50% aqueous, 0.5 mL) was added to II (68 mg, 0.21 mmol) in MeOH (0.5 mL) at rt. The reaction mixture was stirred for 72 h, after which the solvents were evaporated under reduced pressure. The resulting residue was dissolved and co-evaporated with toluene (2×5 mL), then was purified by silica gel column chromatography eluting with CH$_2$Cl$_2$/MeOH (100:1 to 100:10) to furnish III as a colourless oil (12 mg, 18%).
$^1$H NMR (400 MHz, CDCl$_3$) $\delta_H$: 8.71 (d, J=4.0 Hz, 1H), 8.57 (d, J=4.5 Hz, 1H), 7.80 (dt, J=1.3, 7.7 Hz, 1H), 7.58 (dt, J=1.8, 7.7 Hz, 1H), 7.36-7.29 (m, 2H), 7.16 (dd, J=5.0, 7.0 Hz, 1H), 6.95 (d, J=8.0 Hz, 1H), 6.85 (t, J=7.5 Hz, 1H), 2.21-2.08 (m, 4H), 1.61-1.44 (m, 4H), 1.34-1.25 (m, 2H).
MW: 311.38. LCMS (ES). found 312.1 [MH]$^+$.

EXAMPLE 6

N-Hydroxy-8,8-di(pyridin-2-yl)oct-7-enamide

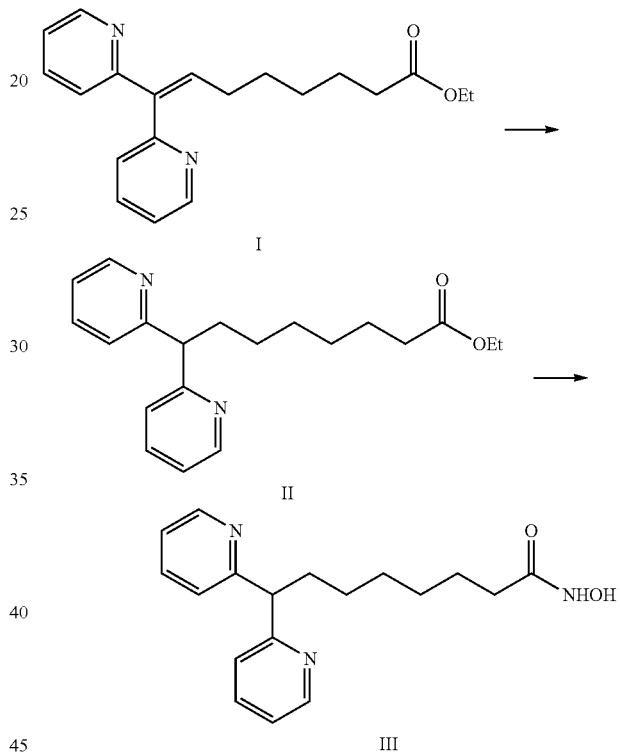

Ethyl 8,8-bis(pyridin-2-yl)octanoate (II)

NaBH$_4$ (43 mg, 1.14 mmol) and NiCl$_2$.6H$_2$O (135 mg, 0.57 mmol) were added to I (124 mg, 0.38 mmol, preparation of which is outlined above in Example 5) in THF (4 mL) at 0° C. under Ar(g). After 2 h of stirring at 0° C. the reaction was carefully quenched with 1N HCl (2 mL), then neutralized with saturated NaHCO$_3$, and EtOAc (10 mL) was added. The phases were separated and the aqueous phase was extracted with EtOAc (10 mL). The organic phases were combined, dried over MgSO$_4$, filtered, and then evaporated under reduced pressure. The resulting residue was purified by silica gel column chromatography eluting with hexane/EtOAc (20:80) to furnish II as a colourless oil (34 mg, 27%).
$^1$H NMR (400 MHz, CDCl$_3$) $\delta_H$: 8.59-8.50 (m, 2H), 7.65 (t, J=7.5 Hz, 2H), 7.45 (m, 2H), 7.20-7.12 (m, 2H), 4.46-4.33 (m, 1H), 4.11 (q, J=7.0 Hz, 2H), 2.29-2.22 (m, 4H), 1.57 (quin, J=7.5 Hz, 2H), 1.39-1.31 (m, 2H), 1.30-1.19 (m, 5H).
MW: 326.43. LCMS (ES). found 327.2 [MH]$^+$.

N-Hydroxy-8,8-di(pyridin-2-yl)oct-7-enamide (III)

HONH$_2$ (50% aqueous, 1 mL) was added to II (34 mg, 0.1 mmol) in MeOH (1 mL) at rt. The reaction mixture was stirred for 48 h, after which the solvents were evaporated under reduced pressure. The resulting residue was dissolved and co-evaporated with toluene (2×5 mL) then was purified by silica gel column chromatography eluting with CH$_2$Cl$_2$/MeOH (100:3 to 100:5) to furnish III as a colourless oil (16 mg, 52%).

$^1$H NMR (400 MHz, CDCl$_3$) $\delta_H$: 8.55 (d, J=4.5 Hz, 2H), 7.67 (dt, J=2.0, 7.5 Hz, 2H), 7.45 (d, J=7.5 Hz, 2H), 7.18 (ddd, J=1.0, 5.0, 7.5 Hz, 2H), 4.45 (t, J=8.0 Hz, 1H), 2.23 (quin, J=7.5 Hz, 4H), 1.64 (quin, J=6.9 Hz, 2H), 1.42-1.21 (m, 6H). MW: 313.39. LCMS (ES). found 314.2 [MH]$^+$.

EXAMPLE 7

N-Hydroxy-7-((4-methylpyridin-2-yl)(pyridin-2-yl)amino)heptanamide

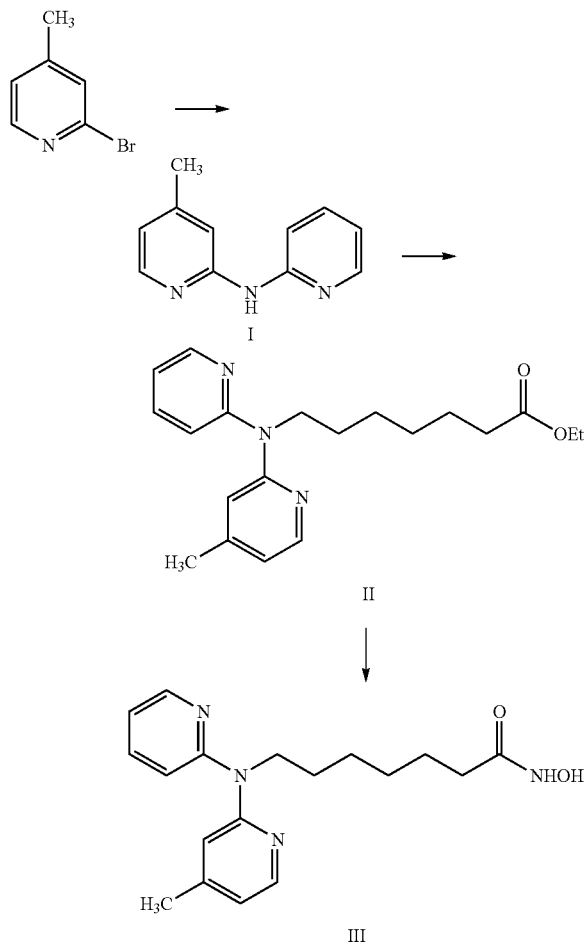

(4-Methyl-pyridin-2-yl)-pyridin-2-yl-amine (I)

2-Bromo-4-methylpyridine (0.195 mL, 1.74 mmol), 2-aminopyridine (180 mg, 1.91 mmol), potassium tert-butoxide (293 mg, 2.61 mmol), (±)-BINAP (4.3 mg, 6.96 mmol) and Pd$_2$(dba)$_3$ (4 mg, 4.35 mmol) were stirred in toluene (2.5 mL) at 90° C. under Ar(g). After 17 h stirring, the reaction mixture was diluted with CH$_2$Cl$_2$ (2.5 mL) and silica was added. The solvent was removed under reduced pressure and the resulting dry loaded material purified by silica gel column chromatography eluting with CH$_2$Cl$_2$/MeOH (100:1 to 100:2) to furnish I as a yellow solid (249 mg, 77%).

$^1$H NMR (400 MHz, CDCl$_3$) $\delta_H$: 8.27 (d, J=4.5 Hz, 1H), 8.12 (d, J=5.0 Hz, 1H), 7.64-7.54 (m, 2H), 7.36 (s, 1H), 6.85 (t, J=6.3 Hz, 1H), 6.70 (d, J=5.5 Hz, 1H), 2.34 (s, 3H). MW: 185.23. LCMS (ES). found 186.1 [MH]$^+$.

7-[(4-Methyl-pyridin-2-yl)-pyridin-2-yl-amino]heptanoic acid ethyl ester (II)

NaH (53 mg, 1.34 mmol) was added to 1 (249 mg, 1.34 mmol) in DMF (5 mL) at rt. After 10 min, KI (335 mg, 2.02 mmol) and ethyl 7-bromoheptanoate (0.40 mL, 2.02 mmol) were added, and the reaction mixture was stirred at 90° C. for 22 h. Aqueous 0.1M Na$_2$S$_2$O$_3$ (50 mL) and EtOAc (50 mL) were added, the phases were separated, and the aqueous phase was extracted with EtOAc (2×25 mL). The organic phases were combined, dried over MgSO$_4$, filtered, and subsequently evaporated under reduced pressure. The resulting residue was purified by silica gel column chromatography eluting with hexane/EtOAc (90:10 to 75:25) to furnish II as a colourless oil (101 mg, 22%).

$^1$H NMR (400 MHz, CDCl$_3$) $\delta_H$: 8.33 (dd, J=1.8, 4.8 Hz, 1H), 8.21 (d, J=5.5 Hz, 1H), 7.53-7.45 (m, 1H), 7.02 (d, J=8.5 Hz, 1H), 6.89 (s, 1H), 6.82 (dd, J=5.0, 7.0 Hz, 1H), 6.71 (d, J=5.0 Hz, 1H), 4.18-4.08 (m, 4H), 2.31-2.23 (m, 5H), 1.69 (quin, J=7.3 Hz, 2H), 1.60 (quin, J=7.3 Hz, 2H), 1.41-1.29 (m, 4H), 1.24 (t, J=7.0 Hz, 3H). MW: 341.25. LCMS (ES). found 342.2 [MH]$^+$.

N-Hydroxy-7-((4-methylpyridin-2-yl)(pyridin-2-yl)amino)heptanamide (III)

HONH$_2$ (50% aqueous, 2 mL) was added to II (101 mg, 0.3 mmol) in MeOH (2 mL) at rt. The reaction mixture was stirred for 72 h, after which the solvents were evaporated under reduced pressure. The resulting residue was dissolved and co-evaporated with toluene (2×5 mL) then was purified by silica gel column chromatography eluting with CH$_2$Cl$_2$/MeOH (100:3 to 100:7) to furnish III as a colourless oil (46 mg, 47%).

$^1$H NMR (400 MHz, CDCl$_3$) $\delta_H$: 8.31 (dd, J=1.5, 5.0 Hz, 1H), 8.20 (d, J=5.0 Hz, 1H), 7.53-7.46 (m, 1H), 6.98 (d, J=8.5 Hz, 1H), 6.86 (s, 1H), 6.83 (dd, J=5.0, 7.0 Hz, 1H), 6.72 (d, J=4.5 Hz, 1H), 4.09 (t, J=7.5 Hz, 2H), 2.26 (s, 3H), 2.11-2.03 (m, 2H), 1.69-1.52 (m, 4H), 1.38-1.23 (m, 4H). MW: 328.41. LCMS (ES). found 329.2 [MH]$^+$.

EXAMPLE 8

N-Hydroxy-7-((4-phenylpyridin-2-yl)(pyridin-2-yl)amino)heptanamide

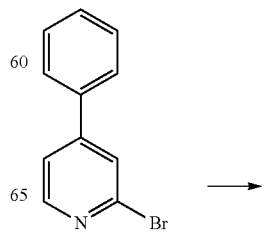

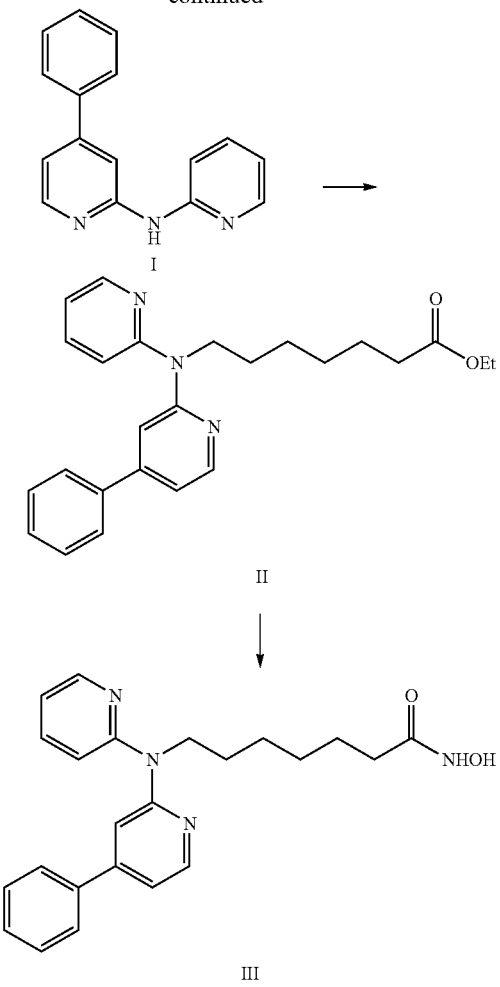

(4-Phenyl-pyridin-2-yl)-pyridin-2-yl-amine (I)

2-Bromo-4-phenylpyridine (280 mg, 1.19 mmol), 2-aminopyridine (124 mg, 1.31 mmol), potassium tert-butoxide (201 mg, 1.79 mmol), (±)-BINAP (3 mg, 0.05 mmol) and $Pd_2(dba)_3$ (2.7 mg, 0.03 mmol) were stirred in toluene (2.5 mL) at 90° C. under Ar(g). After 17 h stirring, the reaction mixture was diluted with $CH_2Cl_2$ (2.5 mL) and silica was added. The solvent was removed under reduced pressure and the resulting dry loaded material purified by silica gel column chromatography, eluting with $CH_2Cl_2$/MeOH (100:2), to furnish I as a yellow solid (183 mg, 62%).

$^1$H NMR (400 MHz, $CDCl_3$) $\delta_H$: 8.29 (t, J=5.8 Hz, 2H), 7.91-7.78 (m, 1H), 7.72-7.58 (m, 4H), 7.54-7.39 (m, 3H), 7.12 (d, J=4.5 Hz, 1H), 6.94-6.85 (m, 1H). MW: 247.29 LCMS (ES). found 248.1. [MH]$^+$.

7-[(4-Phenyl-pyridin-2-yl)-pyridin-2-yl-amino]-heptanoic acid ethyl ester (II)

NaH (29 mg, 0.73 mmol) was added to I (180 mg, 0.73 mmol) in DMF (7.5 mL) at rt. After 10 min, KI (183 mg, 1.1 mmol) and ethyl 7-bromoheptanoate (0.21 mL, 1.1 mmol) were added, and the reaction mixture was stirred at 90° C. for 16 h. Aqueous 0.1M $Na_2S_2O_3$ (50 mL) and EtOAc (30 mL) were added, the phases were separated, and the aqueous phase was extracted with EtOAc (30 mL). Then the organic phases were combined, dried over $MgSO_4$, filtered, and subsequently evaporated under reduced pressure. The resulting residue was purified by silica gel column chromatography eluting with hexane/EtOAc (85:15 to 80:20) to furnish II as a colourless oil (169 mg, 57%).

$^1$H NMR (400 MHz, $CDCl_3$) $\delta_H$: 8.40 (d, J=5.5 Hz, 1H), 8.37 (dd, J=1.0, 5.0 Hz, 1H), 7.59-7.50 (m, 3H), 7.48-7.37 (m, 3H), 7.28 (s, 1H), 7.13 (d, J=8.5 Hz, 1H), 7.09 (dd, J=1.5, 5.0 Hz, 1H), 6.87 (dd, J=5.0, 6.5 Hz, 1H), 4.23 (t, J=7.5 Hz, 2H), 4.11 (q, J=7.0 Hz, 2H), 2.27 (t, J=7.5 Hz, 2H), 1.75 (quin, J=7.4 Hz, 2H), 1.61 (quin, J=7.5 Hz, 2H), 1.44-1.31 (m, 4H), 1.24 (t, J=7.3 Hz, 3H). MW: 403.52. LCMS (ES). found 404.2 [MH]$^+$.

N-Hydroxy-7-((4-phenylpyridin-2-yl)(pyridin-2-yl)-amino)heptanamide (III)

$HONH_2$ (50% aqueous, 4 mL) was added to II (120 mg, 0.3 mmol) in MeOH (4 mL) and DMF (2 mL) at rt. The reaction mixture was stirred for 24 h, after which the solvents were evaporated under reduced pressure. The resulting residue was dissolved and co-evaporated with toluene (3×5 mL) then was purified by silica gel column chromatography eluting with $CH_2Cl_2$/MeOH (100:2 to 100:8) to furnish III as a yellow oil (28 mg, 23%).

$^1$H NMR (400 MHz, $CDCl_3$) $\delta_H$: 8.38 (d, J=5.5 Hz, 1H), 8.36 (d, J=5.0 Hz, 1H), 7.61-7.48 (m, 3H), 7.47-7.35 (m, 3H), 7.23 (br. s., 1H), 7.14-7.03 (m, 2H), 6.88 (dd, J=5.5, 6.5 Hz, 1H), 4.27-3.97 (m, 2H), 2.16-1.96 (m, 2H), 1.78-1.65 (m, 2H), 1.64-1.54 (m, 2H), 1.44-1.13 (m, 4H). MW: 390.48. LCMS (ES). found 391.2 [MH]$^+$.

EXAMPLE 9

N-Hydroxy-7-((5-methylpyridin-2-yl)(pyridin-2-yl)amino)heptanamide

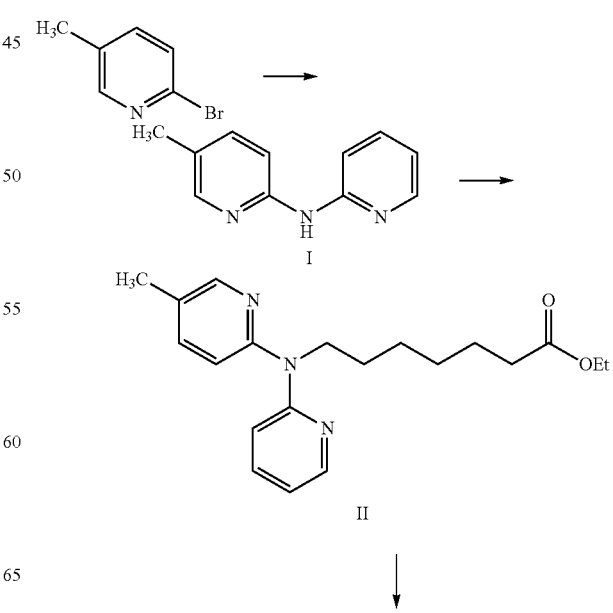

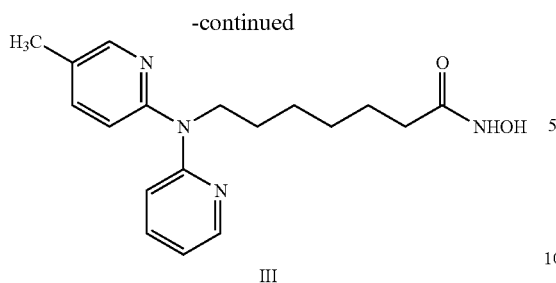

III

(5-Methyl-pyridin-2-yl)-pyridin-2-yl-amine (I)

2-Bromo-5-methylpyridine (300 mg, 1.74 mmol), 2-aminopyridine (180 mg, 1.91 mmol), potassium tert-butoxide (293 mg, 2.61 mmol), (±)-BINAP (4.3 mg, 0.07 mmol) and $Pd_2(dba)_3$ (4 mg, 0.05 mmol) were stirred in toluene (4 mL) at 90° C. under Ar(g). After 17 h stirring, the reaction was diluted with $CH_2Cl_2$ (5 mL), and silica was added. The solvent was removed under reduced pressure and the resulting dry loaded material purified by silica gel column chromatography eluting with $CH_2Cl_2$/MeOH (100:2) to furnish I as a yellow solid (187 mg, 58%).

$^1$H NMR (400 MHz, $CDCl_3$) $\delta_H$: 8.24 (d, J=4.5 Hz, 1H), 8.08 (s, 1H), 7.64-7.55 (m, 1H), 7.54-7.43 (m, 3H), 6.88-6.80 (m, 1H), 2.28 (s, 3H). MW: 185.23. LCMS (ES). found 186.1 [MH]$^+$.

7-[(5-Methyl-pyridin-2-yl)-pyridin-2-yl-amino]heptanoic acid ethyl ester (II)

NaH (38 mg, 1.0 mmol) was added to I (187 mg, 1.0 mmol) in DMF (7.5 mL) at rt. After 10 min, KI (250 mg, 1.5 mmol) and ethyl 7-bromoheptanoate (0.29 mL, 1.5 mmol) were added, and the reaction mixture was stirred at 90° C. for 17 h. Aqueous 0.1M $Na_2S_2O_3$ (30 mL) and EtOAc (25 mL) were added, the phases were separated, and the aqueous phase was extracted with EtOAc (25 mL). Then the organic phases were combined, dried over $MgSO_4$, filtered, and subsequently evaporated under reduced pressure. The resulting residue was purified by silica gel column chromatography eluting with $CH_2Cl_2$/MeOH (100:1) to furnish II as a colourless oil (236 mg, 70%). MW: 341.45. LCMS (ES). found 342.2 [MH]$^+$.

N-Hydroxy-7-((5-methylpyridin-2-yl)(pyridin-2-yl)amino)heptanamide (III)

$HONH_2$ (50% aqueous, 1 mL) was added to II (50 mg, 0.15 mmol) in MeOH (1 mL) and DMF (0.5 mL) at rt. The reaction mixture was stirred for 72 h, after which the solvents were evaporated under reduced pressure. The resulting residue was dissolved and co-evaporated with toluene (3×5 mL) then was purified by silica gel column chromatography eluting with $CH_2Cl_2$/MeOH (100:2 to 100:8) to furnish III as a pale brown oil (37 mg, 75%).

$^1$H NMR (400 MHz, $CDCl_3$) $\delta_H$: 0.28 (d, J=4.5 Hz, 1H), 8.20 (br. s., 1H), 7.50-7.43 (m, 1H), 7.41 (dd, J=1.5, 8.0 Hz, 1H), 7.03 (d, J=8.5 Hz, 1H), 6.89 (d, J=8.5 Hz, 1H), 6.78 (dd, J=5.3, 6.8 Hz, 1H), 4.16-4.03 (m, 2H), 2.29 (s, 3H), 2.16-2.00 (m, 2H), 1.80-1.52 (m, J=7.0, 10.5 Hz, 4H), 1.42-1.23 (m, 4H). MW: 328.41. LCMS (ES). found 329.2 [MH]$^+$.

EXAMPLE 10

7-((5-(Benzyloxy)pyridin-2-yl)(pyridin-2-yl)amino)-N-hydroxyheptanamide

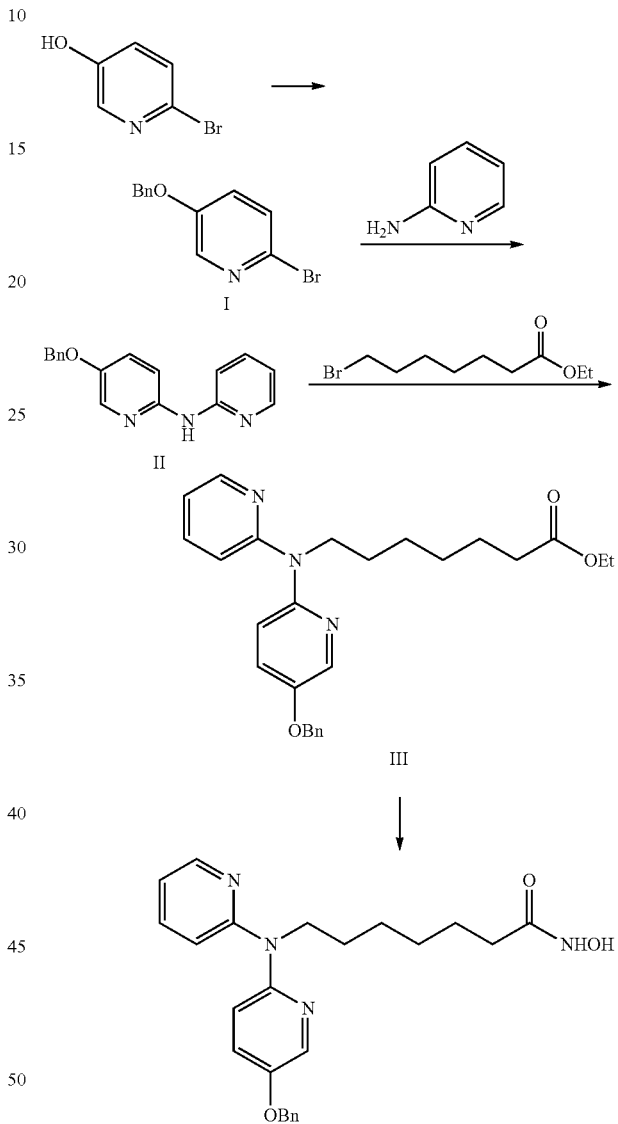

5-Benzyloxy-2-bromo-pyridine (I)

2-Bromo-5-hydroxypyridine (347 mg, 2 mmol) in DMF (3 mL) was added dropwise over a period of 10 min to a suspension of NaH (88 mg, 2.3 mmol) in DMF (2 mL) at 0° C. under Ar(g). The reaction mixture was then stirred at it for 10 min, after which it was again cooled down at 0° C., and benzyl bromide (0.25 mL, 2.1 mmol) was added. The reaction mixture was stirred at it for 2.5 h, after which it was poured onto brine (20 mL) and EtOAc (20 mL) was added. The phases were separated and the aqueous phase was extracted with EtOAc (20 mL). The organic phases were combined, dried over MgSO₄, filtered and subsequently evaporated under reduced pressure. The resulting residue was purified by silica gel column chromatography eluting with hexane/EtOAc (95:5 to 90:10) to furnish I as a colourless oil (380 mg, 72%).

¹H NMR (400 MHz, CDCl₃) δ$_H$: 8.14 (d, J=3.5 Hz, 1H), 7.46-7.29 (m, 6H), 7.16 (dd, J=3.3, 8.8 Hz, 1H), 5.10 (s, 2H). MW: 264.12. LCMS (ES). found 265.0 [MH]⁺.

(5-Benzyloxy-pyridin-2-yl)-pyridin-2-yl-amine (II)

Compound I (370 mg, 1.40 mmol), 2-aminopyridine (145 mg, 1.54 mmol), tBuOK (235 mg, 2.10 mmol), (±)-BINAP (35 mg, 0.01 mmol) and Pd₂(dba)₃ (32 mg, 0.006 mmol) were stirred in toluene (5 mL) at 90° C. under Ar(g) for 17 h. The reaction mixture was then diluted with CH₂Cl₂ (5 mL), and silica was added followed by the removal of the solvent under reduced pressure. The resulting dry loaded material was purified by silica gel column chromatography eluting with hexane/EtOAc (60:40 then 50:50) to furnish II as a colourless oil (355 mg, 91%).

¹H NMR (400 MHz, CDCl₃) δ$_H$: 8.22 (dd, J=1.8, 4.8 Hz, 1H), 8.03 (d, J=3.5 Hz, 1H), 7.62-7.53 (m, 2H), 7.46-7.28 (m, 7H), 6.81 (dd, J=5.0, 7.0 Hz, 1H), 5.09 (s, 2H). MW: 277.32. LCMS (ES). found 278.1 [MH]⁺.

7-[(5-Benzyloxy-pyridin-2-yl)-pyridin-2-yl-amino]-heptanoic acid ethyl ester (III)

NaH (48 mg, 1.26 6 mmol) was added to II (350 mg, 1.26 mmol) in DMF (6 mL) at rt. After 10 min, KI (314 mg, 1.89 mmol) and ethyl 7-bromoheptanoate (0.370 mL, 1.89 mmol) were added. The reaction mixture was stirred at 90° C. for 18 h30 after which 0.1 M Na₂S₂O₃ (50 mL) and EtOAc (50 mL) were added, the phases were separated and the aqueous extracted with EtOAc (2×25 mL). The organic phases were combined then dried over MgSO₄, filtered, and subsequently evaporated under reduced pressure. The resulting residue was purified by silica gel column chromatography eluting with hexane/EtOAc (80:20 then 70:30) to furnish III as a colourless oil (308 mg, 56%).

¹H NMR (400 MHz, CDCl₃) δ$_H$: 8.25 (dd, J=1.5, 5.0 Hz, 1H), 8.19 (d, J=3.0 Hz, 1H), 7.47-7.33 (m, 6H), 7.26 (dd, J=3.0, 8.5 Hz, 1H), 7.13 (d, J=9.0 Hz, 1H), 6.77 (d, J=8.0 Hz, 1H), 6.71 (dd, J=5.3, 6.8 Hz, 1H), 5.11 (s, 2H), 4.16-4.04 (m, 4H), 2.27 (t, J=7.5 Hz, 2H), 1.72-1.65 (m, 2H), 1.61 (quin, J=7.5 Hz, 2H), 1.42-1.29 (m, 4H), 1.25 (t, J=7.0 Hz, 3H). MW: 433.54. LCMS (ES). found 434.2 [MH]⁺.

7-((5-(Benzyloxy)pyridin-2-yl)(pyridin-2-yl)amino)-N-hydroxyheptanamide (IV)

HONH₂ (50% aqueous, 0.5 mL) was added to III (26 mg, 0.06 mmol) in DMF (0.2 mL) and MeOH (0.5 mL) at rt. The reaction mixture was stirred for 72 h, after which the solvents were evaporated under reduced pressure. The resulting residue was dissolved and co-evaporated with toluene (2×10 mL) then was purified by silica gel column chromatography eluting with CH₂Cl₂/MeOH (100:4 to 100:8) to furnish IV as a colourless oil (18.66 mg, 74%).

¹H NMR (400 MHz, CDCl₃) δ$_H$: 8.29-8.23 (m, 1H), 8.22-8.17 (m, 1H), 7.49-7.33 (m, 6H), 7.29 (dd, J=1.8, 8.8 Hz, 1H), 7.12 (d, J=8.5 Hz, 1H), 6.78-6.69 (m, 2H), 5.12 (s, 2H), 4.15-4.01 (m, 2H), 2.18-2.10 (m, 2H), 1.71-1.58 (m, 4H), 1.43-1.30 (m, 4H). MW: 420.50. LCMS (ES). found 421.2 [MH]⁺.

EXAMPLE 11

N-Hydroxy-7-((5-methoxypyridin-2-yl)(pyridin-2-yl)amino)heptanamide

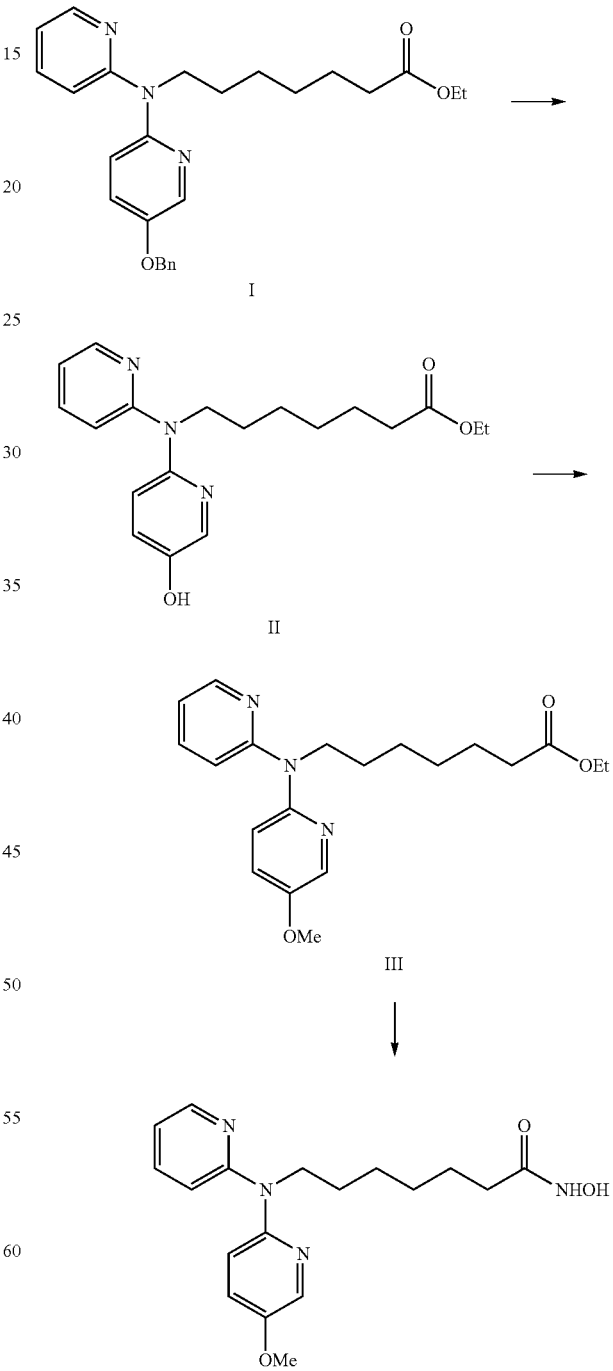

7-[(5-Hydroxy-pyridin-2-yl)-pyridin-2-yl-amino]-heptanoic acid ethyl ester (II)

Pd(OH)$_2$ (42 mg, 0.06 mmol), 1,4-cyclohexadiene (0.112 mL, 1.2 mmol) and I (105 mg, 0.24 mmol, preparation of which is outlined above in Example 10) were stirred in EtOH$_{abs}$ (5 mL) at 80° C. for 3 h. The reaction mixture was then filtered through silica and subsequently evaporated under reduced pressure. The resulting residue was purified by silica gel column chromatography eluting with hexane/EtOAc (60:40 to 40:60) to furnish II as a colourless oil (75 mg, 91%).

$^1$H NMR (400 MHz, CDCl$_3$) $\delta_H$: 8.17 (d, J=4.5 Hz, 1H), 7.96-7.92 (m, 1H), 7.52-7.45 (m, 1H), 7.09-7.02 (m, 1H), 6.99 (d, J=8.5 Hz, 1H), 6.75-6.69 (m, 2H), 4.12 (q, J=7.0 Hz, 2H), 3.95 (t, J=7.5 Hz, 2H), 2.26 (t, J=7.5 Hz, 2H), 1.66 (quin, J=7.5 Hz, 2H), 1.58 (quin, J=7.5 Hz, 2H), 1.39-1.28 (m, 4H), 1.25 (t, J=7.3 Hz, 3H). MW: 343.42. LCMS (ES). found 344.1 [MH]$^+$.

7-[(5-Methoxy-pyridin-2-yl)-pyridin-2-yl-amino] heptanoic acid ethyl ester (III)

K$_2$CO$_3$ (12 mg, 0.087 mmol) was added to compound II (20 mg, 0.058 mmol) in DMF (2 mL) at it under Ar(g). After 15 min CH$_3$I (0.004 mL, 0.058 mmol) was added and the reaction was stirred at 50° C. for 3 h30. Brine (15 mL) and EtOAc (15 mL) were added, then the phases were separated, and the aqueous phase was extracted with EtOAc (2×5 mL). The organic phases were combined then dried over MgSO$_4$, filtered, and subsequently evaporated under reduced pressure. The resulting residue was purified by silica gel column chromatography eluting with hexane/EtOAc (80:20 then 70:30) to furnish III as a colourless oil (11.65 mg, 56%).

$^1$H NMR (400 MHz, CDCl$_3$) $\delta_H$: 8.28 (d, J=4.5 Hz, 1H), 8.17 (d, J=2.5 Hz, 1H), 7.52-7.44 (m, 1H), 7.26-7.22 (m, J=2.0 Hz, 1H), 7.15 (d, J=9.0 Hz, 1H), 6.78-6.73 (m, 1H), 6.71 (d, J=8.5 Hz, 1H), 4.11 (q, J=7.0 Hz, 2H), 3.89 (s, 3H), 2.26 (t, J=7.5 Hz, 2H), 1.70 (quin, J=7.5 Hz, 2H), 1.60 (quin, J=7.5 Hz, 2H), 1.45-1.30 (m, 4H), 1.25 (t, J=7.3 Hz, 3H). MW: 357.45. LCMS (ES). found 358.1 [MH]$^+$.

7-[(5-Methoxy-pyridin-2-yl)-pyridin-2-yl-amino] heptanoic acid hydroxyamide (IV)

HONH$_2$ (50% aqueous, 2 mL) was added to III (11.65 mg, 0.033 mmol) in DMF (0.5 mL) and MeOH (2 mL) at rt. The reaction mixture was stirred for 28 h, after which the solvents were evaporated under reduced pressure. The resulting residue was dissolved and co-evaporated with toluene (2×10 mL) then was purified by silica gel column chromatography eluting with CH$_2$Cl$_2$/MeOH (100:4 then 100:6) to furnish IV as a colourless oil (6.76 mg, 60%).

$^1$H NMR (400 MHz, CDCl$_3$) $\delta_H$: 8.23 (dd, J=1.8, 5.3 Hz, 1H), 8.13 (d, J=3.5 Hz, 1H), 7.45-7.37 (m, 1H), 7.23 (dd, J=3.0, 8.5 Hz, 1H), 7.12 (d, J=8.5 Hz, 1H), 6.74-6.66 (m, 2H), 4.05 (t, J=7.5 Hz, 2H), 3.87 (s, 3H), 2.12 (t, J=7.0 Hz, 2H), 1.69-1.54 (m, 4H), 1.39-1.30 (m, J=3.5 Hz, 4H). MW: 344.41. LCMS (ES). found 345.1 [MH]$^+$.

EXAMPLE 12

N-Hydroxy-7-((5-phenylpyridin-2-yl)(pyridin-2-yl)amino)heptanamide

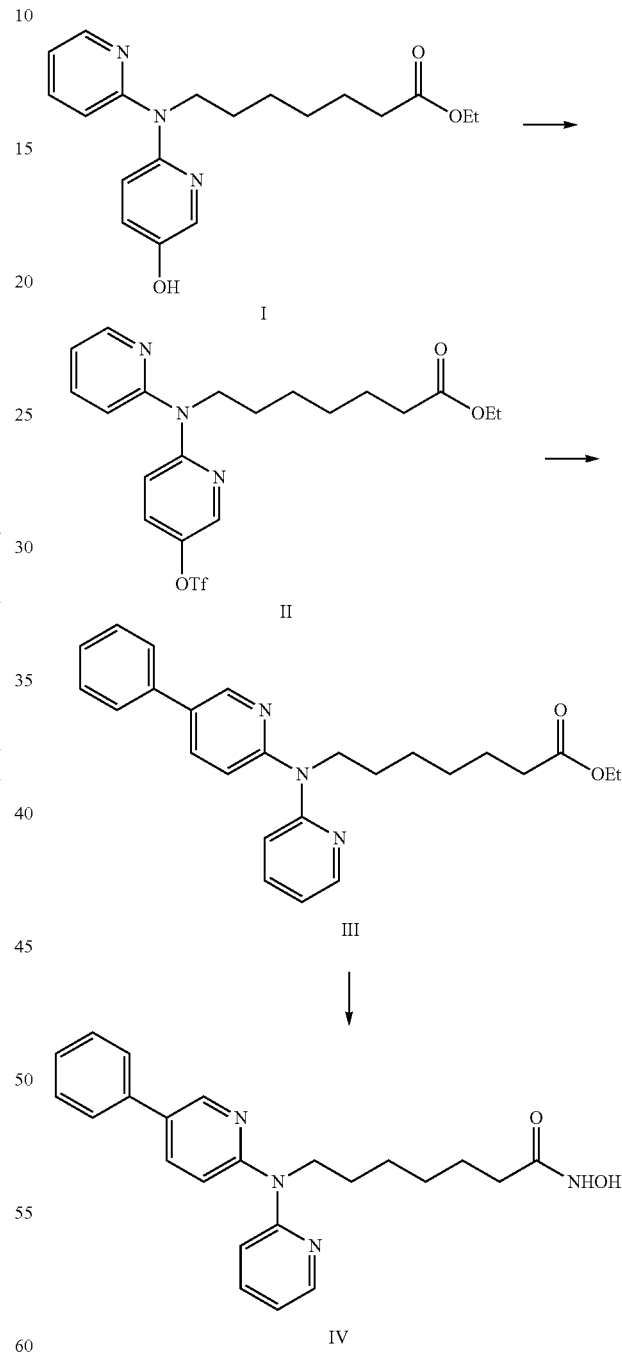

7-[Pyridin-2-yl-(5-trifluoromethanesulfonyloxy-pyridin-2-yl)-amino]-heptanoic acid ethyl ester (II)

TEA (27 µL, 0.2 mmol) and N-phenyl-bis(trifluoromethanesulfonimide) (50 mg, 0.14 mmol) were added to I (44 mg, 0.13 mmol, preparation of which is outlined above in Example 11) in CH$_2$Cl$_2$ (2 mL) at rt under Ar(g). After 17 h stirring, the reaction mixture was evaporated under reduced pressure and the resulting residue was purified by silica gel column chromatography eluting with hexane/EtOAc (95:5 to 75:25) to furnish II as a colourless oil (53 mg, 86%).

$^1$H NMR (300 MHz, CDCl$_3$) $\delta_H$: 8.44-8.39 (m, 1H), 8.23 (d, J=2.9 Hz, 1H), 7.70-7.62 (m, 1H), 7.40-7.32 (m, 1H), 7.18 (d, J=8.1 Hz, 1H), 7.07-6.99 (m, 2H), 4.20-4.04 (m, 4H), 2.28 (t, J=7.3 Hz, 2H), 1.75-1.54 (m, 4H), 1.36 (td, J=3.5, 7.2 Hz, 4H), 1.25 (t, J=7.1 Hz, 3H). $^{19}$F NMR (282 MHz, CDCl$_3$) $\square_F$=−72.7. MW: 475.48. LCMS (ES). found 476.1 [MH]$^+$.

7-[(5-Phenyl-pyridin-2-yl)-pyridin-2-yl-amino]-heptanoic acid ethyl ester (III)

Compound II (22 mg, 0.046 mmol), Pd(PPh$_3$)$_4$ (1.6 mg, 0.0014 mmol), phenylboronic acid (11.2 mg, 0.092 mmol) and potassium carbonate (9.5 mg, 0.07 mmol) were stirred in toluene (2 mL) at 90° C. in a sealed tube for 20 h. Then the reaction mixture was filtrated through celite and evaporated under reduced pressure. The resulting residue was purified by silica gel column chromatography eluting with hexane/EtOAc (90:10 to 70:30) to furnish 16 mg of III in mixture with the starting material. MW: 403.52. LCMS (ES). found 404.2 [MH]$^+$.

7-[(5-Phenyl-pyridin-2-yl)-pyridin-2-yl-amino]-heptanoic acid hydroxyamide (IV)

HONH$_2$ (50% aqueous, 2 mL) was added the crude batch of III (16 mg) in DMF (0.5 mL) and MeOH (2 mL) at rt. The reaction mixture was stirred for 72 h, after which the solvents were evaporated under reduced pressure. The resulting residue was dissolved and co-evaporated with toluene (2×3 mL) then was purified by silica gel column chromatography eluting with CH$_2$Cl$_2$/MeOH (100:8 then 100:10) to furnish IV as a colourless oil (1.36 mg, 7% over two steps).

$^1$H NMR (400 MHz, CDCl$_3$) $\delta_H$: 8.61 (d, J=2.0 Hz, 1H), 8.39 (d, J=4.0 Hz, 1H), 7.80 (dd, J=2.0, 8.5 Hz, 1H), 7.65-7.53 (m, 3H), 7.47 (t, J=7.5 Hz, 2H), 7.41-7.33 (m, 1H), 7.15 (d, J=8.5 Hz, 1H), 7.12 (d, J=8.5 Hz, 1H), 6.97-6.90 (m, 1H), 4.23 (t, J=7.5 Hz, 2H), 2.24-2.15 (m, 2H), 1.79-1.70 (m, 2H), 1.69-1.62 (m, 2H), 1.48-1.31 (m, 4H). MW: 390.48. LCMS (ES). found 391.1 [MH]$^+$.

Example 13

7-((5-(4-Fluorophenyl)pyridin-2-yl)(pyridin-2-yl) amino)-N-hydroxyheptanamide

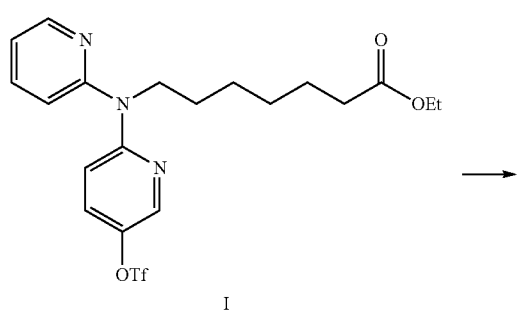

I

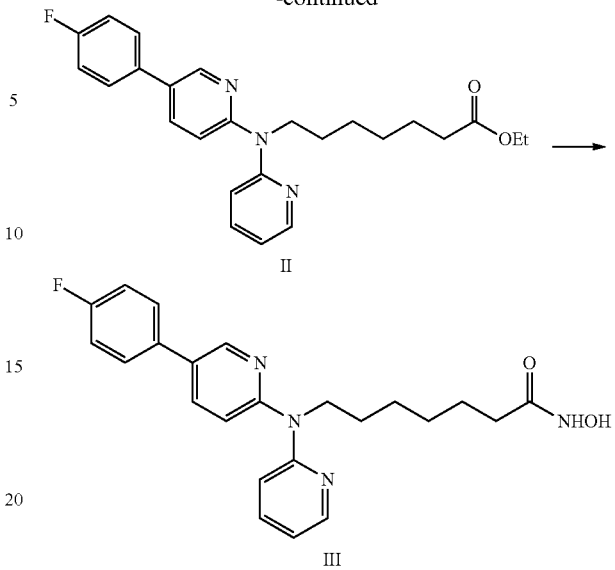

II

III

7-{[5-(4-Fluoro-phenyl)-pyridin-2-yl]-pyridin-2-yl-amino}-heptanoic acid ethyl ester (II)

Compound I (13 mg, 0.027 mmol, preparation of which is outlined above in Example 12), Pd(PPh$_3$)$_4$ (3.5 mg, 0.003 mmol), 4-fluorophenylboronic acid (7.6 mg, 0.055 mmol) and potassium carbonate (15 mg, 0.108 mmol) were stirred in toluene (1.5 mL) and water (0.7 mL) at 120° C. under microwave irradiation (300 W) for 20 min. The reaction mixture was then poured onto brine (5 mL) and extracted with EtOAc (3×5 mL). The organic phases were combined then dried over MgSO$_4$, filtered, and subsequently evaporated under reduced pressure. The resulting residue was purified by silica gel column chromatography eluting with hexane/EtOAc (90:10 then 85:15) to furnish II as a colourless oil (2.5 mg, 22%).

$^1$H NMR (300 MHz, CDCl$_3$) $\delta_H$: 8.54 (d, J=2.2 Hz, 1H), 8.38 (dd, J=1.3, 4.9 Hz, 1H), 7.70 (dd, J=2.4, 8.6 Hz, 1H), 7.62-7.45 (m, 3H), 7.20-7.07 (m, 4H), 6.91 (dd, J=5.3, 6.8 Hz, 1H), 4.27-4.19 (m, 2H), 4.12 (q, J=7.3 Hz, 2H), 2.28 (t, J=7.5 Hz, 2H), 1.80-1.68 (m, 2H), 1.68-1.56 (m, 2H), 1.46-1.31 (m, 4H), 1.25 (t, J=7.1 Hz, 3H). $^{19}$F NMR (282 MHz, CDCl$_3$) $^{19}$F=−115.7. MW: 421.51. LCMS (ES). found 422.2 [MH]$^+$.

7-((5-(4-Fluorophenyl)pyridin-2-yl)(pyridin-2-yl)-amino)-N-hydroxyheptanamide (III)

HONH$_2$ (50% aqueous, 0.5 mL) was added to II (2.5 mg, 0.006 mmol) in DMF (0.2 mL) and MeOH (0.5 mL) at rt. The reaction mixture was stirred for 72 h, after which the solvents were evaporated under reduced pressure. The resulting residue was dissolved and co-evaporated with toluene (2×2 mL) then was purified by silica gel column chromatography eluting with CH$_2$Cl$_2$/MeOH (100:6) to furnish III as a colourless oil (1.63 mg, 70%).

$^1$H NMR (400 MHz, CDCl$_3$) $\delta_H$: 8.56 (d, J=2.5 Hz, 1H), 8.41-8.36 (m, 1H), 7.74 (d, J=8.0 Hz, 1H), 7.62 (t, J=6.3 Hz, 1H), 7.53 (dd, J=5.3, 8.3 Hz, 2H), 7.19-7.08 (m, 4H), 6.98-6.92 (m, J=4.0 Hz, 1H), 4.23 (t, J=7.0 Hz, 2H), 2.23-2.11 (m, 2H), 1.82-1.59 (m, 4H), 1.47-1.29 (m, 4H). MW: 408.47. LCMS (ES). found 409.2 [MH]$^+$.

EXAMPLE 14

7-(Isoquinolin-3-yl-pyridin-2-yl-amino)-heptanoic acid hydroxyamide

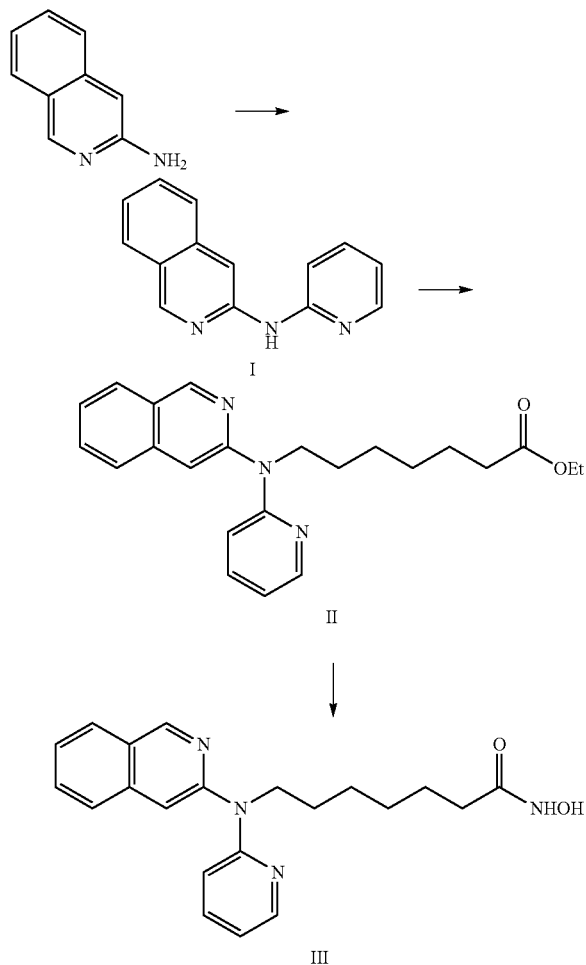

Isoquinolin-3-yl-pyridin-2-yl-amine (I)

2-Amino-isoquinoline (301 mg, 2.09 mmol), 2-bromopyridine (181 μL, 1.90 mmol), tBuOK (320 mg, 2.55 mmol), (±)-BINAP (47 mg, 0.08 mmol) and Pd$_2$(dba)$_3$ (43 mg, 0.05 mmol) were stirred in toluene (3 mL) at 90° C. under Ar(g) for 17 h. The reaction mixture was then diluted with CH$_2$Cl$_2$ (5 mL) and silica was added followed by the removal of the solvent under reduced pressure. The resulting dry loaded material was purified by silica gel column chromatography eluting with hexane/EtOAc (80:20 then 70:30) to furnish I as a white solid (252 mg, 60%).

$^1$H NMR (400 MHz, CDCl$_3$) δ$_H$: 8.99 (s, 1H), 8.34 (d, J=4.0 Hz, 1H), 8.28 (s, 1H), 7.87 (d, J=8.5 Hz, 1H), 7.78 (d, J=8.5 Hz, 1H), 7.67-7.55 (m, 2H), 7.39 (t, J=7.5 Hz, 1H), 7.19 (d, J=7.5 Hz, 1H), 6.91-6.84 (m, 1H). MW: 221.26. LCMS (ES). found 222.1 [MH]$^+$.

7-(Isoquinolin-3-yl-pyridin-2-yl-amino)-heptanoic acid ethyl ester (II)

NaH (44 mg, 1.13 mmol) was added to I (250 mg, 1.13 mmol) in DMF (6 mL) at rt. After 10 min, KI (282 mg, 1.70 mmol) and ethyl 7-bromoheptanoate (0.330 mL, 1.70 mmol) were added. The reaction mixture was stirred at 90° C. for 18 h after which 0.1 M Na$_2$S$_2$O$_3$ (50 mL) and EtOAc (50 mL) were added, the phases were separated and the aqueous extracted with EtOAc (50 mL). The organic phases were combined then dried over MgSO$_4$, filtered, and subsequently evaporated under reduced pressure. The resulting residue was purified by silica gel column chromatography eluting with hexane/EtOAc (90:10 then 80:20) to furnish II as a colourless oil (221 mg, 52%).

$^1$H NMR (400 MHz, CDCl$_3$) δ$_H$: 9.13 (s, 1H), 8.36-8.29 (m, 1H), 7.92 (d, J=8.0 Hz, 1H), 7.71-7.65 (m, 1H), 7.61 (t, J=7.3 Hz, 1H), 7.51-7.39 (m, 3H), 6.93 (d, J=8.5 Hz, 1H), 6.77 (dd, J=5.5, 6.5 Hz, 1H), 4.25 (t, J=7.5 Hz, 2H), 4.11 (q, J=7.0 Hz, 2H), 2.26 (t, J=7.5 Hz, 2H), 1.79-1.71 (m, 2H), 1.66-1.52 (m, 2H), 1.46-1.30 (m, 4H), 1.24 (t, J=7.3 Hz, 3H). MW: 377.48. LCMS (ES). found 378.2 [MH]$^+$.

7-(Isoquinolin-3-yl-pyridin-2-yl-amino)-heptanoic acid hydroxyamide (III)

HONH$_2$ (50% aqueous, 1 mL) was added to II (40 mg, 0.1 mmol) in DMF (0.5 mL) and MeOH (1 mL) at rt. The reaction mixture was stirred for 72 h, after which the solvents were evaporated under reduced pressure. The resulting residue was dissolved and co-evaporated with toluene (2×2 mL) then was purified by silica gel column chromatography eluting with CH$_2$Cl$_2$/MeOH (100:3 to 100:8) to furnish III as a colourless oil (19 mg, 54%).

$^1$H NMR (400 MHz, CDCl$_3$) δ$_H$: 9.15 (s, 1H), 8.32 (d, J=4.5 Hz, 1H), 7.95 (d, J=8.0 Hz, 1H), 7.72 (d, J=8.5 Hz, 1H), 7.65 (t, J=7.5 Hz, 1H), 7.54-7.42 (m, 3H), 6.85 (d, J=8.5 Hz, 1H), 6.80 (dd, J=5.5, 7.0 Hz, 1H), 4.24 (t, J=7.5 Hz, 2H), 2.16 (t, J=6.8 Hz, 2H), 1.73 (quin, J=7.0 Hz, 2H), 1.64 (quin, J=6.0 Hz, 2H), 1.47-1.29 (m, 4H). MW: 364.44. LCMS (ES). found 365.1 [MH]$^+$.

Example 15

7-[(4-Benzyloxy-pyridin-2-yl)-pyridin-2-yl-amino]-heptanoic acid hydroxyamide

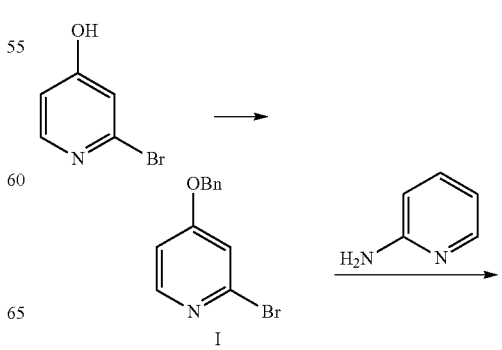

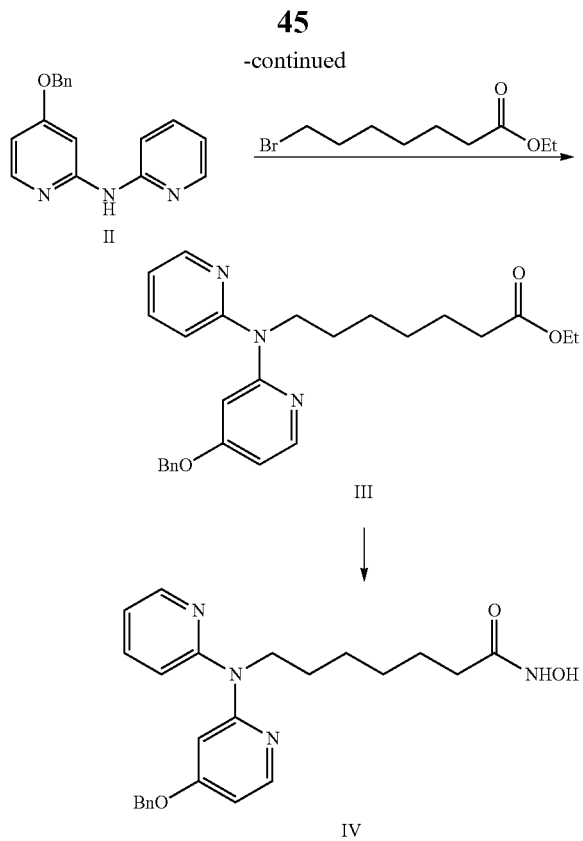
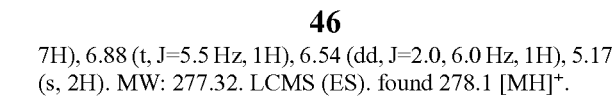

4-Benzyloxy-2-bromo-pyridine (I)

NaH (761 mg, 19.83 mmol) was added portion wise to 2-bromo-4-hydroxypyridine (3 g, 17.24 mmol) in DMF (50 mL) at 0° C. under Ar(g). Then the reaction mixture was stirred at rt for 10 min after which it was again cooled down at 0° C. and benzyl bromide (2.15 mL, 18.10 mmol) was added. The reaction was stirred at it for 4 h, after which it was poured onto brine (200 mL) and EtOAc (200 mL) was added. The phases were separated and the organic phase was dried over MgSO$_4$, filtered and subsequently evaporated under reduced pressure. The resulting residue was purified by silica gel column chromatography eluting with hexane/EtOAc (90:10 to 80:20) to furnish I as a white solid (2.331 g, 51%).

$^1$H NMR (400 MHz, CDCl$_3$) δ$_H$: 8.05 (d, J=6.0 Hz, 1H), 7.31-7.20 (m, 4H), 7.13 (s, 1H), 6.95 (d, J=2.5 Hz, 1H), 6.71 (dd, J=2.5, 6.0 Hz, 1H), 4.97 (s, 2H). MW: 264.12. LCMS (ES). found 265.9 [MH]$^+$.

(4-Benzyloxy-pyridin-2-yl)-pyridin-2-yl-amine (II)

Compound I (2.325 mg, 8.80 mmol), 2-aminopyridine (911 mg, 9.68 mmol), tBuOK (1.481 g, 13.20 mmol), (±)-BINAP (219 mg, 0.35 mmol) and Pd$_2$(dba)$_3$ (201 mg, 0.22 mmol) were stirred in toluene (35 mL) at 90° C. under Ar(g) for 17 h. The reaction mixture was then diluted with CH$_2$Cl$_2$ (20 mL) and silica was added followed by the removal of the solvent under reduced pressure. The resulting dry loaded material was purified by silica gel column chromatography eluting with hexane/EtOAc (60:40 then 50:50) to furnish II as a yellow oil (1.773 g, 73%).

$^1$H NMR (400 MHz, CDCl$_3$) δ$_H$: 8.26 (dd, J=1.5, 5.0 Hz, 1H), 8.08-7.96 (m, 1H), 7.61 (t, J=6.8 Hz, 1H), 7.51-7.32 (m, 7H), 6.88 (t, J=5.5 Hz, 1H), 6.54 (dd, J=2.0, 6.0 Hz, 1H), 5.17 (s, 2H). MW: 277.32. LCMS (ES). found 278.1 [MH]$^+$.

7-[(4-Benzyloxy-pyridin-2-yl)-pyridin-2-yl-amino] heptanoic acid ethyl ester (III)

NaH (245 mg, 6.38 mmol) was added to II (1.77 g, 6.38 mmol) in DMF (25 mL) at rt. After 15 min, KI (1.588 g, 9.57 mmol) and ethyl 7-bromoheptanoate (1.86 mL, 9.57 mmol) were added, and the reaction mixture was stirred at 90° C. for 17 h. Aqueous 0.1M Na$_2$S$_2$O$_3$ (100 mL) and EtOAc (100 mL) were added and the phases were separated. The organic phase was washed with brine (100 mL), dried over MgSO$_4$, filtered, and subsequently evaporated under reduced pressure. The resulting residue was purified by silica gel column chromatography eluting with hexane/EtOAc (90:10 to 70:30) to furnish III as a yellow oil (1.321 g, 48%).

$^1$H NMR (400 MHz, CDCl$_3$) δ$_H$: 8.34 (dd, J=2.0, 5.0 Hz, 1H), 8.18 (d, J=6.0 Hz, 1H), 7.49-7.43 (m, 1H), 7.42-7.31 (m, 5H), 7.01 (d, J=8.5 Hz, 1H), 6.84 (dd, J=5.3, 6.8 Hz, 1H), 6.60 (d, J=2.0 Hz, 1H), 6.53 (dd, J=2.3, 5.8 Hz, 1H), 5.04 (s, 2H), 4.18-4.05 (m, 4H), 2.26 (t, J=7.5 Hz, 2H), 1.72-1.55 (m, 4H), 1.41-1.30 (m, 4H), 1.25 (t, J=7.0 Hz, 3H). MW: 433.54. LCMS (ES). found 434.2 [MH]$^+$.

7-[(4-Benzyloxy-pyridin-2-yl)-pyridin-2-yl-amino]-heptanoic acid hydroxyamide (IV)

HONH$_2$ (50% aqueous, 1 mL) was added to III (47 mg, 0.11 mmol) in DMF (0.2 mL) and MeOH (0.5 mL) at rt. The reaction mixture was stirred for 72 h, after which the solvents were evaporated under reduced pressure. The resulting residue was dissolved and co-evaporated with toluene (2×2 mL) then was purified by silica gel column chromatography eluting with CH$_2$Cl$_2$/MeOH (100:5) to furnish IV as a colourless oil (19 mg, 41%).

$^1$H NMR (400 MHz, CDCl$_3$) δ$_H$: 8.35 (dd, J=1.5, 5.0 Hz, 1H), 8.18 (d, J=5.5 Hz, 1H), 7.53-7.45 (m, 1H), 7.42-7.30 (m, 5H), 6.99 (d, J=8.5 Hz, 1H), 6.89 (dd, J=5.0, 7.0 Hz, 1H), 6.57 (dd, J=2.3, 5.8 Hz, 1H), 6.54 (d, J=2.0 Hz, 1H), 5.04 (s, 2H), 4.12 (t, J=7.5 Hz, 2H), 2.14 (t, J=6.8 Hz, 2H), 1.70-1.59 (m, 4H), 1.41-1.26 (m, 4H). MW: 420.50. LCMS (ES). found 421.2 [MH]$^+$.

Example 16

7-[(4-Methoxy-pyridin-2-yl)-pyridin-2-yl-amino]-heptanoic acid hydroxyamide

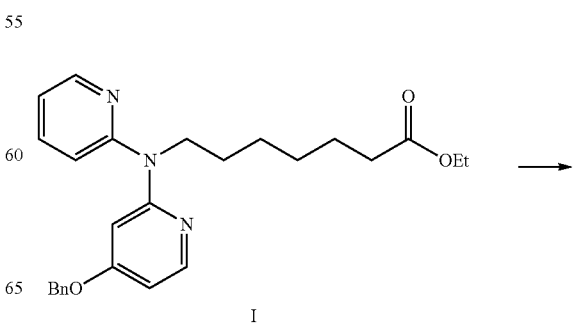

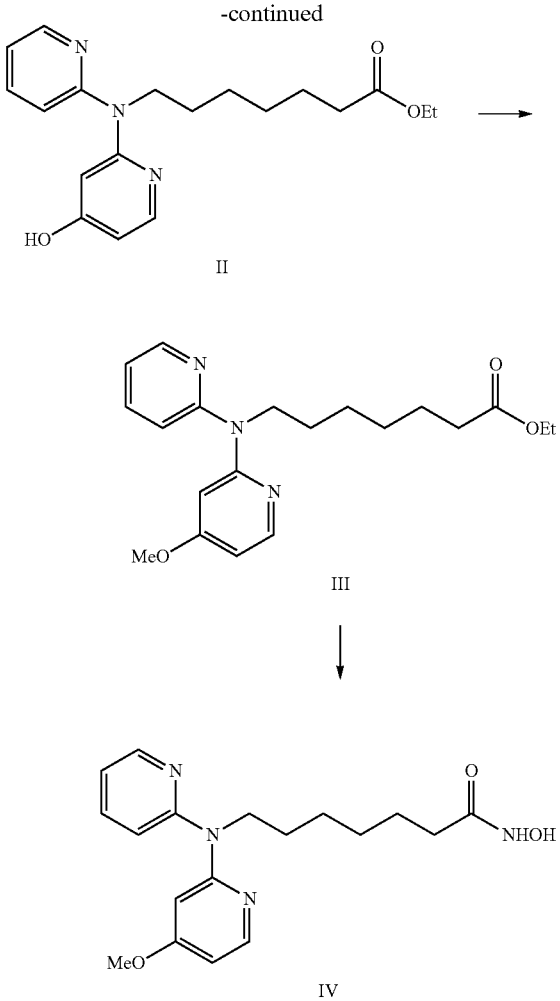

7-[(4-Hydroxy-pyridin-2-yl)-pyridin-2-yl-amino]-heptanoic acid ethyl ester (II)

Pd(OH)₂ (515 mg, 0.72 mmol), 1,4-cyclohexadiene (1.37 mL, 14.69 mmol) and compound I (1.274 g, 2.94 mmol, prepared using the method outlined above in Example 15) were stirred in EtOH$_{abs}$ (25 mL) at 80° C. for 2.5 h. Then the reaction mixture was filtered through silica and subsequently evaporated under reduced pressure. The resulting residue was purified by silica gel column chromatography eluting with CH₂Cl₂/MeOH (100:3 to 100:10) to furnish II as a colourless oil (728 mg, 72%).

¹H NMR (400 MHz, CDCl₃) δ$_H$: 8.30 (dd, J=1.5, 5.0 Hz, 1H), 7.75-7.67 (m, 1H), 7.59 (d, J=7.0 Hz, 1H), 7.03 (d, J=8.5 Hz, 1H), 6.98 (dd, J=5.3, 6.8 Hz, 1H), 6.40 (dd, J=2.0, 6.5 Hz, 1H), 6.28 (s, 1H), 4.13 (q, J=7.2 Hz, 2H), 3.89 (t, J=7.5 Hz, 2H), 2.30 (t, J=7.5 Hz, 2H), 1.79 (quin, J=7.5 Hz, 2H), 1.64 (quin, J=7.2 Hz, 2H), 1.46-1.32 (m, 4H), 1.27 (t, J=7.5 Hz, 3H). MW: 343.42. LCMS (ES). found 344.1 [MH]⁺.

7-[(4-Methoxy-pyridin-2-yl)-pyridin-2-yl-amino]-heptanoic acid ethyl ester (III)

K₂CO₃ (15 mg, 0.11 mmol) was added to II (25 mg, 0.073 mmol) in DMF (2 mL) at rt under Ar(g). After 15 min CH₃I (5 μL, 0.073 mmol) was added and the reaction was stirred at 70° C. for 22 h. Brine (30 mL) and EtOAc (30 mL) were added, then the phases were separated, and the aqueous phase was extracted with EtOAc (2×20 mL). The organic phases were combined then dried over MgSO₄, filtered, and subsequently evaporated under reduced pressure. The resulting residue was purified by silica gel column chromatography eluting with hexane/EtOAc (60:40) to furnish III as a colourless oil (10 mg, 40%).

¹H NMR (400 MHz, CDCl₃) δ$_H$: 8.37 (d, J=3.5 Hz, 1H), 8.20 (d, J=6.0 Hz, 1H), 7.54 (t, J=7.3 Hz, 1H), 7.10 (d, J=8.5 Hz, 1H), 6.93-6.84 (m, 1H), 6.53 (s, 1H), 6.48 (dd, J=2.3, 5.8 Hz, 1H), 4.17 (t, J=7.5 Hz, 2H), 4.12 (q, J=7.0 Hz, 2H), 3.79 (s, 3H), 2.27 (t, J=7.5 Hz, 2H), 1.70 (quin, J=7.5 Hz, 2H), 1.60 (quin, J=7.5 Hz, 2H), 1.42-1.31 (m, 4H), 1.25 (t, J=7.0 Hz, 3H). MW: 357.45. LCMS (ES). found 358.2 [MH]⁺.

7-[(4-Methoxy-pyridin-2-yl)-pyridin-2-yl-amino] heptanoic acid hydroxyamide (IV)

HONH₂ (50% aqueous, 2 mL) was added to III (10 mg, 0.028 mmol) in DMF (0.5 mL) and MeOH (2 mL) at rt. The reaction mixture was stirred for 17 h, after which the solvents were evaporated under reduced pressure. The resulting residue was dissolved and co-evaporated with toluene (2×2 mL) then was purified by silica gel column chromatography eluting with CH₂Cl₂/MeOH (100:3 to 100:10) to furnish IV as a colourless oil (8 mg, 84%).

¹H NMR (400 MHz, MeOD) δ$_H$: 8.26 (dd, J=2.0, 5.0 Hz, 1H), 8.09 (d, J=6.0 Hz, 1H), 7.68-7.62 (m, 1H), 7.05 (d, J=8.0 Hz, 1H), 6.98-6.92 (m, 1H), 6.65 (dd, J=2.5, 6.0 Hz, 1H), 6.58 (d, J=2.0 Hz, 1H), 4.07 (t, J=7.5 Hz, 2H), 3.82 (s, 3H), 2.06 (t, J=7.0 Hz, 2H), 1.66 (quin, J=8.0 Hz, 2H), 1.57 (quin, J=7.0 Hz, 2H), 1.41-1.30 (m, 4H). MW: 344.41. LCMS (ES). found 345.1 [MH]⁺.

EXAMPLE 17

7-[(4-Ethoxy-pyridin-2-yl)-pyridin-2-yl-amino]-heptanoic acid hydroxyamide

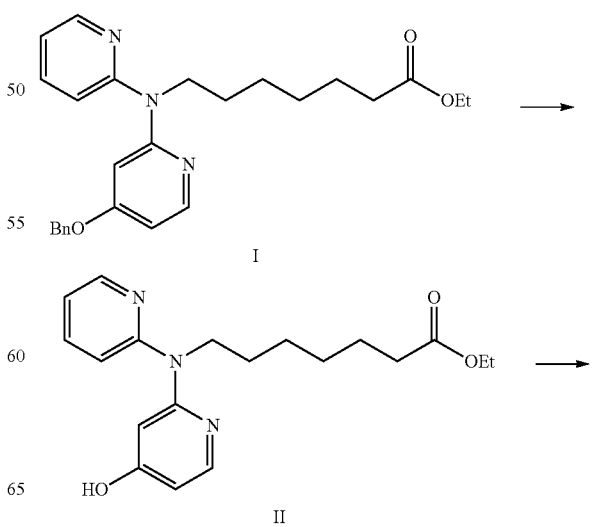

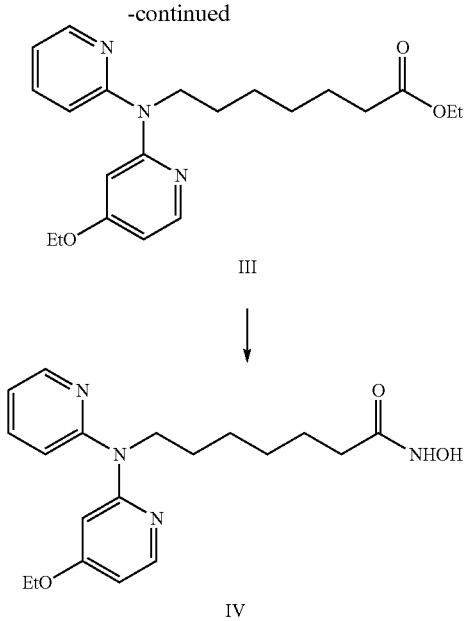

7-[(4-Hydroxy-pyridin-2-yl)-pyridin-2-yl-amino]-heptanoic acid ethyl ester (II)

Pd(OH)$_2$ (515 mg, 0.72 mmol), 1,4-cyclohexadiene (1.37 mL, 14.69 mmol) and compound I (1.274 g, 2.94 mmol, prepared using the method outlined above in Example 15) were stirred in EtOH$_{abs}$ (25 mL) at 80° C. for 2.5 h. Then the reaction mixture was filtered through silica and subsequently evaporated under reduced pressure. The resulting residue was purified by silica gel column chromatography eluting with CH$_2$Cl$_2$/MeOH (100:3 to 100:10) to furnish II as a colourless oil (728 mg, 72%).

$^1$H NMR (400 MHz, CDCl$_3$) δ$_H$: 8.30 (dd, J=1.5, 5.0 Hz, 1H), 7.75-7.67 (m, 1H), 7.59 (d, J=7.0 Hz, 1H), 7.03 (d, J=8.5 Hz, 1H), 6.98 (dd, J=5.3, 6.8 Hz, 1H), 6.40 (dd, J=2.0, 6.5 Hz, 1H), 6.28 (s, 1H), 4.13 (q, J=7.2 Hz, 2H), 3.89 (t, J=7.5 Hz, 2H), 2.30 (t, J=7.5 Hz, 2H), 1.79 (quin, J=7.5 Hz, 2H), 1.64 (quin, J=7.2 Hz, 2H), 1.46-1.32 (m, 4H), 1.27 (t, J=7.5 Hz, 3H). MW: 343.42. LCMS (ES). found 344.1 [MH]$^+$.

7-[(4-Ethoxy-pyridin-2-yl)-pyridin-2-yl-amino]heptanoic acid ethyl ester (III)

K$_2$CO$_3$ (21 mg, 0.15 mmol) was added to II (31 mg, 0.10 mmol) in DMF (2 mL) at it under Ar(g). After 15 min iodoethane (9 µL, 0.11 mmol) was added and the reaction was stirred at 70° C. for 26 h. Brine (50 mL) and EtOAc (25 mL) were added, then the phases were separated, and the aqueous phase was extracted with EtOAc (25 mL). The organic phases were combined then dried over MgSO$_4$, filtered, and subsequently evaporated under reduced pressure. The resulting residue was purified by silica gel column chromatography eluting with hexane/EtOAc (60:40) to furnish III as a colourless oil (16 mg, 43%).

$^1$H NMR (400 MHz, CDCl$_3$) δ$_H$: 8.34 (dd, J=1.8, 5.3 Hz, 1H), 8.17 (d, J=5.5 Hz, 1H), 7.55-7.43 (m, 1H), 7.07 (d, J=8.5 Hz, 1H), 6.84 (dd, J=4.8, 7.3 Hz, 1H), 6.54 (d, J=2.0 Hz, 1H), 6.45 (dd, J=2.3, 5.8 Hz, 1H), 4.14 (t, J=7.5 Hz, 2H), 4.12 (q, J=7.0 Hz, 2H), 4.01 (q, J=7.0 Hz, 2H), 2.26 (t, J=7.5 Hz, 2H), 1.69 (quin, J=7.5 Hz, 2H), 1.60 (quin, J=7.3 Hz, 2H), 1.41 (t, J=7.0 Hz, 3H), 1.37-1.30 (m, 4H), 1.25 (t, J=7.3 Hz, 3H). MW: 371.47. LCMS (ES). found 372.2 [MH]$^+$.

7-[(4-Ethoxy-pyridin-2-yl)-pyridin-2-yl-amino]-heptanoic acid hydroxyamide (IV)

HONH$_2$ (50% aqueous, 2 mL) was added to III (16 mg, 0.045 mmol) in DMF (0.5 mL) and MeOH (2 mL) at rt. The reaction mixture was stirred for 17 h, after which the solvents were evaporated under reduced pressure. The resulting residue was dissolved and co-evaporated with toluene (2×2 mL) then was purified by silica gel column chromatography eluting with CH$_2$Cl$_2$/MeOH (100:3 to 100:8) to furnish IV as a colourless oil (12 mg, 75%).

$^1$H NMR (400 MHz, CDCl$_3$) δ$_H$: 8.33 (dd, J=1.8, 5.3 Hz, 1H), 8.16 (d, J=6.0 Hz, 1H), 7.55-7.47 (m, 1H), 7.02 (d, J=8.0 Hz, 1H), 6.85 (dd, J=5.0, 6.5 Hz, 1H), 6.51 (d, J=2.0 Hz, 1H), 6.48 (dd, J=2.0, 5.5 Hz, 1H), 4.10 (t, J=7.5 Hz, 2H), 4.01 (q, J=7.0 Hz, 2H), 2.10 (t, J=6.8 Hz, 2H), 1.72-1.53 (m, 4H), 1.40 (t, J=7.0 Hz, 3H), 1.36-1.25 (m, 4H). MW: 358.43. LCMS (ES). found 359.1 [MH]$^+$.

EXAMPLE 18

7-[(4-Propoxy-pyridin-2-yl)-pyridin-2-yl-amino] heptanoic acid hydroxyamide

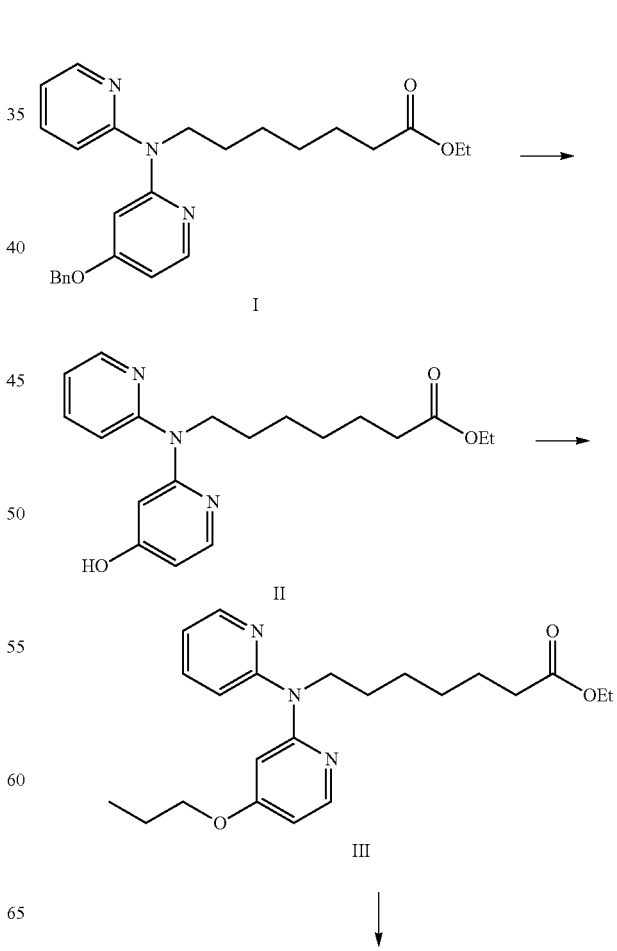

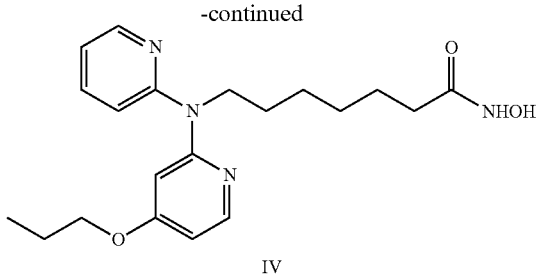

IV

7-[(4-Hydroxy-pyridin-2-yl)-pyridin-2-yl-amino] heptanoic acid ethyl ester (II)

Pd(OH)$_2$ (515 mg, 0.72 mmol), 1,4-cyclohexadiene (1.37 mL, 14.69 mmol) and I (1.274 g, 2.94 mmol, prepared using the method outlined above in Example 15) were stirred in EtOH$_{abs}$ (25 mL) at 80° C. for 2.5 h. Then the reaction mixture was filtered through silica and subsequently evaporated under reduced pressure. The resulting residue was purified by silica gel column chromatography eluting with CH$_2$Cl$_2$/MeOH (100:3 to 100:10) to furnish II as a colourless oil (728 mg, 72%).

$^1$H NMR (400 MHz, CDCl$_3$) δ$_H$: 8.30 (dd, J=1.5, 5.0 Hz, 1H), 7.75-7.67 (m, 1H), 7.59 (d, J=7.0 Hz, 1H), 7.03 (d, J=8.5 Hz, 1H), 6.98 (dd, J=5.3, 6.8 Hz, 1H), 6.40 (dd, J=2.0, 6.5 Hz, 1H), 6.28 (s, 1H), 4.13 (q, J=7.2 Hz, 2H), 3.89 (t, J=7.5 Hz, 2H), 2.30 (t, J=7.5 Hz, 2H), 1.79 (quin, J=7.5 Hz, 2H), 1.64 (quin, J=7.2 Hz, 2H), 1.46-1.32 (m, 4H), 1.27 (t, J=7.5 Hz, 3H). MW: 343.42. LCMS (ES). found 344.1 [MH]$^+$.

7-[(4-Propoxy-pyridin-2-yl)-pyridin-2-yl-amino] heptanoic acid ethyl ester (III)

K$_2$CO$_3$ (21 mg, 0.15 mmol) was added to II (31 mg, 0.10 mmol) in DMF (2 mL) at rt under Ar(g). After 15 min iodopropane (11 μL, 0.11 mmol) was added and the reaction was stirred at 70° C. for 17 h. Brine (50 mL) and EtOAc (25 mL) were added, then the phases were separated, and the aqueous phase was extracted with EtOAc (25 mL). The organic phases were combined then dried over MgSO$_4$, filtered, and subsequently evaporated under reduced pressure. The resulting residue was purified by silica gel column chromatography eluting with hexane/EtOAc (70:30) to furnish III as a colourless oil (28 mg, 80%).

$^1$H NMR (400 MHz, CDCl$_3$) δ$_H$: 8.35 (dd, J=1.5, 5.0 Hz, 1H), 8.17 (d, J=5.5 Hz, 1H), 7.55-7.46 (m, 1H), 7.07 (d, J=8.0 Hz, 1H), 6.85 (t, J=6.5 Hz, 1H), 6.54 (d, J=2.0 Hz, 1H), 6.47 (dd, J=2.0, 6.0 Hz, 1H), 4.15 (t, J=7.5 Hz, 2H), 4.11 (q, J=7.0 Hz, 2H), 3.90 (t, J=6.5 Hz, 2H), 2.26 (t, J=7.8 Hz, 2H), 1.79 (sxt, J=7.0 Hz, 2H), 1.69 (quin, J=7.4 Hz, 2H), 1.60 (quin, J=7.4 Hz, 2H), 1.43-1.29 (m, 4H), 1.26 (t, J=7.0 Hz, 3H), 1.02 (t, J=7.3 Hz, 3H). MW: 385.50. LCMS (ES). found 386.2 [MH]$^+$.

7-[(4-Propoxy-pyridin-2-yl)-pyridin-2-yl-amino] heptanoic acid hydroxyamide (IV)

HONH$_2$ (50% aqueous, 2 mL) was added to III (16 mg, 0.045 mmol) in DMF (0.5 mL) and MeOH (2 mL) at rt. The reaction mixture was stirred for 22.5 h, after which the solvents were evaporated under reduced pressure. The resulting residue was dissolved and co-evaporated with toluene (2×2 mL) then was purified by silica gel column chromatography eluting with CH$_2$Cl$_2$/MeOH (100:5 to 100:8) to furnish IV as a colourless oil (14 mg, 50%).

$^1$H NMR (400 MHz, CDCl$_3$) δ$_H$: 8.36 (d, J=3.0 Hz, 1H), 8.18 (d, J=3.5 Hz, 1H), 7.54 (t, J=7.8 Hz, 1H), 7.04 (d, J=8.5 Hz, 1H), 6.89 (t, J=5.8 Hz, 1H), 6.50 (br. s., 2H), 4.14 (t, J=6.3 Hz, 2H), 3.90 (t, J=6.5 Hz, 2H), 2.15 (br. s., 2H), 1.79 (sxt, J=6.9 Hz, 2H), 1.71-1.57 (m, 4H), 1.36 (br. s., 4H), 1.02 (t, J=7.3 Hz, 3H). MW: 372.46. LCMS (ES). found 373.2 [MH]$^+$.

EXAMPLE 19

7-[(4-Isopropoxy-pyridin-2-yl)-pyridin-2-yl-amino]-heptanoic acid hydroxyamide

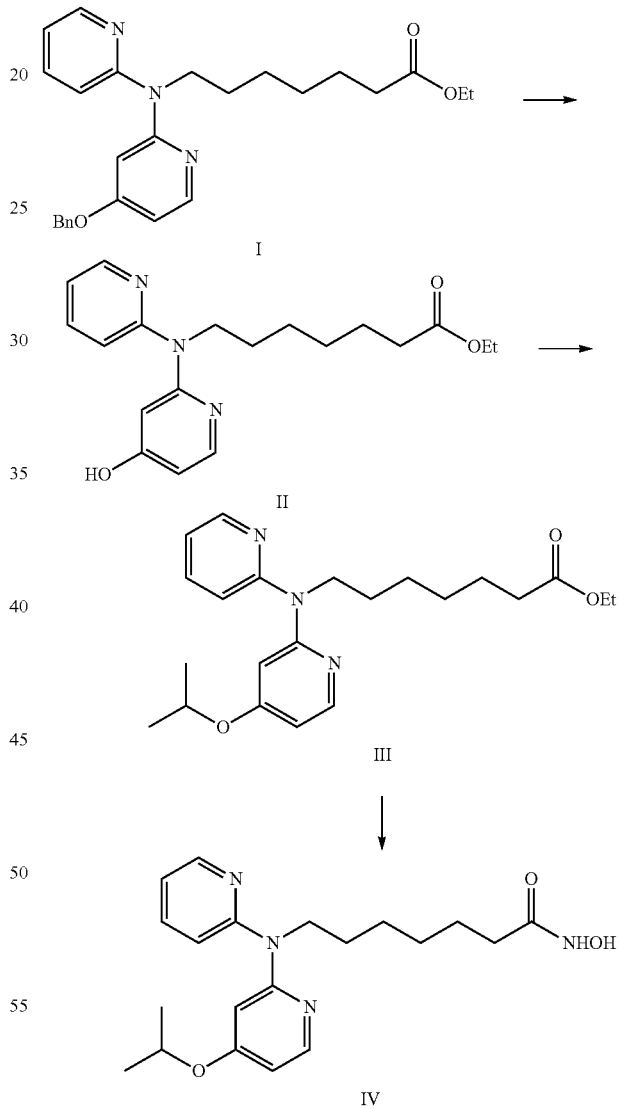

7-[(4-Hydroxy-pyridin-2-yl)-pyridin-2-yl-amino]-heptanoic acid ethyl ester (II)

Pd(OH)$_2$ (515 mg, 0.72 mmol), 1,4-cyclohexadiene (1.37 mL, 14.69 mmol) and compound I (1.274 g, 2.94 mmol, prepared using the method outlined above in Example 15) were stirred in EtOH$_{abs}$ (25 mL) at 80° C. for 2.5 h. Then the reaction mixture was filtered through silica and subsequently evaporated under reduced pressure. The resulting residue was purified by silica gel column chromatography eluting with CH$_2$Cl$_2$/MeOH (100:3 to 100:10) to furnish II as a colourless oil (728 mg, 72%).

$^1$H NMR (400 MHz, CDCl$_3$) δ$_H$: 8.30 (dd, J=1.5, 5.0 Hz, 1H), 7.75-7.67 (m, 1H), 7.59 (d, J=7.0 Hz, 1H), 7.03 (d, J=8.5 Hz, 1H), 6.98 (dd, J=5.3, 6.8 Hz, 1H), 6.40 (dd, J=2.0, 6.5 Hz, 1H), 6.28 (s, 1H), 4.13 (q, J=7.2 Hz, 2H), 3.89 (t, J=7.5 Hz, 2H), 2.30 (t, J=7.5 Hz, 2H), 1.79 (quin, J=7.5 Hz, 2H), 1.64 (quin, J=7.2 Hz, 2H), 1.46-1.32 (m, 4H), 1.27 (t, J=7.5 Hz, 3H). MW: 343.42. LCMS (ES). found 344.1 [MH]$^+$.

7[(4-Isopropoxy-pyridin-2-yl)-pyridin-2-yl-amino]-heptanoic acid ethyl ester (III)

K$_2$CO$_3$ (32 mg, 0.23 mmol) was added to II (53 mg, 0.15 mmol) in DMF (2 mL) at it under Ar(g). After 15 min 2-iodopropane (16 μL, 0.165 mmol) was added and the reaction was stirred at 70° C. for 3 h. Brine (50 mL) and EtOAc (25 mL) were added, then the phases were separated, and the aqueous phase was extracted with EtOAc (25 mL). The organic phases were combined then dried over MgSO$_4$, filtered, and subsequently evaporated under reduced pressure. The resulting residue was purified by silica gel column chromatography eluting with hexane/EtOAc (70:30) to furnish III as a colourless oil (23 mg, 40%).

$^1$H NMR (400 MHz, CDCl$_3$) δ$_H$: 8.34 (dd, J=2.0, 5.0 Hz, 1H), 8.16 (d, J=6.0 Hz, 1H), 7.54-7.47 (m, 1H), 7.06 (d, J=8.0 Hz, 1H), 6.83 (dd, J=5.3, 6.8 Hz, 1H), 6.51 (d, J=2.0 Hz, 1H), 6.44 (dd, J=2.0, 6.0 Hz, 1H), 4.53 (spt, J=6.1 Hz, 1H), 4.14 (t, J=7.5 Hz, 2H), 4.09 (q, J=7.5 Hz, 2H), 2.26 (t, J=7.5 Hz, 2H), 1.69 (quin, J=7.4 Hz, 2H), 1.60 (quin, J=7.3 Hz, 2H), 1.38-1.34 (m, 4H), 1.34 (s, 3H), 1.32 (s, 3H), 1.25 (t, J=7.0 Hz, 3H). MW: 385.50. LCMS (ES). found 386.2 [MH]$^+$.

7-[(4-Isopropoxy-pyridin-2-yl)-pyridin-2-yl-amino] heptanoic acid hydroxyamide (IV)

HONH$_2$ (50% aqueous, 2 mL) was added to III (23 mg, 0.06 mmol) in DMF (0.5 mL) and MeOH (2 mL) at rt. The reaction mixture was stirred for 26 h, after which the solvents were evaporated under reduced pressure. The resulting residue was dissolved and co-evaporated with toluene (2×2 mL) then was purified by silica gel column chromatography eluting with CH$_2$Cl$_2$/MeOH (100:5 to 100:8) to furnish IV as a colourless oil (14 mg, 65%).

$^1$H NMR (400 MHz, CDCl$_3$) δ$_H$: 8.34 (dd, J=1.8, 5.3 Hz, 1H), 8.16 (d, J=6.5 Hz, 1H), 7.55-7.47 (m, 1H), 7.02 (d, J=8.5 Hz, 1H), 6.86 (dd, J=5.3, 6.8 Hz, 1H), 6.51-6.43 (m, 2H), 4.54 (spt, J=6.0 Hz, 1H), 4.11 (t, J=7.5 Hz, 2H), 2.13 (t, J=6.5 Hz, 2H), 1.72-1.56 (m, 4H), 1.41-1.24 (m, 10H). MW: 372.46. LCMS (ES). found 373.2 [MH]$^+$.

EXAMPLE 20

7-(Pyridin-3-yl-pyridin-2-yl-amino)-heptanoic acid hydroxyamide

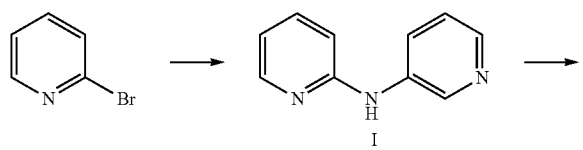

I

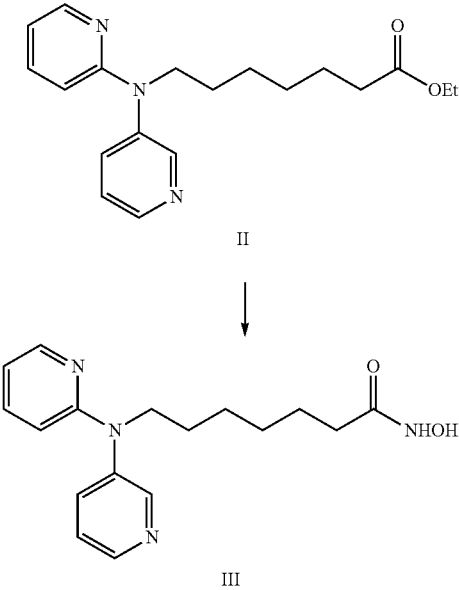

Pyridin-3-yl-pyridin-2-yl-amine (I)

2-Bromopyridine (0.3 mL, 3.16 mmol), 3-aminopyridine (327 mg, 3.48 mmol), tBuOK (532 mg, 4.74 mmol), (±)-BINAP (79 mg, 0.126 mmol) and Pd$_2$(dba)$_3$ (72 mg, 0.079 mmol) were stirred in toluene (5 mL) at 90° C. under Ar(g) for 19 h. The reaction mixture was then diluted with CH$_2$Cl$_2$ (5 mL) and silica was added followed by the removal of the solvent under reduced pressure. The resulting dry loaded material was purified by silica gel column chromatography eluting with CH$_2$Cl$_2$/MeOH (100:3 to 100:6) to furnish I as a brown oil (483 mg, 90%).

$^1$H NMR (400 MHz, MeOD) δ$_H$: 8.76 (d, J=2.5 Hz, 1H), 8.20 (ddd, J=1.5, 3.0, 8.5 Hz, 1H), 8.16 (td, J=1.2, 5.1 Hz, 1H), 8.06 (dd, J=1.5, 5.0 Hz, 1H), 7.62-7.56 (m, 1H), 7.32 (dd, J=4.3, 8.8 Hz, 1H), 6.86-6.78 (m, 2H). MW: 171.20. LCMS (ES). found 172.1 [MH]$^+$.

7-(Pyridin-3-yl-pyridin-2-yl-amino)-heptanoic acid ethyl ester (II)

NaH (107 mg, 2.8 mmol) was added to II (480 mg, 2.8 mmol) in DMF (10 mL) at rt. After 15 min, KI (697 mg, 4.2 mmol) and ethyl 7-bromoheptanoate (0.825 mL, 4.2 mmol) were added, and the reaction mixture was stirred at 90° C. for 17 h. Aqueous 0.1M Na$_2$S$_2$O$_3$ (100 mL) and EtOAc (100 mL) were added and the phases were separated. The organic phase was washed with brine (100 mL), dried over MgSO$_4$, filtered, and subsequently evaporated under reduced pressure. The resulting residue was purified by silica gel column chromatography eluting with CH$_2$Cl$_2$/MeOH (100:1 to 100:3) to furnish II as a brown oil (141 mg, 15%).

$^1$H NMR (400 MHz, CDCl$_3$) δ$_H$: 8.55 (br. s., 1H), 8.46 (br. s., 1H), 8.22 (d, J=5.0 Hz, 1H), 7.59 (d, J=8.0 Hz, 1H), 7.42-7.31 (m, 2H), 6.68 (t, J=5.8 Hz, 1H), 6.47 (d, J=8.0 Hz, 1H), 4.12 (q, J=7.0 Hz, 2H), 3.96 (t, J=7.5 Hz, 2H), 2.27 (t, J=7.5 Hz, 2H), 1.72-1.55 (m, 4H), 1.42-1.30 (m, 4H), 1.25 (t, J=7.0 Hz, 3H). MW: 327.42. LCMS (ES). found 328.2 [MH]$^+$.

7-(Pyridin-3-yl-pyridin-2-yl-amino)-heptanoic acid hydroxyamide (III)

HONH$_2$ (50% aqueous, 2 mL) was added to II (140 mg, 0.43 mmol) in DMF (0.5 mL) and MeOH (2 mL) at rt. The reaction mixture was stirred for 24 h, after which the solvents were evaporated under reduced pressure. The resulting residue was dissolved and co-evaporated with toluene (2×2 mL) then was purified by silica gel column chromatography eluting with $CH_2Cl_2$/MeOH (100:4 to 100:25) to furnish III as a yellow oil (31 mg, 23%).

$^1$H NMR (400 MHz, MeOD) $\delta_H$: 8.44 (d, J=2.5 Hz, 1H), 8.36 (dd, J=1.5, 5.0 Hz, 1H), 8.12 (ddd, J=1.0, 2.0, 5.0 Hz, 1H), 7.74 (ddd, J=1.5, 2.5, 8.0 Hz, 1H), 7.54-7.46 (m, 2H), 6.75 (dd, J=5.0, 6.5 Hz, 1H), 6.62 (d, J=8.5 Hz, 1H), 3.94 (t, J=7.5 Hz, 2H), 2.06 (t, J=7.5 Hz, 2H), 1.72-1.54 (m, 4H), 1.42-1.30 (m, 4H). MW: 314.38. LCMS (ES). found 315.1 $[MH]^+$.

EXAMPLE 21

7-{[4-(4-Fluoro-phenyl)-pyridin-2-yl]-pyridin-2-yl-amino}-heptanoic acid hydroxyamide

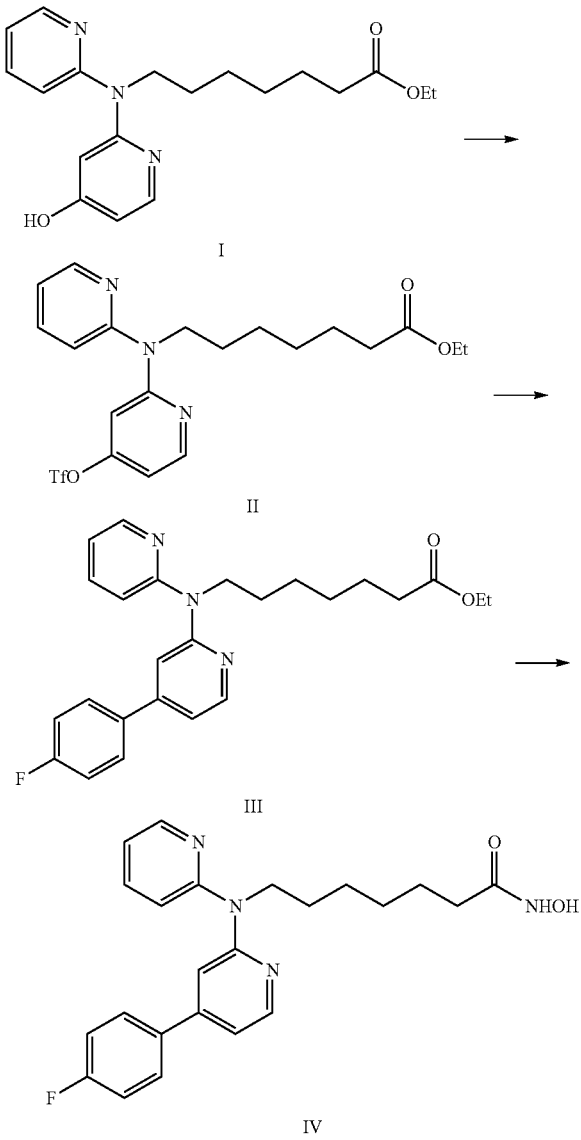

7-[(Pyridin-2-yl-(4-trifluoromethanesulfonyloxy-pyridin-2-yl)-amino]-heptanoic acid ethyl ester (II)

TEA (345 μL, 2.56 mmol) and N-phenyl-bis(trifluoromethanesulfonimide) (673 mg, 1.88 mmol) were added to I (588 mg, 1.71 mmol, prepared using the method outlined above in Example 16) in $CH_2Cl_2$ (10 mL) at rt under Ar(g). After 27 h stirring, the reaction mixture was evaporated under reduced pressure and the resulting residue was purified by silica gel column chromatography eluting with hexane/EtOAc (80:20) to furnish II as a colourless oil (653 mg, 80%).

$^1$H NMR (400 MHz, $CDCl_3$) $\delta_H$: 8.43 (dd, J=2.0, 5.0 Hz, 1H), 8.33 (d, J=5.5 Hz, 1H), 7.71-7.61 (m, 1H), 7.20 (d, J=8.0 Hz, 1H), 7.05 (ddd, J=1.0, 5.0, 7.5 Hz, 1H), 6.87 (d, J=2.5 Hz, 1H), 6.68 (dd, J=2.0, 5.5 Hz, 1H), 4.17 (t, J=7.5 Hz, 2H), 4.11 (q, J=7.5 Hz, 2H), 2.27 (t, J=7.5 Hz, 2H), 1.80-1.54 (m, 4H), 1.44-1.32 (m, 4H), 1.25 (t, J=7.5 Hz, 3H). MW: 475.48. LCMS (ES). found 476.1 $[MH]^+$.

7-{[4-(4-Fluoro-phenyl)-pyridin-2-yl]-pyridin-2-yl-amino}-heptanoic acid ethyl ester (III)

Compound II (54 mg, 0.113 mmol), $Pd(PPh_3)_4$ (13 mg, 0.011 mmol), 4-fluorophenylboronic acid (32 mg, 0.23 mmol) and potassium carbonate (63 mg, 0.45 mmol) were stirred in toluene (1.5 mL) and water (0.7 mL) at 120° C. under microwave irradiation (300 W) for 30 min. The reaction mixture was then poured onto brine (5 mL) and extracted with EtOAc (3×5 mL). The organic phases were combined then dried over $MgSO_4$, filtered, and subsequently evaporated under reduced pressure. The resulting residue was purified by silica gel column chromatography eluting with hexane/EtOAc (90:10 then 80:20) to furnish III as a colourless oil (34 mg, 71%).

$^1$H NMR (400 MHz, $CDCl_3$) $\delta_H$: 8.43-8.29 (m, 2H), 7.61-7.47 (m, 3H), 7.22 (s, 1H), 7.17-7.08 (m, J=8.5, 8.5 Hz, 3H), 7.04 (d, J=4.5 Hz, 1H), 6.89 (t, J=5.5 Hz, 1H), 4.23 (t, J=7.5 Hz, 2H), 4.11 (q, J=7.0 Hz, 2H), 2.27 (t, J=7.5 Hz, 2H), 1.74 (quin, J=7.5 Hz, 2H), 1.62 (quin, J=7.3 Hz, 2H), 1.46-1.30 (m, 4H), 1.24 (t, J=7.0 Hz, 3H). MW: 421.51. LCMS (ES). found 422.2 $[MH]^+$.

7-{[4-(4-Fluoro-phenyl)-pyridin-2-yl]-pyridin-2-yl-amino}-heptanoic acid hydroxyamide (IV)

$HONH_2$ (50% aqueous, 2 mL) was added to III (34 mg, 0.08 mmol) in DMF (0.5 mL) and MeOH (2 mL) at rt. The reaction mixture was stirred for 23 h, after which the solvents were evaporated under reduced pressure. The resulting residue was dissolved and co-evaporated with toluene (2×2 mL) then was purified by silica gel column chromatography eluting with $CH_2Cl_2$/MeOH (100:3 to 100:6) to furnish IV as a colourless oil (18 mg, 54%).

$^1$H NMR (400 MHz, $CDCl_3$) $\delta_H$: 8.43-8.36 (m, 2H), 7.65-7.57 (m, 1H), 7.56-7.49 (m, 2H), 7.21-7.07 (m, 5H), 6.95 (dd, J=5.3, 6.8 Hz, 1H), 4.22 (t, J=7.5 Hz, 2H), 2.18 (t, J=6.8 Hz, 2H), 1.73 (quin, J=7.0 Hz, 2H), 1.65 (quin, J=7.0 Hz, 2H), 1.47-1.31 (m, 4H). MW: 408.47. LCMS (ES). found 409.2 $[MH]^+$.

EXAMPLE 22

7-{([4-(4-Amino-phenyl)-pyridin-2-yl]-pyridin-2-yl-amino}-heptanoic acid hydroxyamide

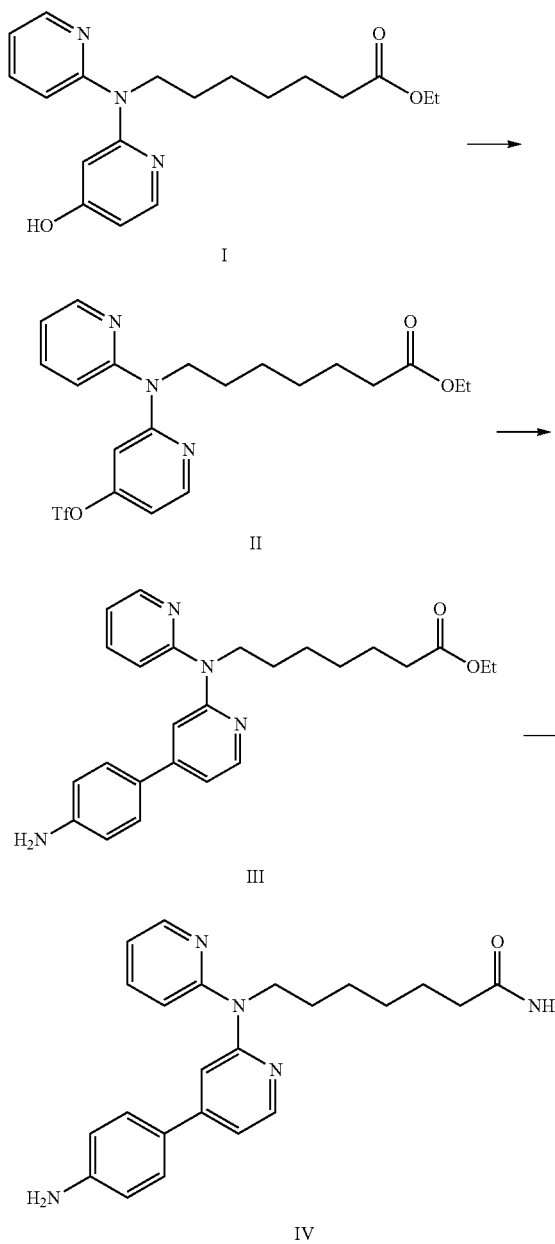

7-[Pyridin-2-yl-(4-trifluoromethanesulfonyloxy-pyridin-2-yl)-amino]-heptanoic acid ethyl ester (II)

TEA (345 μL, 2.56 mmol) and N-phenyl-bis(trifluoromethanesulfonimide) (673 mg, 1.88 mmol) were added to I (588 mg, 1.71 mmol, prepared using the method outlined above in Example 16) in CH$_2$Cl$_2$ (10 mL) at rt under Ar(g). After 27 h stirring, the reaction mixture was evaporated under reduced pressure and the resulting residue was purified by silica gel column chromatography eluting with hexane/EtOAc (80:20) to furnish II as a colourless oil (653 mg, 80%).

$^1$H NMR (400 MHz, CDCl$_3$) δ$_H$: 8.43 (dd, J=2.0, 5.0 Hz, 1H), 8.33 (d, J=5.5 Hz, 1H), 7.71-7.61 (m, 1H), 7.20 (d, J=8.0 Hz, 1H), 7.05 (ddd, J=1.0, 5.0, 7.5 Hz, 1H), 6.87 (d, J=2.5 Hz, 1H), 6.68 (dd, J=2.0, 5.5 Hz, 1H), 4.17 (t, J=7.5 Hz, 2H), 4.11 (q, J=7.5 Hz, 2H), 2.27 (t, J=7.5 Hz, 2H), 1.80-1.54 (m, 4H), 1.44-1.32 (m, 4H), 1.25 (t, J=7.5 Hz, 3H). MW: 475.48. LCMS (ES). found 476.1 [MH]$^+$.

7-{[4-(4-Amino-phenyl)-pyridin-2-yl]-pyridin-2-yl-amino}-heptanoic acid ethyl ester (III)

Compound II (52 mg, 0.109 mmol), Pd(PPh$_3$)$_4$ (12 mg, 0.011 mmol), 4-(4,4,5,5-tetramethyl-1,3,2-dioxaborolan-2-yl)aniline (48 mg, 0.218 mmol) and potassium carbonate (60 mg, 0.44 mmol) were stirred in toluene (3 mL) and water (1.5 mL) at 120° C. under microwave irradiation (300 W) for 30 min. The reaction mixture was then poured onto brine (50 mL) and extracted with EtOAc (2×20 mL). The organic phases were combined then dried over MgSO$_4$, filtered, and subsequently evaporated under reduced pressure. The resulting residue was purified by silica gel column chromatography eluting with hexane/EtOAc (90:10 then 0:100) to furnish III as a brown oil (32 mg, 70%).

$^1$H NMR (400 MHz, CDCl$_3$) δ$_H$: 8.51-8.42 (m, 1H), 8.37 (d, J=5.5 Hz, 1H), 7.72-7.57 (m, 1H), 7.51 (d, J=8.5 Hz, 1H), 7.45-7.35 (m, 2H), 7.20-7.07 (m, 3H), 6.77-6.70 (m, 2H), 4.34-4.23 (m, 2H), 4.11 (q, J=7.0 Hz, 2H), 2.27 (t, J=7.5 Hz, 2H), 1.83-1.72 (m, 2H), 1.65-1.58 (m, 2H), 1.49-1.34 (m, 4H), 1.24 (t, J=7.0 Hz, 3H). MW: 418.53. LCMS (ES). found 419.2 [MH]$^+$.

7-{[4-(4-Amino-phenyl)-pyridin-2-yl]-pyridin-2-yl-amino}-heptanoic acid hydroxyamide (IV)

HONH$_2$ (50% aqueous, 2 mL) was added to III (30 mg, 0.072 mmol) in DMF (0.5 mL) and MeOH (2 mL) at rt. The reaction mixture was stirred for 22 h, after which the solvents were evaporated under reduced pressure. The resulting residue was dissolved and co-evaporated with toluene (2×2 mL) then was purified by silica gel column chromatography eluting with CH$_2$Cl$_2$/MeOH (100:10) to furnish IV as a yellow oil (7 mg, 24%).

$^1$H NMR (400 MHz, CDCl$_3$) δ$_H$: 8.45-8.33 (m, 2H), 7.65-7.57 (m, 1H), 7.56-7.49 (m, 2H), 7.21-7.07 (m, 5H), 6.95 (dd, J=5.3, 6.8 Hz, 1H), 4.22 (t, J=7.5 Hz, 2H), 2.18 (t, J=6.8 Hz, 2H), 1.73 (quin, J=7.5 Hz, 2H), 1.65 (quin, J=7.0 Hz, 2H), 1.46-1.33 (m, 4H). MW: 405.49. LCMS (ES). found 406.2 [MH]$^+$.

EXAMPLE 23

7-[Pyridin-2-yl-(4-p-tolyl-pyridin-2-yl)-amino]-heptanoic acid hydroxyamide

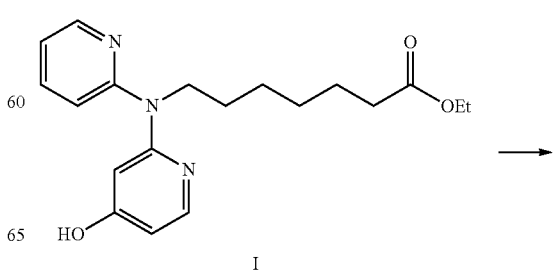

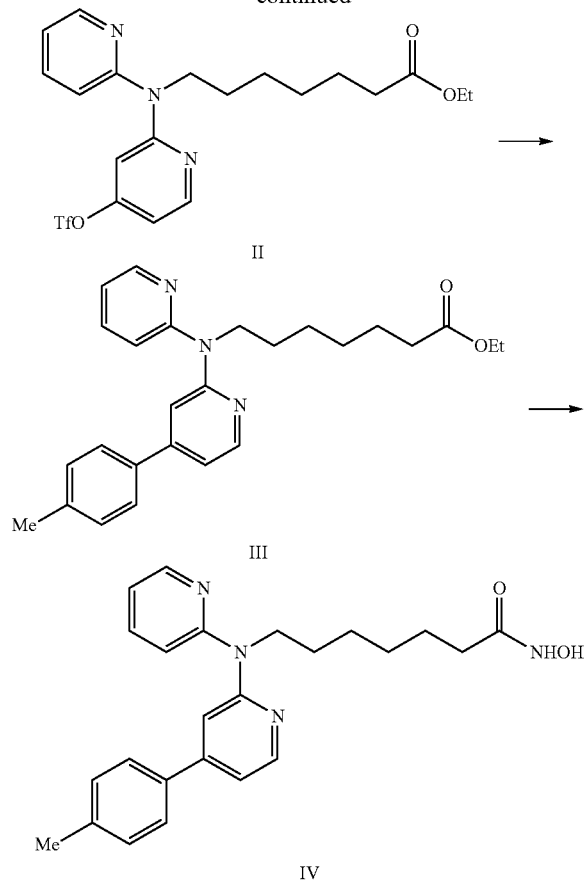

7-[Pyridin-2-yl-(4-trifluoromethanesulfonyloxy-pyridin-2-yl)-amino]-heptanoic acid ethyl ester (II)

TEA (345 µL, 2.56 mmol) and N-phenyl-bis(trifluoromethanesulfonimide) (673 mg, 1.88 mmol) were added to I (588 mg, 1.71 mmol, prepared using the method outlined above in Example 16) in $CH_2Cl_2$ (10 mL) at it under Ar(g). After 27 h stirring, the reaction mixture was evaporated under reduced pressure and the resulting residue was purified by silica gel column chromatography eluting with hexane/EtOAc (80:20) to furnish II as a colourless oil (653 mg, 80%).

$^1$H NMR (400 MHz, CDCl$_3$) $\delta_H$: 8.43 (dd, J=2.0, 5.0 Hz, 1H), 8.33 (d, J=5.5 Hz, 1H), 7.71-7.61 (m, 1H), 7.20 (d, J=8.0 Hz, 1H), 7.05 (ddd, J=1.0, 5.0, 7.5 Hz, 1H), 6.87 (d, J=2.5 Hz, 1H), 6.68 (dd, J=2.0, 5.5 Hz, 1H), 4.17 (t, J=7.5 Hz, 2H), 4.11 (q, J=7.5 Hz, 2H), 2.27 (t, J=7.5 Hz, 2H), 1.80-1.54 (m, 4H), 1.44-1.32 (m, 4H), 1.25 (t, J=7.5 Hz, 3H). MW: 475.48. LCMS (ES). found 476.1 [MH]$^+$.

7-[Pyridin-2-yl-(4-p-tolyl-pyridin-2-yl)-amino]heptanoic acid ethyl ester (III)

Compound II (56 mg, 0.117 mmol), Pd(PPh$_3$)$_4$ (12 mg, 0.011 mmol), p-tolylboronic acid (32 mg, 0.235 mmol) and potassium carbonate (65 mg, 0.47 mmol) were stirred in toluene (3 mL) and water (1.5 mL) at 120° C. under microwave irradiation (300 W) for 30 min. The reaction mixture was then poured onto brine (30 mL) and extracted with EtOAc (2×20 mL). The organic phases were combined then dried over MgSO$_4$, filtered, and subsequently evaporated under reduced pressure. The resulting residue was purified by silica gel column chromatography eluting with hexane/EtOAc (90:10 then 80:20) to furnish III as a colourless oil (43 mg, 88%).

$^1$H NMR (400 MHz, CDCl$_3$) $\delta_H$: 8.41-8.29 (m, 2H), 7.53 (t, J=7.3 Hz, 1H), 7.49-7.42 (m, 2H), 7.30-7.19 (m, 3H), 7.15-7.04 (m, 2H), 6.92-6.82 (m, 1H), 4.23 (t, J=7.5 Hz, 2H), 4.11 (q, J=7.0 Hz, 2H), 2.40 (s, 3H), 2.27 (t, J=7.5 Hz, 2H), 1.75 (quin, J=7.4 Hz, 2H), 1.62 (quin, J=7.4 Hz, 2H), 1.45-1.31 (m, 4H), 1.25 (t, J=7.0 Hz, 3H). MW: 417.54. LCMS (ES). found 418.2 [MH]$^+$.

7-[Pyridin-2-yl-(4-p-tolyl-pyridin-2-yl)-amino]heptanoic acid hydroxyamide (IV)

HONH$_2$ (50% aqueous, 2 mL) was added to III (43 mg, 0.10 mmol) in DMF (0.5 mL) and MeOH (2 mL) at rt. The reaction mixture was stirred for 17 h, after which the solvents were evaporated under reduced pressure. The resulting residue was dissolved and co-evaporated with toluene (2×2 mL) then was purified by silica gel column chromatography eluting with $CH_2Cl_2$/MeOH (100:4 to 100:7) to furnish IV as a colourless oil (16 mg, 38%).

$^1$H NMR (400 MHz, CDCl$_3$) $\delta_H$: 8.43-8.31 (m, 2H), 7.57 (t, J=7.3 Hz, 1H), 7.48-7.39 (m, 2H), 7.29-7.19 (m, 3H), 7.14 (d, J=4.5 Hz, 1H), 7.09 (d, J=8.5 Hz, 1H), 6.92 (t, J=6.0 Hz, 1H), 4.21 (t, J=7.3 Hz, 2H), 2.40 (s, 3H), 2.17 (t, J=6.3 Hz, 2H), 1.72 (quin, J=7.0 Hz, 2H), 1.65 (quin, J=6.5 Hz, 2H), 1.46-1.32 (m, 4H). MW: 404.50. LCMS (ES). found 405.2 [MH]$^+$.

EXAMPLE 24

7-[Pyridin-2-yl-(4-o-tolyl-pyridin-2-yl)-amino]-heptanoic acid hydroxyamide

-continued

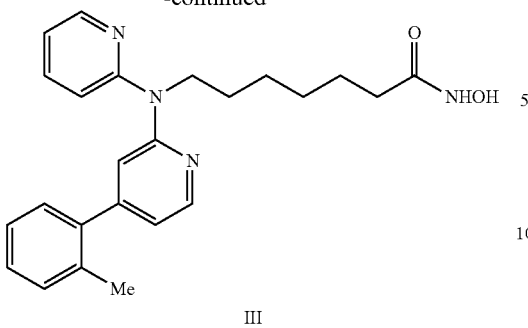

III

7-[Pyridin-2-yl-(4-o-tolyl-pyridin-2-yl)-amino]heptanoic acid ethyl ester (II)

Compound I (65 mg, 0.136 mmol, prepared using the method outlined above for Example 21), Pd(PPh₃)₄ (16 mg, 0.014 mmol), o-tolylboronic acid (37 mg, 0.273 mmol) and potassium carbonate (75 mg, 0.54 mmol) were stirred in toluene (3 mL) and water (1.5 mL) at 120° C. under microwave irradiation (300 W) for 30 min. The reaction mixture was then poured onto brine (50 mL) and extracted with EtOAc (2×20 mL). The organic phases were combined then dried over MgSO₄, filtered, and subsequently evaporated under reduced pressure. The resulting residue was purified by silica gel column chromatography eluting with hexane/EtOAc (90:10 to 80:20) to furnish II as a colourless oil (37 mg, 64%).

$^1$H NMR (400 MHz, CDCl₃) $\delta_H$: 8.40-8.32 (m, 2H), 7.58-7.47 (m, 1H), 7.32-7.18 (m, 4H), 7.14 (d, J=8.5 Hz, 1H), 6.99 (s, 1H), 6.91-6.82 (m, 2H), 4.23 (t, J=7.5 Hz, 2H), 4.12 (q, J=7.0 Hz, 2H), 2.30 (s, 3H), 2.27 (t, J=7.5 Hz, 2H), 1.75 (quin, J=7.4 Hz, 2H), 1.61 (quin, J=7.0 Hz, 2H), 1.46-1.32 (m, 4H), 1.25 (t, J=7.3 Hz, 3H). MW: 417.54. LCMS (ES). found 418.2 [MH]⁺.

7-[Pyridin-2-yl-(4-o-tolyl-pyridin-2-yl)-amino]-heptanoic acid hydroxyamide (III)

HONH₂ (50% aqueous, 2 mL) was added to II (37 mg, 0.09 mmol) in DMF (0.5 mL) and MeOH (2 mL) at rt. The reaction mixture was stirred for 22 h, after which the solvents were evaporated under reduced pressure. The resulting residue was dissolved and co-evaporated with toluene (2×2 mL) then was purified by silica gel column chromatography eluting with CH₂Cl₂/MeOH (100:4 to 100:8) to furnish III as a yellow oil (20 mg, 55%).

$^1$H NMR (400 MHz, CDCl₃) $\delta_H$: 8.41-8.33 (m, 2H), 7.57 (t, J=7.8 Hz, 1H), 7.32-7.22 (m, 3H), 7.19 (d, J=7.0 Hz, 1H), 7.12 (d, J=8.0 Hz, 1H), 6.95 (s, 1H), 6.91 (dd, J=5.5, 7.0 Hz, 1H), 6.88 (d, J=4.5 Hz, 1H), 4.21 (t, J=7.5 Hz, 2H), 2.29 (s, 3H), 2.22-2.13 (m, 2H), 1.80-1.60 (m, 4H), 1.44-1.32 (m, 4H). MW: 404.50. LCMS (ES). found 405.2 [MH]⁺.

EXAMPLE 25

7-{[4-(2-Chloro-phenyl)-pyridin-2-yl]-pyridin-2-yl-amino}-heptanoic acid hydroxyamide

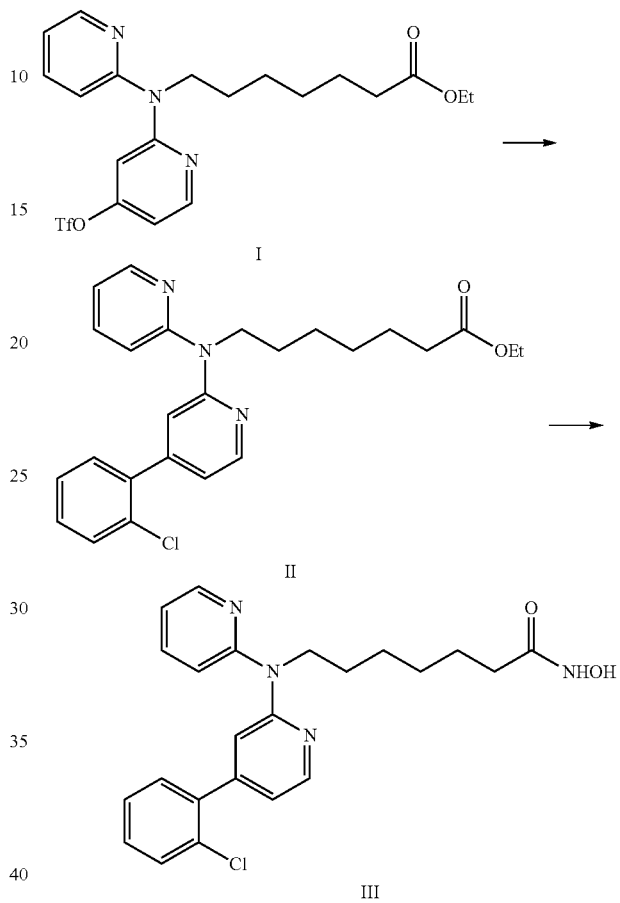

7-{[4-(2-Chloro-phenyl)-pyridin-2-yl]-pyridin-2-yl-amino}-heptanoic acid ethyl ester (II)

Compound I (55 mg, 0.116 mmol, prepared using the method outlined above for Example 21), Pd(PPh₃)₄ (14 mg, 0.012 mmol), 2-chlorophenylboronic acid (36 mg, 0.231 mmol) and potassium carbonate (64 mg, 0.46 mmol) were stirred in toluene (3 mL) and water (1.5 mL) at 120° C. under microwave irradiation (300 W) for 30 min. The reaction mixture was then poured onto brine (50 mL) and extracted with EtOAc (2×20 mL). The organic phases were combined then dried over MgSO₄, filtered, and subsequently evaporated under reduced pressure. The resulting residue was purified by silica gel column chromatography eluting with hexane/EtOAc (90:10 to 80:20) to furnish II as a colourless oil (19 mg, 38%).

$^1$H NMR (400 MHz, CDCl₃) $\delta_H$: 8.43 (d, J=5.0 Hz, 1H), 8.38 (d, J=4.0 Hz, 1H), 7.62-7.53 (m, 1H), 7.49-7.45 (m, 1H), 7.37-7.29 (m, 3H), 7.17 (d, J=8.5 Hz, 1H), 7.12 (s, 1H), 7.00-6.95 (m, 1H), 6.92-6.84 (m, 1H), 4.26 (t, J=7.3 Hz, 2H), 4.11 (q, J=7.0 Hz, 2H), 2.27 (t, J=7.5 Hz, 2H), 1.76 (quin, J=7.0 Hz, 2H), 1.61 (quin, J=7.5 Hz, 2H), 1.45-1.33 (m, 4H), 1.25 (t, J=7.0 Hz, 3H). MW: 437.96. LCMS (ES). found 438.2 [MH]⁺.

7-{[4-(2-Chloro-phenyl)-pyridin-2-yl]-pyridin-2-yl-amino}-heptanoic acid hydroxyamide (III)

HONH$_2$ (50% aqueous, 2 mL) was added to II (19 mg, 0.043 mmol) in DMF (0.5 mL) and MeOH (2 mL) at rt. The reaction mixture was stirred for 22 h, after which the solvents were evaporated under reduced pressure. The resulting residue was dissolved and co-evaporated with toluene (2×2 mL) then was purified by silica gel column chromatography eluting with CH$_2$Cl$_2$/MeOH (100:4 to 100:7) to furnish III as a pale blue oil (8 mg, 44%).

$^1$H NMR (400 MHz, CDCl$_3$) δ$_H$: 8.42 (d, J=5.5 Hz, 1H), 8.38 (d, J=4.5 Hz, 1H), 7.62-7.56 (m, 1H), 7.52-7.45 (m, 1H), 7.36-7.29 (m, 3H), 7.16 (d, J=8.5 Hz, 1H), 7.10 (s, 1H), 6.98 (d, J=4.5 Hz, 1H), 6.92 (t, J=5.5 Hz, 1H), 4.24 (t, J=7.5 Hz, 2H), 2.19 (t, J=6.8 Hz, 2H), 1.74 (quin, J=7.0 Hz, 2H), 1.65 (quin, J=7.0 Hz, 2H), 1.48-1.29 (m, 4H). MW: 424.92. LCMS (ES). found 425.1 [MH]$^+$.

EXAMPLE 26

7-{[4-(2-Fluoro-phenyl)-pyridin-2-yl]-pyridin-2-yl-amino}-heptanoic acid hydroxyamide

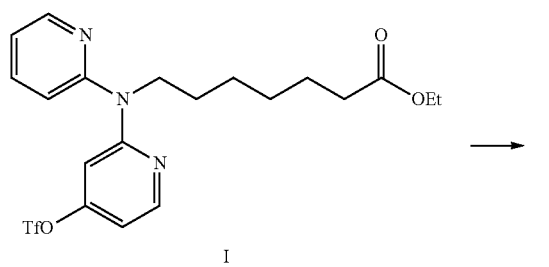

I

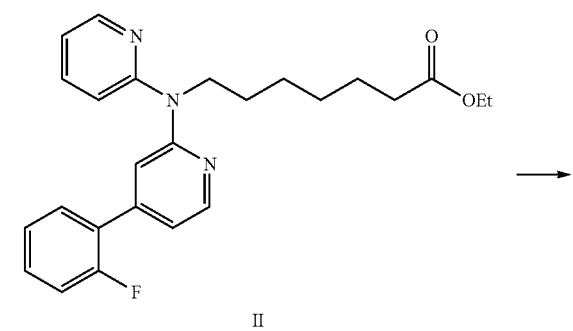

II

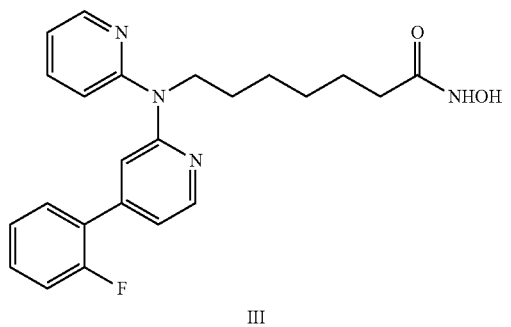

III

7-{[4-(2-Fluoro-phenyl)-pyridin-2-yl]-pyridin-2-yl-amino}-heptanoic acid ethyl ester (II)

Compound I (56 mg, 0.117 mmol, prepared using the method outlined above for Example 21), Pd(PPh$_3$)$_4$ (13 mg, 0.012 mmol), 2-fluorophenylboronic acid (33 mg, 0.235 mmol) and potassium carbonate (65 mg, 0.47 mmol) were stirred in toluene (3 mL) and water (1.5 mL) at 120° C. under microwave irradiation (300 W) for 40 min. The reaction mixture was then poured onto brine (50 mL) and extracted with EtOAc (2×20 mL). The organic phases were combined then dried over MgSO$_4$, filtered, and subsequently evaporated under reduced pressure. The resulting residue was purified by silica gel column chromatography eluting with hexane/EtOAc (90:10 to 85:15) to furnish II as a colourless oil (20 mg, 41%).

$^1$H NMR (400 MHz, CDCl$_3$) δ$_H$: 8.42 (d, J=5.5 Hz, 1H), 8.37 (dd, J=1.0, 5.0 Hz, 1H), 7.60-7.50 (m, 1H), 7.43 (dt, J=1.8, 7.7 Hz, 1H), 7.38 (tdd, J=2.6, 5.1, 10.4 Hz, 1H), 7.26-7.20 (m, 2H), 7.19-7.12 (m, 2H), 7.06 (d, J=5.0 Hz, 1H), 6.88 (dd, J=5.5, 6.5 Hz, 1H), 4.24 (t, J=7.5 Hz, 2H), 4.11 (q, J=7.4 Hz, 2H), 2.27 (t, J=7.5 Hz, 2H), 1.75 (quin, J=7.5 Hz, 2H), 1.62 (quin, J=7.5 Hz, 2H), 1.46-1.32 (m, 4H), 1.26 (t, J=7.5 Hz, 3H). MW: 421.51. LCMS (ES). found 422.2 [MH]$^+$.

7-{[4-(2-Fluoro-phenyl)-pyridin-2-yl]-pyridin-2-yl-amino}-heptanoic acid hydroxyamide (III)

HONH$_2$ (50% aqueous, 2 mL) was added to II (30 mg, 0.07 mmol) in DMF (0.5 mL) and MeOH (2 mL) at rt. The reaction mixture was stirred for 22 h, after which the solvents were evaporated under reduced pressure. The resulting residue was dissolved and co-evaporated with toluene (2×2 mL) then was purified by silica gel column chromatography eluting with CH$_2$Cl$_2$/MeOH (100:4 to 100:7) to furnish III as a white wax (15 mg, 79%).

$^1$H NMR (400 MHz, CDCl$_3$) δ$_H$: 8.41 (d, J=5.5 Hz, 1H), 8.37 (d, J=4.0 Hz, 1H), 7.61-7.54 (m, 1H), 7.42 (dt, J=1.5, 7.5 Hz, 1H), 7.40-7.35 (m, 1H), 7.25-7.19 (m, 2H), 7.19-7.10 (m, 2H), 7.08 (d, J=5.0 Hz, 1H), 6.90 (dd, J=5.3, 6.8 Hz, 1H), 4.21 (t, J=7.0 Hz, 2H), 2.15 (t, J=6.8 Hz, 2H), 1.72 (quin, J=7.5 Hz, 2H), 1.64 (quin, J=7.0 Hz, 2H), 1.44-1.31 (m, 4H). MW: 408.47. LCMS (ES). found 409.2 [MH]$^+$.

Example 27

7-[Pyridin-2-yl-(4-m-tolyl-pyridin-2-yl)-amino]-heptanoic acid hydroxyamide

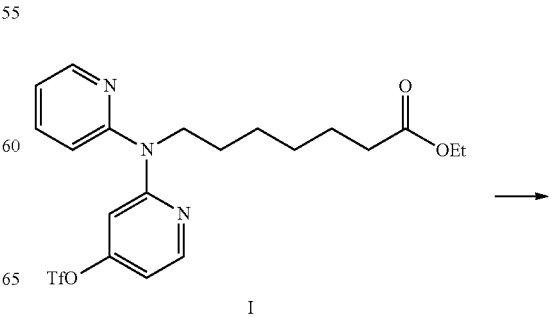

I

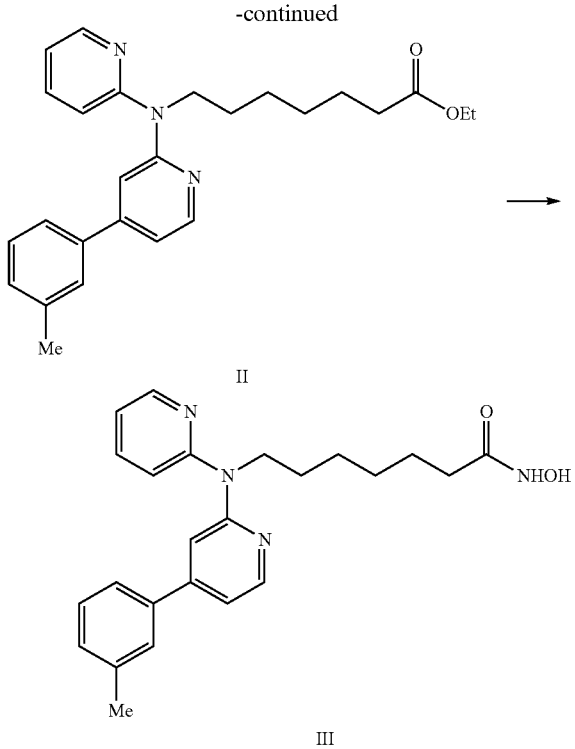

7-[Pyridin-2-yl-(4-m-tolyl-pyridin-2-yl)-amino]heptanoic acid ethyl ester (II)

Compound I (56 mg, 0.117 mmol, prepared using the method outlined above for Example 21), Pd(PPh₃)₄ (14 mg, 0.013 mmol), m-tolylboronic acid (32 mg, 0.235 mmol) and potassium carbonate (65 mg, 0.47 mmol) were stirred in toluene (3 mL) and water (1.5 mL) at 120° C. under microwave irradiation (300 W) for 30 min. The reaction mixture was then poured onto brine (30 mL) and extracted with EtOAc (2×20 mL). The organic phases were combined then dried over MgSO₄, filtered, and subsequently evaporated under reduced pressure. The resulting residue was purified by silica gel column chromatography eluting with hexane/EtOAc (90:10 to 80:20) to furnish II as a colourless oil (41 mg, 84%).

$^1$H NMR (400 MHz, CDCl₃) $\delta_H$: 8.39 (d, J=5.0 Hz, 1H), 8.37 (dd, J=1.3, 5.3 Hz, 1H), 7.57-7.50 (m, 1H), 7.39-7.32 (m, 3H), 7.27 (br. s, 1H), 7.23 (d, J=6.5 Hz, 1H), 7.13-7.07 (m, 2H), 6.87 (dd, J=5.3, 6.8 Hz, 1H), 4.23 (t, J=7.0 Hz, 2H), 4.11 (q, J=7.5 Hz, 2H), 2.42 (s, 3H), 2.27 (t, J=7.5 Hz, 2H), 1.75 (quin, J=7.4 Hz, 2H), 1.62 (quin, J=7.5 Hz, 2H), 1.45-1.31 (m, 4H), 1.25 (t, J=7.3 Hz, 3H). MW: 417.54. LCMS (ES). found 418.2 [MH]⁺.

7-[Pyridin-2-yl-(4-m-tolyl-pyridin-2-yl)-amino]heptanoic acid hydroxyamide (III)

HONH₂ (50% aqueous, 2 mL) was added to II (31 mg, 0.074 mmol) in DMF (0.5 mL) and MeOH (2 mL) at rt. The reaction mixture was stirred for 24 h, after which the solvents were evaporated under reduced pressure. The resulting residue was dissolved and co-evaporated with toluene (2×2 mL) then was purified by silica gel column chromatography eluting with CH₂Cl₂/MeOH (100:4 to 100:7) to furnish III as a colourless oil (18 mg, 62%).

$^1$H NMR (400 MHz, CDCl₃) $\delta_H$: 8.43-8.34 (m, 2H), 7.57 (t, J=7.0 Hz, 1H), 7.38-7.32 (m, 3H), 7.24 (br. s, 2H), 7.14 (d, J=4.5 Hz, 1H), 7.09 (d, J=8.0 Hz, 1H), 6.91 (dd, J=5.3, 6.8 Hz, 1H), 4.22 (t, J=7.3 Hz, 2H), 2.42 (s, 3H), 2.19-2.10 (m, 2H), 1.77-1.63 (m, 4H), 1.48-1.32 (m, 4H). MW: 404.50. LCMS (ES). found 405.2 [MH]⁺.

We claim:

1. A compound of the formula

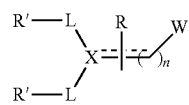

wherein:
⋯ is a single bond and X is N; and wherein:
n is 1 to 10;
R is H;
each R' is independently selected from H and QR₁;
each Q is a bond,
each R₁ is independently selected from C₁-C₁₀ alkyl, C₂-C₁₀ alkenyl, C₂-C₁₀ alkynyl, heteroaryl, C₁-C₁₀ cycloalkyl, and halogen;
L is pyridyl; and
W is CONHOH;
or a pharmaceutically acceptable salt thereof.

2. A compound according to claim 1, wherein at least one R' is H, or C₁-C₁₀ alkyl or O—(C₁-C₁₀ alkyl).

3. A compound according to claim 1, wherein n is 3 to 6.

4. A pharmaceutical composition comprising a compound according to claim 1, and a pharmaceutically acceptable carrier or diluent.

5. A composition according to claim 4, which is in a form suitable for oral, rectal, parenteral, intranasal or transdermal administration or administration by inhalation or by suppository.

* * * * *